US008676293B2

(12) United States Patent
Breen et al.

(10) Patent No.: US 8,676,293 B2
(45) Date of Patent: Mar. 18, 2014

(54) DEVICES, SYSTEMS AND METHODS FOR MEASURING AND EVALUATING THE MOTION AND FUNCTION OF JOINT STRUCTURES AND ASSOCIATED MUSCLES, DETERMINING SUITABILITY FOR ORTHOPEDIC INTERVENTION, AND EVALUATING EFFICACY OF ORTHOPEDIC INTERVENTION

(75) Inventors: Alan Breen, Cristchurch (GB); Adam Deitz, San Francisco, CA (US)

(73) Assignee: AECC Enterprises Ltd., Bournemouth (GB)

( * ) Notice: Subject to any disclaimer, the term of this patent is extended or adjusted under 35 U.S.C. 154(b) by 1032 days.

(21) Appl. No.: 11/734,623

(22) Filed: Apr. 12, 2007

(65) Prior Publication Data

US 2007/0287900 A1    Dec. 13, 2007

Related U.S. Application Data

(60) Provisional application No. 60/792,108, filed on Apr. 13, 2006, provisional application No. 60/868,427, filed on Dec. 4, 2006, provisional application No. 60/868,801, filed on Dec. 6, 2006.

(51) Int. Cl.
*A61B 5/00*    (2006.01)

(52) U.S. Cl.
USPC ............ 600/407; 600/410; 600/415; 600/425

(58) Field of Classification Search
USPC .................................. 600/407, 410, 415, 425
See application file for complete search history.

(56) References Cited

U.S. PATENT DOCUMENTS 3,678,190 A    7/1972    Cook
4,210,317 A    7/1980    Spann et al.
(Continued)

FOREIGN PATENT DOCUMENTS

AU    2007238017 B2    4/2007
DE    20009875 U1    10/2000
(Continued)

OTHER PUBLICATIONS

Breen, et al. Quantitative analysis of lumbar spine intersegmental motion. European Journal of Physical Medicine and Rehabilitation. 1993; 3(5): 182-90.
(Continued)

*Primary Examiner* — Peter Luong
(74) *Attorney, Agent, or Firm* — Cecily Anne O'Regan; Greenberg Traurig, LLP

(57) ABSTRACT

An apparatus and process for measuring the motion of internal joint structures during and for measuring the function of muscles involved with the motion of a joint of a subject are disclosed. The apparatus can be configured in three forms: a horizontal, vertical, or butterfly motion control device. Each configuration comprises a static member and a moving member, in which the moving member operates to move or be moved by the subject being studied. Also disclosed are processes for using each apparatus to measure of the relative motion of a skeletal structures in a subject, in which the subject is positioned in the apparatus and commanded to move while diagnostic medical images are taken or captured. Additionally, processes for using each apparatus to specifically measure and collect data on the function of the subject's muscles are disclosed.

90 Claims, 27 Drawing Sheets

(56) References Cited

U.S. PATENT DOCUMENTS

| | | |
|---|---|---|
| 4,404,590 A | 9/1983 | Mayer et al. |
| 4,611,581 A | 9/1986 | Steffee |
| 4,803,734 A | 2/1989 | Onishi et al. |
| 4,805,602 A | 2/1989 | Puno et al. |
| 4,922,909 A | 5/1990 | Little et al. |
| 5,000,165 A | 3/1991 | Watanabe |
| 5,019,081 A | 5/1991 | Watanabe |
| 5,058,602 A | 10/1991 | Brody |
| 5,090,042 A | 2/1992 | Bejjani et al. |
| 5,099,859 A | 3/1992 | Bell |
| 5,129,900 A | 7/1992 | Asher et al. |
| 5,203,346 A | 4/1993 | Fuhr et al. |
| 5,316,018 A | 5/1994 | O'Brien |
| 5,320,640 A | 6/1994 | Riddle et al. |
| 5,330,417 A | 7/1994 | Petersen et al. |
| 5,349,956 A * | 9/1994 | Bonutti ............ 600/425 |
| 5,400,800 A | 3/1995 | Jain et al. |
| 5,414,811 A | 5/1995 | Parulski et al. |
| 5,427,116 A * | 6/1995 | Noone ............ 600/587 |
| 5,442,729 A | 8/1995 | Kramer et al. |
| 5,443,505 A | 8/1995 | Wong et al. |
| 5,445,152 A | 8/1995 | Bell et al. |
| 5,474,555 A | 12/1995 | Puno et al. |
| 5,505,208 A | 4/1996 | Toomim et al. |
| 5,548,326 A | 8/1996 | Michael |
| 5,575,792 A | 11/1996 | Errico et al. |
| 5,582,186 A | 12/1996 | Wiegand |
| 5,582,189 A | 12/1996 | Pannozzo |
| 5,590,271 A | 12/1996 | Klinker |
| 5,640,200 A | 6/1997 | Michael |
| 5,643,263 A | 7/1997 | Simonson |
| 5,683,392 A | 11/1997 | Richelsoph et al. |
| 5,688,274 A | 11/1997 | Errico et al. |
| 5,690,630 A | 11/1997 | Errico et al. |
| 5,707,643 A | 1/1998 | Ogura et al. |
| 5,715,334 A | 2/1998 | Peters |
| 5,725,527 A | 3/1998 | Biedermann et al. |
| 5,740,267 A | 4/1998 | Echerer et al. |
| 5,741,255 A | 4/1998 | Krag et al. |
| 5,748,703 A | 5/1998 | Cosman |
| 5,755,675 A | 5/1998 | Sihvonen |
| 5,772,592 A | 6/1998 | Cheng et al. |
| 5,772,595 A | 6/1998 | Votruba et al. |
| 5,784,431 A | 7/1998 | Kalend et al. |
| 5,792,077 A * | 8/1998 | Gomes ............ 600/595 |
| 5,797,911 A | 8/1998 | Sherman et al. |
| 5,810,006 A | 9/1998 | Votruba et al. |
| 5,813,406 A | 9/1998 | Kramer et al. |
| 5,824,072 A | 10/1998 | Wong et al. |
| 5,838,759 A | 11/1998 | Armistead |
| 5,863,293 A | 1/1999 | Richelsoph |
| 5,879,350 A | 3/1999 | Sherman et al. |
| 5,885,285 A | 3/1999 | Simonson |
| 5,891,060 A | 4/1999 | McGregor et al. |
| 5,891,145 A | 4/1999 | Morrison et al. |
| 5,899,859 A | 5/1999 | Votruba et al. |
| 5,931,781 A | 8/1999 | De Boer |
| 5,954,674 A | 9/1999 | Fuhr |
| 5,964,760 A | 10/1999 | Richelsoph |
| 6,002,959 A | 12/1999 | Steiger et al. |
| 6,010,503 A | 1/2000 | Richelsoph et al. |
| 6,019,759 A | 2/2000 | Rogozinski |
| 6,022,350 A | 2/2000 | Ganem |
| 6,049,740 A | 4/2000 | Whitehead et al. |
| 6,074,391 A | 6/2000 | Metz-Stavenhagen et al. |
| 6,075,905 A | 6/2000 | Herman et al. |
| 6,077,262 A | 6/2000 | Schlapfer et al. |
| 6,090,111 A | 7/2000 | Nichols |
| 6,132,430 A | 10/2000 | Wagner |
| 6,141,579 A | 10/2000 | Bonutti |
| 6,155,993 A | 12/2000 | Scott |
| 6,248,105 B1 | 6/2001 | Schlapfer et al. |
| 6,269,565 B1 | 8/2001 | Inbar et al. |
| 6,276,799 B1 | 8/2001 | Van Saarloos et al. |
| 6,280,395 B1 | 8/2001 | Appel et al. |
| 6,290,703 B1 | 9/2001 | Ganem |
| 6,298,259 B1 * | 10/2001 | Kucharczyk et al. ......... 600/411 |
| 6,351,547 B1 | 2/2002 | Johnson et al. |
| 6,427,022 B1 | 7/2002 | Craine et al. |
| 6,428,490 B1 | 8/2002 | Kramer et al. |
| 6,434,264 B1 | 8/2002 | Asar |
| 6,451,021 B1 | 9/2002 | Ralph et al. |
| 6,469,717 B1 | 10/2002 | Wineke et al. |
| 6,471,705 B1 | 10/2002 | Biedermann et al. |
| 6,497,672 B2 | 12/2002 | Kramer |
| 6,524,315 B1 | 2/2003 | Selvitelli et al. |
| 6,540,749 B2 | 4/2003 | Schafer et al. |
| 6,542,574 B2 | 4/2003 | Grodzins |
| 6,547,790 B2 | 4/2003 | Harkey et al. |
| 6,560,476 B1 * | 5/2003 | Pelletier et al. ............ 600/410 |
| 6,565,565 B1 | 5/2003 | Yuan et al. |
| 6,608,916 B1 | 8/2003 | Wei et al. |
| 6,608,917 B1 | 8/2003 | Wei et al. |
| 6,697,659 B1 | 2/2004 | Bonutti |
| 6,698,885 B2 | 3/2004 | Berger et al. |
| 6,719,750 B2 | 4/2004 | Varner et al. |
| 6,726,691 B2 | 4/2004 | Osorio et al. |
| 6,866,643 B2 | 3/2005 | Kramer |
| 6,882,744 B2 | 4/2005 | Oosawa |
| 6,890,312 B1 | 5/2005 | Prister et al. |
| 6,907,280 B2 * | 6/2005 | Becerra et al. ............ 600/407 |
| 6,963,768 B2 | 11/2005 | Ho et al. |
| 6,964,781 B2 | 11/2005 | Brubaker et al. |
| 6,990,368 B2 | 1/2006 | Simon |
| 7,000,271 B2 | 2/2006 | Varadharajulu |
| 7,034,063 B2 | 4/2006 | Nienhaus et al. |
| 7,046,830 B2 | 5/2006 | Gerard et al. |
| 7,050,537 B2 | 5/2006 | Tsujii |
| 7,110,587 B1 | 9/2006 | Natanzon et al. |
| 7,117,027 B2 | 10/2006 | Zheng et al. |
| 7,127,090 B2 | 10/2006 | Kreang-Arekul et al. |
| 7,133,066 B2 | 11/2006 | Bourret |
| 7,153,307 B2 | 12/2006 | Scribner et al. |
| 7,158,661 B2 | 1/2007 | Inoue |
| 7,184,814 B2 | 2/2007 | Lang et al. |
| 7,241,303 B2 | 7/2007 | Reiss et al. |
| 7,243,387 B2 | 7/2007 | Schindler et al. |
| 7,266,406 B2 * | 9/2007 | Kroeckel ............ 600/410 |
| 7,333,649 B2 | 2/2008 | Nagata et al. |
| 7,343,635 B2 | 3/2008 | Jackson |
| 7,502,641 B2 | 3/2009 | Breen |
| 7,697,971 B1 * | 4/2010 | Green et al. ............ 600/415 |
| 7,747,309 B2 * | 6/2010 | Prince ............ 600/420 |
| 7,780,703 B2 | 8/2010 | Yuan et al. |
| 7,837,635 B2 | 11/2010 | Lissek et al. |
| 2002/0120272 A1 | 8/2002 | Yuan et al. |
| 2003/0081837 A1 | 5/2003 | Williame et al. |
| 2003/0086596 A1 | 5/2003 | Hipp et al. |
| 2003/0220648 A1 | 11/2003 | Osorio et al. |
| 2003/0225327 A1 | 12/2003 | Willen et al. |
| 2004/0010260 A1 | 1/2004 | Scribner et al. |
| 2004/0098803 A1 | 5/2004 | Schindler et al. |
| 2004/0141591 A1 | 7/2004 | Izuhara |
| 2004/0172145 A1 | 9/2004 | Varadharajulu |
| 2004/0225296 A1 | 11/2004 | Reiss et al. |
| 2005/0107681 A1 * | 5/2005 | Griffiths ............ 600/410 |
| 2005/0187459 A1 | 8/2005 | Trequattrini et al. |
| 2005/0222505 A1 * | 10/2005 | Damadian et al. ............ 600/415 |
| 2005/0240193 A1 | 10/2005 | Layne et al. |
| 2005/0259794 A1 | 11/2005 | Breen |
| 2006/0020196 A1 | 1/2006 | Elias |
| 2006/0149136 A1 | 7/2006 | Seto et al. |
| 2006/0185091 A1 | 8/2006 | Jackson |
| 2006/0264952 A1 | 11/2006 | Nelson et al. |
| 2007/0067034 A1 | 3/2007 | Chirico et al. |
| 2008/0039867 A1 | 2/2008 | Feussner et al. |
| 2008/0125678 A1 | 5/2008 | Breen |
| 2009/0099481 A1 | 4/2009 | Deitz |
| 2009/0285466 A1 | 11/2009 | Hipp et al. |

(56) References Cited

U.S. PATENT DOCUMENTS

| | | | |
|---|---|---|---|
| 2012/0130285 A1 | 5/2012 | Deitz | |
| 2012/0321168 A1 | 12/2012 | Deitz | |

FOREIGN PATENT DOCUMENTS

| | | | |
|---|---|---|---|
| EP | 804032 | A2 | 10/1997 |
| EP | 1219240 | A2 | 7/2002 |
| EP | 1219240 | A3 | 11/2002 |
| EP | 1519681 | B1 | 11/2006 |
| JP | 7284020 | A2 | 10/1995 |
| WO | WO 01/93764 | A1 | 12/2001 |
| WO | WO 2004/004570 | A1 | 1/2004 |
| WO | WO 2005/007217 | A2 | 1/2005 |
| WO | WO2007/121337 | A2 | 4/2007 |
| WO | WO2007/121337 | A3 | 4/2007 |
| WO | WO2009/0049062 | A2 | 4/2009 |
| WO | WO2009/0049062 | A3 | 4/2009 |
| WO | WO2009/0049062 | A9 | 4/2009 |
| WO | WO 2012/082615 | | 6/2012 |
| WO | WO 2012/082615 | A3 | 6/2012 |

OTHER PUBLICATIONS

Breen, et al. Spine kinematics: a digital videofluoroscopic technique. Journal of Biomedical Engineering. 1989; 11: 224-8.

Bryant. Method for determining vertebral body positions in the sagittal plane using skin markers. Spine 1989; 14(3): 258-65.

Carragee, et al. Low-pressure positive Discography in subjects asymptomatic of significant low back pain illness. Spine. 2006; 31(5): 505-509.

Cholewicki, et al. Method for measuring vertebral kinematics from videofluoroscopy. Clinical Biomechanics. 1991; 6: 73-8.

Cholewicki, et al. Lumbar posterior ligament involvement during extremely heavy lifts estimated from fluoroscopic measurements. Journal of Biomechanics. 1992; 25(1): 17-28.

Esses, et al. Kinematic evaluation of lumbar fusion techniques. Spine 1996; 21(6): 676-84.

Fujiwara, et al. The relationship between disc degeneration, facet joint osteoarthritis, and stability of the degenerative lumbar spine. Journal of Spinal Disorders. 2000; 13: 444-50.

Harada, et al. Cineradiographic motion analysis of normal lumbar spine during forward and backward flexion. Spine. 2000; 25: 1932-7.

Johnsson, et al. Mobility of the lower lumbar spine after posterolateral fusion determined by roentgen stereophotogrammetric analysis. Spine. 1990. 15: 347-50.

Jones, M. D. Cervical spine cineradiography after traffic accidents. Archives of Surgery. 1962; 85: 974-81.

Kaigle, et al. Muscular and kinematic behavior of the lumbar spine during flexion-extension. Journal of Spinal Disorders. 1998; 11(2): 163-174.

Lariviere, et al. A triaxial dynamometer to monitor lateral bending and axial rotation moments during static trunk extension efforts. Clin Biomech (Bristol, Avon). Jan. 2001;16(1):80-83.

Lawrence, J. S. Disc degeneration. Its frequency and relationship to symptoms. Annals of Rheumatic Diseases. 1969; 28: 121-38.

Lee et al. Development and validation of a new teclinique for assessing lumbar spine motion. Spine. 2002; 27(8): E215-20.

McGregor et al. Spinal motion in lumbar degenerative disc disease. J one Joint Surg (Br). 1998; 80-B: 1009-1013.

Stokes, et al. Trunk muscular activation patterns and responses to transient force perturbation in persons with self-reported low back pain. Eur Spine J. 2006; 15:658-667.

Takayanagi, et al. Using cineradiography for continuous dynamic-motion analysis of the lumbar spine. Spine. 2001; 26(17): 1858-1865.

Waddell, G. The Back Pain Revolution. Churchill Livingstone. Eninburgh. 1998; Ch2 p. 23.

Zheng, et al. Lumbar spine visualisation based on kinematic analysis from videofluoroscopic imaging. Medical Engineering and Physics. 2003; 25; 171-179.

Breen, et al. Lumbar spine motion palpation compared with objective intervertebral motion analysis: preliminary findings. European Journal of Chiropractic. 2002; 50, 27-32.

Kleissen, Simultaneous Measurement of Surface EMG and Movements for Clinical Use, Medical & Biological Engineering, 27(3) pp. 291-297 (1989).

Kondracki, Digital Videofluoroscopy, Manual Therapy (1996) 1, 146-48.

Quick, et al. Real-Time MRI of Joint Movement with True FISP, J. Mag. Res. Imaging vol. 15(6), pp. 710-715 (2002).

Teyhen, et al., A New Technique for Digital Fluoriscopic Video Assessment of Sagittal Plane Lumbar Spine Motion, Spine vol. 30(14), pp. E406-E413 (2005).

Waddell, G. The Back Pain Revolution. Churchill Livingstone. Edinburgh. 1998; Ch2 p. 23.

Wong, et al. Continuous dynamic spinal motion analysis. Spine. 2006; 31(4): 414-419.

Zheng, et al. Automatic Lumbar Vertebrae Segmentation in Fluoroscopic Images via Optimised Concurrent Hough Transform, 23rd Annual International Conf of IEEE Engineering in Med and Biology (2001).

* cited by examiner

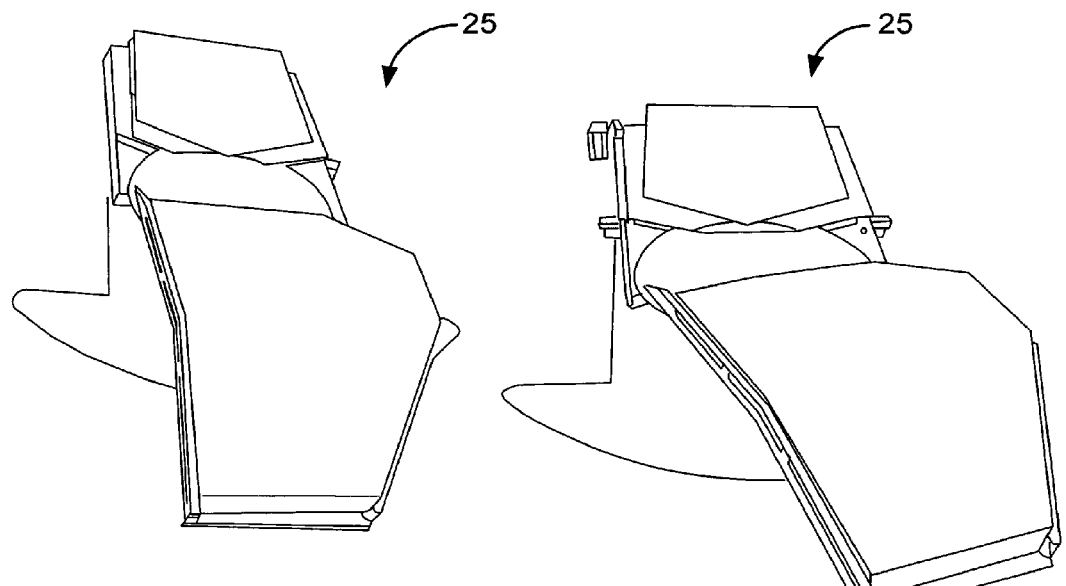
Fig. 7c
Fig. 7d
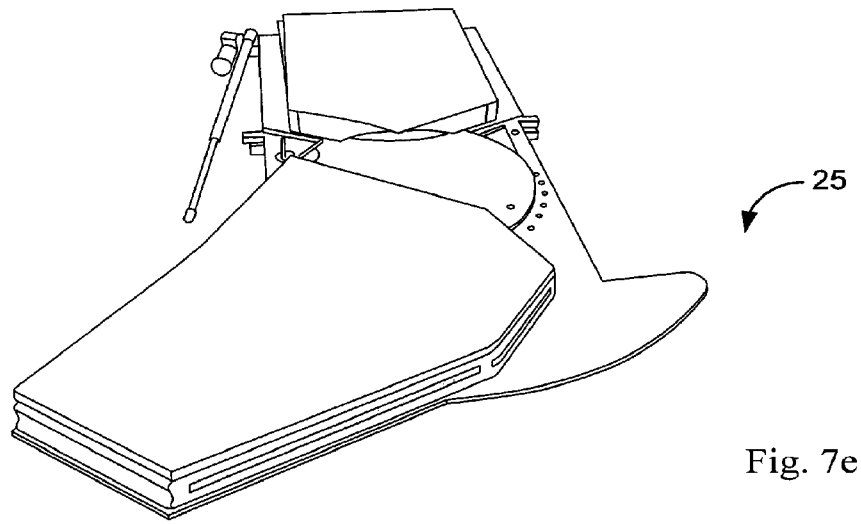
Fig. 7e

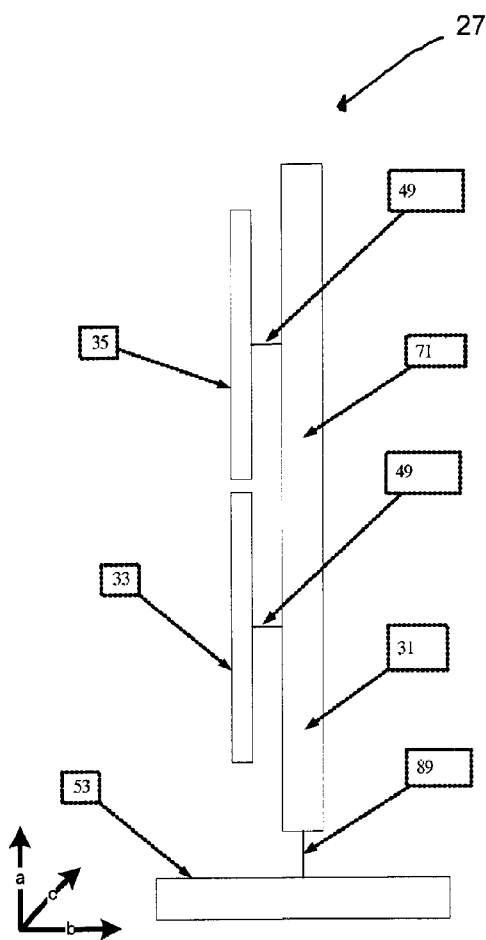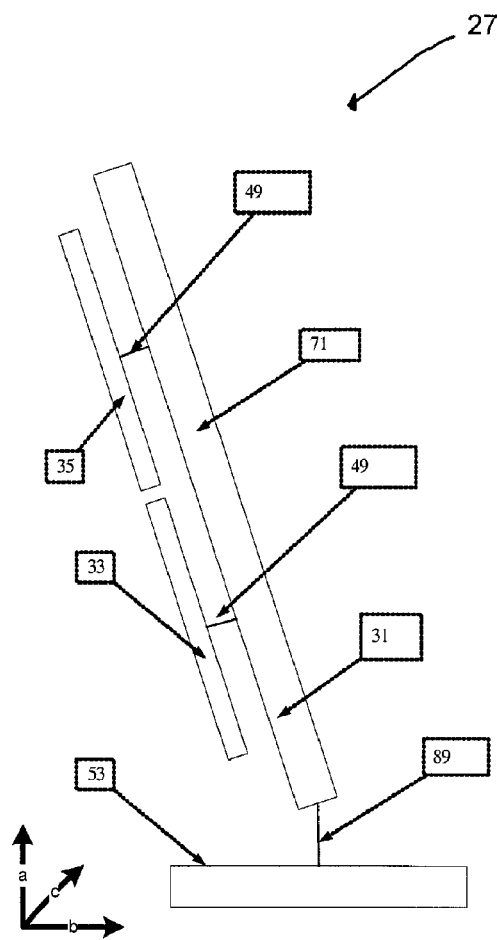
Fig. 12a
Fig. 12b

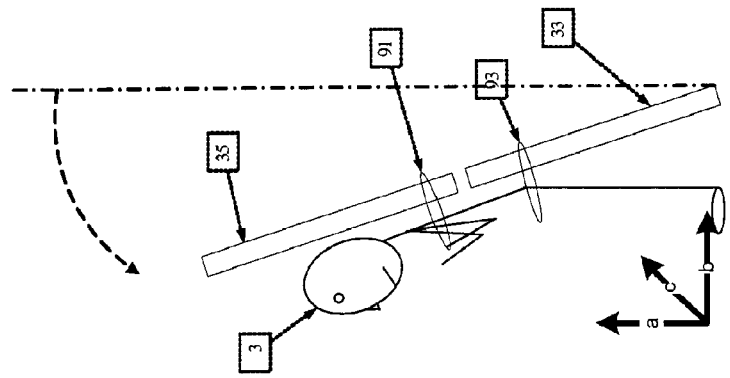
Fig. 14d
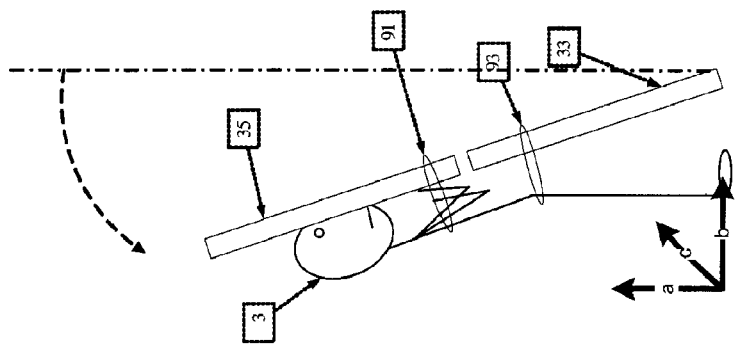
Fig. 14c
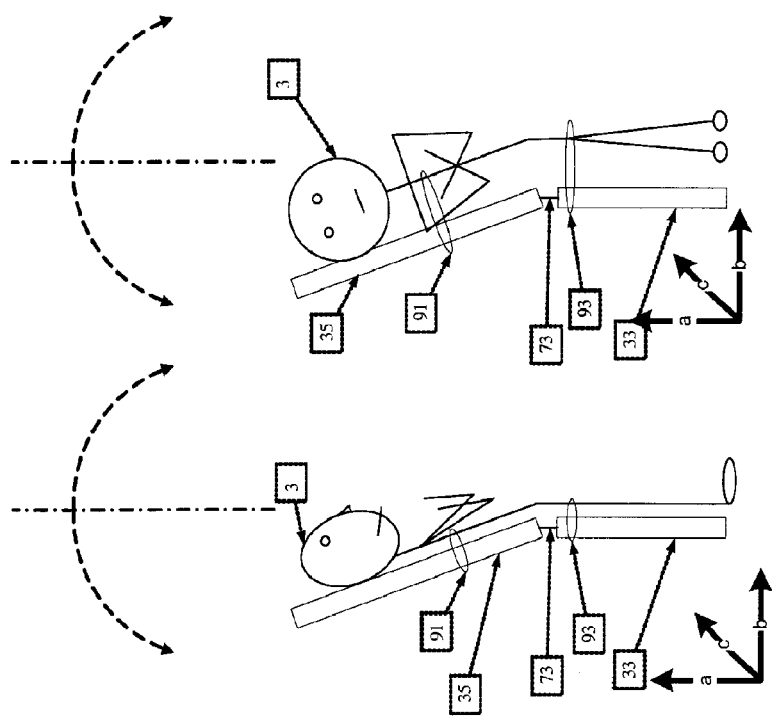
Fig. 14b
Fig. 14a

Fig. 16a
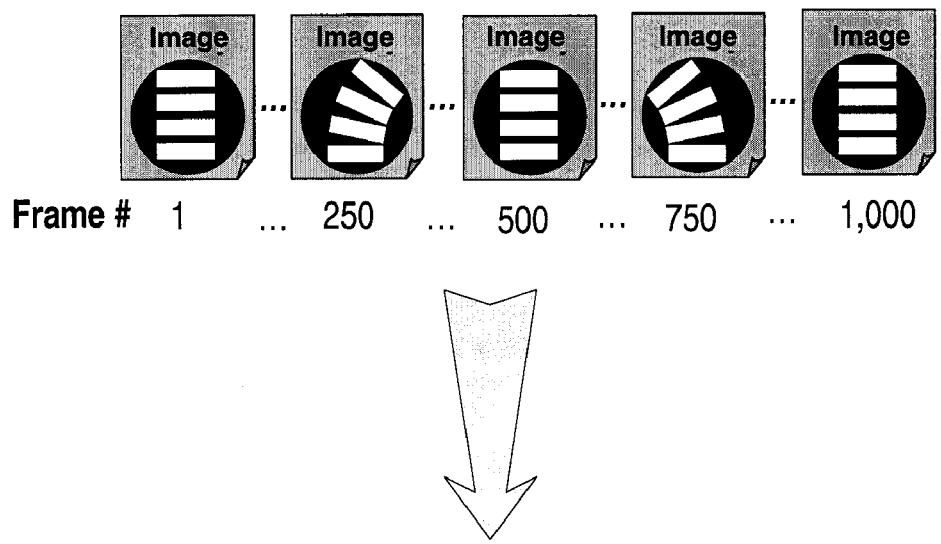
OUTPUT
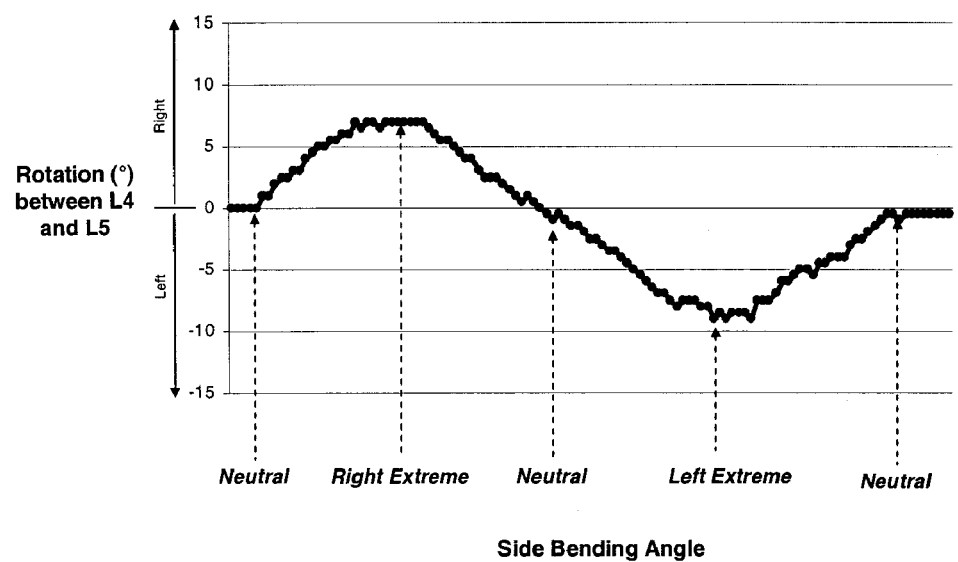
Fig. 16b

US 8,676,293 B2

DEVICES, SYSTEMS AND METHODS FOR MEASURING AND EVALUATING THE MOTION AND FUNCTION OF JOINT STRUCTURES AND ASSOCIATED MUSCLES, DETERMINING SUITABILITY FOR ORTHOPEDIC INTERVENTION, AND EVALUATING EFFICACY OF ORTHOPEDIC INTERVENTION

CROSS-REFERENCE

This application claims the benefit of U.S. Provisional Application 60/792,108 by Breen entitled Method and Apparatus for Measuring the Surface Motion of Joints filed on Apr. 13, 2006, U.S. Provisional Application 60/868,427 by Breen entitled Method and Apparatus for Measuring the Motion of Internal Joint Structures and the Function of Associated Muscles filed Dec. 4, 2006 and U.S. Provisional Application 60/868,801 by Breen entitled Method and Apparatus for Measuring the Motion of Internal Joint Structures and the Function of Associated Muscles filed Dec. 6, 2006, under 35 U.S.C. §365.

TECHNICAL FIELD

The present invention relates to devices, systems and methods for measuring and evaluating the motion and pathologies of a target joint structure in a subject. The invention more specifically relates to devices, systems and methods for measuring and evaluating the motion of the spine and analyzing spinal pathologies. The invention also enables a determination of whether, and to what extent, muscles associated with a joint are impacting a target joint's biomechanics. The invention enables the biomechanics of a joint to be evaluated with a precision of less than 5°, preferably less than 3°, and even more preferably less than 1° which enables, for example, improved pseudoarthrosis detection, level-specific detection of hypermobility, detection of vertebral stiffness and detection of paradoxical motion, to name a few. The enhanced biomechanical assessment facilitates orthopedic procedure and/or device suitability determination as well as orthopedic procedure and/or device evaluation.

BACKGROUND OF THE INVENTION

One of the most prevalent joint problems is back pain, particularly in the "small of the back" or lumbosacral (L4-S1) region, shown in FIG. 1A. In many cases, the pain severely limits a person's functional ability and quality of life. Such pain can result from a variety of spinal pathologies. Through disease or injury, the vertebral bodies, intervertebral discs, laminae, spinous process, articular processes, or facets of one or more spinal vertebrae can become damaged, such that the vertebrae no longer articulate or properly align with each other. This can result in an undesired anatomy, loss of mobility, and pain or discomfort. Duke University Medical Center researchers found that patients suffering from back pain in the United States consume more than $90 billion annually in health care expenses, with approximately $26 billion being directly attributable to treatment. Additionally, there is a substantial impact on the productivity of workers as a result of lost work days. Similar trends have also been observed in the United Kingdom and other countries. As a result of this problem, increased funding is being applied toward developing better and less invasive orthopedic intervention devices and procedures.

Other the years the increased funding has led to the development of various orthopedic interventions. These include interventions suitable for fixing the spine and/or sacral bone adjacent the vertebra, as well as attaching devices used for fixation, including: U.S. Pat. No. 6,290,703, to Ganem, for Device for Fixing the Sacral Bone to Adjacent Vertebrae During Osteosynthesis of the Backbone; U.S. Pat. No. 6,547, 790, to Harkey, III, et al., for Orthopaedic Rod/Plate Locking Mechanisms and Surgical Methods; U.S. Pat. No. 6,074,391, to Metz-Stavenhagen, et al., for Receiving Part for a Retaining Component of a Vertebral Column Implant; U.S. Pat. No. 5,891,145, to Morrison, et al., for Multi-Axial Screw; U.S. Pat. No. 6,090,111, to Nichols, for Device for Securing Spinal Rods; U.S. Pat. No. 6,451,021, to Ralph, et al., for Polyaxial Pedicle Screw Having a Rotating Locking Element; U.S. Pat. No. 5,683,392, to Richelsoph, et al., for Multi-Planar Locking Mechanism for Bone Fixation; U.S. Pat. No. 5,863,293, to Richelsoph, for Spinal Implant Fixation Assembly; U.S. Pat. No. 5,964,760, to Richelsoph, for Spinal Implant Fixation Assembly; U.S. Pat. No. 6,010,503, to Richelsoph, et al., for Locking Mechanism; U.S. Pat. No. 6,019,759, to Rogozinski, for Multi-Directional Fasteners or Attachment Devices for Spinal Implant Elements; U.S. Pat. No. 6,540,749, to Schafer, et al., for Bone Screw; U.S. Pat. No. 6,077,262, to Schlapfer, for Posterior Spinal Implant; U.S. Pat. No. 6,248,105, to Schlapfer, et al., for Device for Connecting a Longitudinal Support with a Pedicle Screw; U.S. Pat. No. 6,524,315, to Selvitelli, et al., for Orthopaedic Rod/Plate Locking Mechanism; U.S. Pat. No. 5,797,911, to Sherman, et al., for Multi-Axial Bone Screw Assembly; U.S. Pat. No. 5,879,350, to Sherman, et al., for Multi-Axial Bone Screw Assembly; U.S. Pat. No. 5,885,285, to Simonson, For Spinal Implant Connection Assembly; U.S. Pat. No. 5,643,263, to Simonson for Spinal Implant Connection Assembly; U.S. Pat. No. 6,565, 565, to Yuan, et al., for Device for Securing Spinal Rods; U.S. Pat. No. 5,725,527, to Biederman, et al., for Anchoring Member; U.S. Pat. No. 6,471,705, to Biederman, et al., for Bone Screw; U.S. Pat. No. 5,575,792, to Errico, et al., for Extending Hook and Polyaxial Coupling Element Device for Use with Top Loading Rod Fixation Devices; U.S. Pat. No. 5,688, 274, to Errico, et al., for Spinal Implant Device having a Single Central Rod and Claw Hooks; U.S. Pat. No. 5,690,630, to Errico, et al., for Polyaxial Pedicle Screw; U.S. Pat. No. 6,022,350, to Ganem, for Bone Fixing Device, in Particular for Fixing to the Sacrum during Osteosynthesis of the Backbone; U.S. Pat. No. 4,805,602, to Puno, et al., for Transpedicular Screw and Rod System; U.S. Pat. No. 5,474,555, to Puno, et al., for Spinal Implant System; U.S. Pat. No. 4,611, 581, to Steffee, for Apparatus for Straightening Spinal Columns; U.S. Pat. No. 5,129,900, to Asher, et al., for Spinal Column Retaining Method and Apparatus; U.S. Pat. No. 5,741,255, to Krag, et al., for Spinal Column Retaining Apparatus; U.S. Pat. No. 6,132,430, to Wagner, for Spinal Fixation System; U.S. Publication No. 2002/0120272, and to Yuan, et al., for Device for Securing Spinal Rods.

Another type of orthopedic intervention is the spinal treatment decompressive laminectomy. Where spinal stenosis (or other spinal pathology) results in a narrowing of the spinal canal and/or the intervertebral foramen (through which the spinal nerves exit the spine), and neural impingement, compression and/or pain results, the tissue(s) (hard and/or soft tissues) causing the narrowing may need to be resected and/or removed. A procedure which involves excision of part or all of the laminae and other tissues to relieve compression of nerves is called a decompressive laminectomy. See, for example, U.S. Pat. No. 5,019,081, to Watanabe, for Laminectomy Surgical Process; U.S. Pat. No. 5,000,165, to Watanabe, for Lumbar Spine Rod Fixation System; and U.S. Pat. No. 4,210,317, to Spann, et al., for Apparatus for Supporting and Positioning the Arm and Shoulder. Depending upon the extent of the decompression, the removal of support structures such as the facet joints and/or connective tissues (either because these tissues are connected to removed structures or are resected to access the surgical site) may result in instability of the spine, necessitating some form of supplemental support such as spinal fusion, discussed above.

Other orthopedic interventional techniques and processes have also been developed to treat various spinal and joint pathologies. For example, U.S. Patent Pub. 20030220648 to Osorio for Methods and devices for treating fractured and/or diseased bone; 20040010260 to Scribner for Systems and methods for placing materials into bone; 20040225296 to Reiss for Devices and methods using an expandable body with internal restraint for compressing cancellous bone; 20050240193 to Layne for Devices for creating voids in interior body regions and related methods; 20060149136 to Seto for Elongating balloon device and method for soft tissue expansion; 20070067034 to Chirico for Implantable Devices and Methods for Treating Micro-Architecture Deterioration of Bone Tissue; 20060264952 to Nelson for Methods of Using Minimally Invasive Actuable Bone Fixation Devices.

Health care providers rely on an understanding of joint anatomy and mechanics when evaluating a subject's suspected joint problem and/or biomechanical performance issue. Understanding anatomy and joint biomechanics assists in the diagnosis and evaluation of a subject for an orthopedic intervention. However, currently available diagnostic tools are limited in the level of detail and analysis that can be achieved. Typically, when treating joint problems, the intention is to address a specific structural or mechanical problem within the joint. For example, a surgeon might prescribe a spinal fusion procedure to physically immobilize the vertebra of a subject suffering from vertebral instability, or a physical therapist might prescribe exercises to strengthen a specific tendon or muscle that is responsible for a joint problem, etc.

It follows, therefore, that the extent to which a specific treatable joint defect can be identified and optimally treated directly impacts the success of any treatment protocol. Currently available orthopedic diagnostic methods are capable of detecting a limited number of specific and treatable defects. These techniques include X-Rays, MRI, discography, and physical exams of the patient. In addition, spinal kinematic studies such as flexion/extension X-rays are used to specifically detect whether or not a joint has dysfunctional motion. These methods have become widely available and broadly adopted into the practice of treating joint problems and addressing joint performance issues. However, currently available diagnostic techniques provide measurement data that is imprecise and often inconclusive which results in an inability to detect many types of pathologies or accurately assess pathologies that might be considered borderline. As a result, a significant number of patients having joint problems remain undiagnosed and untreated using current techniques, or worse are misdiagnosed and mistreated due to the poor clinical efficacy of these techniques.

For example, currently available techniques for conducting spinal kinematic studies are often unable to determine whether a joint dysfunction is a result of the internal joint structure per se, or whether the dysfunction is a result of, or significantly impacted by, the surrounding muscular tissue. Additionally, there are no reliable techniques for identifying soft tissue injury. Muscle guarding is a well established concept that is hypothesized to be highly prevalent among sufferers of joint pain, specifically that of the neck and back. In muscle guarding, a subject responds to chronic pain by immobilizing the painful area through involuntary muscle involvement. The ability to isolate different muscle groups is desirable to determine which muscle group or combination of groups, if any, could be contributing to, or responsible for, any joint dysfunction.

Additionally, the level of entrenchment of muscle guarding behavior cannot currently be determined. With respect to treatment decisions, the operative question in determining the level of "entrenchment" of any observed muscle guarding is to determine if the muscle guarding behavior is one which conservative methods of therapy could address through non-surgical therapy, or alternatively determining that the muscle guarding behavior so "entrenched" that such efforts would be futile and surgery should be considered.

In some instances, joint dysfunctions may not always present themselves in the movements traditionally measured during spinal kinematic studies such as flexion-extension and side-bending in either "full" non-weight-bearing or "full" weight-bearing planes of movement, which correspond to lying down and standing up postures respectively. Certain painful movements occur during joint rotation when the plane of rotation is somewhere between these two postures. Certain other painful movements only occur when the subject is rotating his or her spine while in a bent posture. In the case of vertebral motion in full weight-bearing postures, gravitational forces are relatively evenly distributed across the surface area of the vertebrae. However in postures where the subject is standing with his/her spine bent, gravitational forces are concentrated on the sections of the vertebrae located toward the direction of the bend. Detecting motion dysfunctions that occur only when in a standing bent posture requires the replication of joint motion in that specific bent posture in a controlled, repeatable, and measurable manner during examination.

Further, assuming that a system of measuring the surface motion of joints and the motion between internal joint structures that accounts for various types of muscle involvements would be possible, there would be a need for investigational data from controlled clinical trials to be collected across a broad population of subjects to afford for comparative analyses between subjects. Such a comparative analysis across a broad population of subjects would be necessary for the purpose of defining "normal" and "unhealthy" ranges of such measurements, which would in turn form the basis for the diagnostic interpretation of such measurements.

There have been significant technological innovations to the field of orthopedic interventions over the last few decades, specifically with the use of prosthetic and therapeutic devices to correct mechanical and structural defects of the bones and joints and to restore proper joint function. There have also been significant advances in the application of chiropractic and physical therapy approaches to correct muscle-, ligament-, and tendon-related defects. There has not however, been a corresponding improvement in the diagnostic methods used to identify proper candidates for these interventions. As a result, the potential impact and utility of the improvements in orthopedic intervention has been limited.

Imaging is the cornerstone of all modern orthopedic diagnostics. The vast majority of diagnostic performance innovations have focused on static images. Static images are a small number of images of a joint structure taken at different points in the joint's range of motion, with the subject remaining still in each position while the image is being captured. Static imaging studies have focused mainly on detecting structural changes to the bones and other internal joint structures. An example of the diagnostic application of static imaging studies is with the detection of spinal disc degeneration by the use of plain X-rays, MR images and discograms. However, these applications yield poor diagnostic performance with an unacceptably high proportion of testing events yielding either inconclusive or false positive/false negative diagnostic results (Lawrence, J. S. (1969) Annals of Rheumatic Diseases 28: 121-37; Waddell, G. (1998) The Back Pain Revolution. Edinburgh, Churchill Livingstone Ch2 p22; Carragee et al. (2006) Spine 31(5): 505-509, McGregor et al. (1998) J Bone Joint Surg (Br) 80-B: 1009-1013; Fujiwara et al. (2000(a)) Journal of Spinal Disorders 13: 444-50).

Purely qualitative methods for visualizing joint motion have been available for some time using cine-radiography (Jones, M. D. (1962) Archives of Surgery 85: 974-81). More recently, computer edge extraction of vertebral images from fluoroscopy has been used to improve this visualization for use in animations (Zheng et al. (2003) Medical Engineering and Physics 25: 171-179). These references do not, however, provide for any form of measurement or identification of objectively defined motion abnormalities, and therefore is of very limited diagnostic value other than in the detection of grossly and visibly obvious abnormalities that would be detectable using static image analysis methods. Without any quantitative or objective measurement parameters defined, it is impossible to utilize such approaches in comparative analyses across wide populations of subjects, which is required for the purpose of the producing definitive diagnostic interpretations of the results as being either "normal" or "unhealthy". Further, there have been no diagnostically useful validations of qualitative motion patterns that are generally absent in non-sufferers but present in subjects suffering from known and specific joint functional derangements or symptoms, or vice versa.

A method for determining vertebral body positions using skin markers was developed (Bryant (1989) Spine 14(3): 258-65), but could only measure joint motion at skin positions and could not measure the motion of structures within the joint. There have been many examples skin marker based spine motion measurement that have all been similarly flawed.

Methods have been developed to measure changes to the position of vertebrae under different loads in dead subjects, whose removed spines were fused and had markers inserted into the vertebrae (Esses et al. (1996) Spine 21(6): 676-84). The motion of these markers was then measured in the presence of different kinds of loads on the vertebrae. This method is, however, inherently impractical for clinical diagnostic use. Other methods with living subjects have been able to obtain a high degree of accuracy in measuring the motion of internal joint structures by placing internal markers on the bones of subjects and digitally marking sets of static images (Johnsson et al. (1990) Spine 15: 347-50), a technique known as roentgen stereophotogrammetry analysis (RSA). However RSA requires the surgical implantation of these markers into subjects' internal joint structures, requires the use of two radiographic units simultaneously, and requires a highly complicated calibration process for every single test, and therefore is too invasive and too cumbersome a process for practicable clinical application.

Cine-radiography of uncontrolled weight-bearing motion (Harada et al (2000) Spine 25: 1932-7; Takavanagi et al. (2001) Spine 26(17): 1858-1865) has been used to provide a set of static images to which digital markers have been attached and transformed to give quantitative measurement of joint motion. Similar measurement of joint motion has been achieved using videofluoroscopy (Breen et al. (1989) Journal of Biomedical Engineering 11: 224-8; Cholewicki et al. (1991) Clinical Biomechanics 6: 73-8; Breen et al. (1993) European Journal of Physical Medicine and Rehabilitation 3(5): 182-90; Brydges et al. 1993). This method has also been used to study the effects on joint motion of weightlifting (Cholewicki, J. and S. M. McGill (1992) Journal of Biomechanics 25(1): 17-28). The prior art using this method involves a manual process in which internal joint structures are marked by hand with digital landmarks on digital image files of consecutive frames of videoflouroscopy recordings of a subject's joint motion. A computer then automatically determines the frame-to-frame displacement between such digital landmarks to derive quantitative measurements of the motion of joint structures (Lee et al. (2002) Spine 27(8): E215-20). Even more recently, this approach has been accomplished using an automatic registration process (Wong et al. (2006) Spine 31(4): 414-419) that eliminates the manual marking process and thus reduces the laboriousness of the previous processes. However both of these methods, as well as all of the other methods mentioned in this paragraph, studied the motion of joints based on the imaging of uncontrolled, weight-bearing body motion.

Using uncontrolled, weight-bearing motion to derive quantitative measurements of joint motion confounds the diagnostic interpretation of such measurements so as to render them diagnostically useless. The diagnostic interpretation of such measurements would normally be based on a comparative analysis of joint motion measurements across a wide population of subjects, and would strive to identify statistically significant differences in these measurements between "normal" and "unhealthy" subjects, such that any given subject can be classified as "normal" or "unhealthy" based on that subject's joint motion measurement values. For such purposes, it is necessary to reduce the background variability of measurements across tested subjects as much as possible, so that any observed difference between "normal" and "unhealthy" subjects can be definitively attributable to a specific condition. Not controlling the motion that is being studied introduces variability into these comparative analyses due to differences that exist across testing subjects with respect to each subject's individual range of motion, symmetry of motion, and regularity of motion. These differences affect the joint motion of each subject differently, and collectively serve to create wide variability among joint motion measurements across subjects. Controlling for these factors by ensuring a consistent, regular, and symmetric body part motion during diagnostic testing serves to minimize the effects of these factors on a subject's relevant joint motion measurements, thereby reducing the variability of such measurements across subjects and therefore increasing the likelihood that such measurements will yield useful diagnostic results.

In addition to failing to control motion during testing, not accounting for the involvement and effects of muscles that are acting when a subject moves under their own muscular force while in a weight-bearing stance further adds to this variability by introducing such inherently variable factors such as the subject's muscle strength, level of pain, involuntary contraction of opposing muscle groups, and neuro-muscular co-ordination. Taken together, all of these sources of variability serve to confound diagnostic conclusions based on comparative analyses by making the ranges of "normal" and those of "abnormal" difficult to distinguish from one another other in a statistically significant way. Such an inability to distinguish between "normal" and "unhealthy" subjects based on a specific diagnostic measurement renders such a measurement diagnostically useless, as has been the case heretofore in the prior art which has focused on measurements of uncontrolled joint motion measured in subjects in weight-bearing postures and moving their joints through the power of their own muscles and in an uncontrolled fashion.

U.S. Patent No. US 2004-0172145 A1 discloses a tilting table capable of some movement to keep an iso-center at a fixed position. U.S. Patent Publication No.: US 2006-0185091 A1 describes a multi-articulated tilting table which positions and supports a subject during examination and treatment. U.S. Pat. Publication No. US 2005-0259794 A1 to Breen discloses a device for controlling joint motion and minimizing the effects of muscle involvement in the joint motion being studied. This device minimizes variability among joint motion measurements across wide populations of subjects. As a result, comparative analyses of such measurements can be performed to determine statistical differences between the motion of "normal" and "unhealthy" subjects which in turn can provide a basis for determining the statistical confidence with which any given subject could be considered "normal" or "unhealthy" based solely on joint motion measurements.

U.S. Pat. No. 5,505,208 to Toomin et al. developed a method for measuring muscle dysfunction by means of collecting muscle activity measurements using electrodes in a pattern across a subject's back while having the subject perform a series of poses where measurements are made at static periods within the movement. These electromyographical readings of "unhealthy" subjects were then compared to those of a "normal" population so as to be able to identify those subjects with abnormal readings, however does not provide for a method to report the results as a degree of departure from an ideal reading, instead can only say whether the reading is "abnormal". U.S. Pat. No. 6,280,395 added an additional advantage to this method for determining muscle dysfunction by using the same method, yet adding the ability to better normalize the data by employing a more accurate reading of the thickness of the adipose tissue and other general characteristics that might introduce variability into the readings, as well as the ability to quantify how abnormal a subject's electromyographical reading is as compared to a "normal" population.

Neither method controls or measures the movements of the subjects while they are performing the different poses while electrical readings are being recorded. As such, variability is introduced because of differences between subjects based on their muscle strength, level or pain, ability to perform the motion pattern, and other factors. These methods also do not enable determining which type of muscle group, motive muscles or weight-bearing muscles, or which combination of muscle groups could be responsible for any observed abnormal electromyographic measurements.

Joint muscle activity has been evaluated using electromyography in combination with some type method or device to track the surface motion of the joint. In one study, visual landmarks were used to help the subject more consistently reproduce a tested motion so as to standardize the joint motion and eliminate variability. (Lariviere, C 2000) However, visual landmarking methods to not yield as "standardized" a motion as can be achieved with motion that is mechanically controlled, and measurements of the motion of internal joint structures based on surface motion measurements are too variable to be of significant clinical utility.

Another study used electromyography in conjunction with the use of a goniometer, a device that measures the surface motion of external body parts so as to link the muscle activity signals with precise surface motion measurements. (Kaigle et al. (1998) Journal of Spinal Disorders 11(2): 163-174). This method however does not take into consideration the motion of internal joint structures such that a determination as to the specific cause of joint dysfunction cannot be evaluated.

Electromyographic measurements taken during weight-bearing joint motion, with simultaneous recording of the motion of the body part using goniometers and also with simultaneous recordings of the motion of internal joint structures through the tracking of surgically-implanted metal markers, has been used to correlate muscle activity with the motion of joints and internal joint structures (Kaigle, supra). However this approach studied joint motion that was uncontrolled and required an invasive surgical procedure to place the metal markers, and thus were neither useful nor feasible for clinical diagnostic application.

Electromyography has also been used in conjunction with a device that provides transient force perturbation so as to observe whether there is a difference between subjects with low back pain and those without low back pain to determine how their muscles respond to such a force. (Stokes, Fox et al. 2006) The objective was to determine whether there is an altered muscle activation pattern when using a ramped effort. This approach however does not address the issue of which discrete muscle group or groups might account for the difference between activation patterns in subjects with joint dysfunctions and those without. Furthermore, this method does not take into consideration the internal structural joint motions and thus provides an incomplete set of information upon which to draw diagnostic conclusions.

None of the approaches contemplated in the prior art has provided useful, valid, conclusive, and relevant diagnostic results as to the potential presence of joint motion and muscle dysfunctions in a way that controls, standardizes, and measures the tested motion and is clinically practicable and thus potentially able to be integrated into the standard treatment practice for addressing joint problems and performance issues.

What is therefore needed is an apparatus and process for using the apparatus that solves the previously-identified issues, thus providing the clinician and medical device researcher with valuable diagnostic data.

SUMMARY OF THE INVENTION

An aspect of the invention is directed to an apparatus adapted and configured to cause and control joint motion of a patient. The apparatus comprises: a base positioned in a first base plane; a fixable platform adapted and configured to engage the base at an attachment mechanism, the fixable platform having a first position in a first fixable platform plane and fixably adjustable to a second position; a dynamic platform having a first position in a first dynamic platform plane, adjustable to a second position and selectively rotatable about an axis; and a coupling member adapted and configured to connect the fixable platform to the dynamic platform or the base. Furthermore the apparatus can be adapted and configured to engage a medical diagnostic device configured to capture data on the subject. Medical diagnostic devices typically include, for example, any device having a sensor adapted and configured to capture data from the subject (patient). For example, X-ray scanners, X-ray tubes with image intensifier tube, magnetic resonance scanners, infrared cameras, computed tomography scanners, ultrasound scanners, electromyography sensor units, digital camera and cameras, and electromyography sensor unit with sensors attached to the subject. The apparatus can be adapted and configured such that the medical diagnostic device detachably connects to the apparatus.

A variety of configurations of the apparatus or devices of the invention are also contemplated. For example, the apparatus can further comprise a lock for locking a position of the plane of the dynamic platform relative to the base and/or relative to the static platform. Additionally, an actuator can be provided that is coupled to the dynamic platform, wherein the actuator applies force on the dynamic platform. Such an actuator can comprise an emergency actuator stop button wherein the actuator can be stopped from applying force on the dynamic platform by activation of the emergency actuator stop button, e.g. by actuation by the patient or an operator. In some embodiments, a lock can be provided for locking a position of the static platform in at least one position relative to the base.

The apparatus can be configured such that a first plane of the base is in one of a horizontal plane or a vertical plane. The fixable platform can be adapted and configured such that it is actuated by a user. Additionally, the dynamic platform can also be configured such that it is actuated by a user. The diagnostic device can be connected to the base or the static platform in some embodiments. Additionally, the base can function as a support frame. The dynamic platform in the apparatus can further be adapted and configured to move automatically, semi-automatically, or manually. Additionally, one or more radiopaque markers can be provided that are positioned within an imaging field of the apparatus such that the markers enable the images taken of the subject to be marked real-time (e.g., at the time of image capture) with the relative location of the anatomy relative to the movement). A stabilization member adapted and configured to support the base can also be provided for device configurations that are vertically configured.

In another aspect of the invention, a process for capturing data and controlling skeletal joint motion of a subject is provided. The process comprises: providing an apparatus adapted and configured to selectively cause and control joint motion of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to a second position and selectively rotatable about an axis, and a coupling member adapted and configured to connect the fixable platform to the dynamic platform or the base; positioning the subject in a first position such that a first body part of the subject is at least partially positioned adjacent the static platform, and a second body part of the subject is at least partially positioned adjacent the motion platform; capturing, with a medical diagnostic device, a first diagnostic data from the subject and the apparatus; repositioning the apparatus such that the subject is placed in a second position different from the first position; and capturing, with the medical diagnostic device, second diagnostic data from the subject and the apparatus in the second position. Data capturing steps can further comprise use of a medical diagnostic device, such as X-ray scanners, X-ray tube with image intensifier tubes, magnetic resonance scanners, infrared cameras, computed tomography scanners, ultrasound scanners, electromyography sensor units, digital cameras and cameras. Where the electromyography sensor units are used, the data capturing steps would further comprise attaching sensors attached to the subject. In another aspect of the invention, the process includes obtaining diagnostic data from the subject by capturing data from at least one sensor. Additionally, in some instances it may be appropriate to administer a pharmaceutically active substance to the subject prior to capturing the first diagnostic data. Pharmaceutically active substances would be known to those skilled in the art and include, for example, opioid and non-opioid (such as fentanyl) substances, muscle relaxant drugs, such as baclofen, carisoprodol, chlorphenesin, chloroxazone, cyclobenzaprine, dantrolone, diazepam, metaxalone, methcarbamol and orphenadrine.

In still another aspect of the invention, a process for capturing data and controlling a skeletal joint motion of a subject is provided. The process comprises: providing an apparatus adapted and configured to selectively cause and control joint motion of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to a second position and selectively rotatable about an axis, and a coupling member adapted and configured to connect the fixable platform to the dynamic platform or the base; selecting, on the subject, a target skeletal joint for examination; attaching at least one surface electromyography sensor to the subject in adjacent the target skeletal joint; positioning the subject in a first position such that a first body part is at least partially adjacent the static platform, and second body part is at least partially adjacent the motion platform; moving the target skeletal joint from the first position to a second position different from the first position; and capturing data from the sensor while the apparatus and the target skeletal joint are in motion. In some embodiments, the process can further comprise applying a pre-determined constant resistive load force to the particular skeletal joint while the particular skeletal joint selected for examination is moving. Additionally, a pharmaceutically active substance can be administered to the subject prior to capturing data. Pharmaceutically active substances would be known to those skilled in the art and include, for example, opioid and non-opioid (such as fentanyl) substances, muscle relaxant drugs, such as baclofen, carisoprodol, chlorphenesin, chloroxazone, cyclobenzaprine, dantrolone, diazepam, metaxalone, methcarbamol and orphenadrine. Typically, the medical diagnostic devices are any devices that have a sensor capable of detecting information from a subject, including, for example, X-ray scanner, X-ray tube with image intensifier tube, magnetic resonance scanner, infrared camera, computed tomography scanner, ultrasound scanner, and digital camera and camera. In some embodiments of the process, the step of capturing data from the sensor is performed concurrently with the step of capturing data using the medical diagnostic device.

Yet another aspect of the invention is directed to an apparatus adapted and configured to detect soft tissue injury in a patient comprising: a base positioned in a first base plane; a fixable platform adapted and configured to engage the base at an attachment mechanism, the fixable platform having a first position in a first fixable platform plane and fixably adjustable to a second position; a dynamic platform having a first position in a first dynamic platform plane, adjustable to a second position and selectively rotatable about an axis; a coupling member adapted and configured to connect the fixable platform to the dynamic platform in a lockable arrangement in at least one plane; and one or more electromyography sensors adapted and configured to contact the patient at a target area, wherein the apparatus is adapted and configured to engage a medical diagnostic device configured to capture data on the subject from at least the electromyography sensor. In some embodiments of the invention, the medical diagnostic device is, for example, an X-ray scanner, X-ray tube with image intensifier tube, magnetic resonance scanner, infrared camera, computed tomography scanner, ultrasound scanner, electromyography sensor unit, digital camera and camera. The medical diagnostic device can be connected or detachably connected and further can be adapted and configured to comprise at least one sensor for capturing data. Additionally, a lock for locking a position of the dynamic platform in at least one position relative to the base may be provided. In some embodiments, an actuator can be provided that is coupled to the dynamic platform and which is adapted and configured to apply force on the dynamic platform. An emergency actuator stop button can also be provided in some instances wherein the actuator can be stopped from applying force on the dynamic platform by activation of the emergency actuator stop button. The actuator can be actuated by the patient or an operator. In other embodiments, a lock is provided for locking a position of the status platform in at least one position relative to the base. Additionally, the first plane of the base can be, for example, one of horizontal or vertical. Additionally, the fixable platform can also be adapted and configured to be actuated by a user. In some instances, the diagnostic device is connected to the base or the static platform; additionally, the base can also be adapted and configured to function as a support frame.

The invention also includes a method for detecting soft tissue injury in a subject. Soft tissue injury is detected by: providing an apparatus adapted and configured to selectively cause and control joint motion of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to a second position and selectively rotatable about an axis, and a coupling member adapted and configured to connect the fixable platform to the dynamic platform or the base; selecting, on the subject, a target skeletal joint for examination; attaching at least one surface electromyography sensor to the subject in near proximity to the target skeletal joint; positioning the subject in a first position such that a first body part is at least partially adjacent the static platform, and second body part is at least partially adjacent the motion platform; manually moving the target skeletal joint from the first position to a second position different from the first position; capturing data from the sensor while the apparatus and the target skeletal joint are in manual motion; automatically moving the target skeletal joint from the first position to the second position different from the first position; capturing data from the sensors while the apparatus and the target skeletal joint are in automatic motion; and evaluating the data to determine whether a soft tissue injury exists. Additionally, the method can include the step of comparing sensor data captured while the apparatus and target skeletal joint are in manual motion to sensor data captured while the apparatus and target skeletal joint are in automatic motion and/or applying a pre-determined constant resistive load force to the particular skeletal joint while the particular skeletal joint selected for examination is moving.

Still another aspect of the invention is directed to a method for assessing a subject's suitability for an orthopedic procedure. The method comprises: providing an apparatus adapted and configured to selectively cause and control joint motion of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to a second position and selectively rotatable about an axis, and a coupling member adapted and configured to connect the fixable platform to the dynamic platform or the base; selecting, on the subject, a target skeletal joint for examination; attaching at least one surface electromyography sensor to the subject in near proximity to the target skeletal joint; positioning the subject in a first position such that a first body part is at least partially adjacent the static platform, and second body part is at least partially adjacent the motion platform; manually moving the target skeletal joint from the first position to a second position different from the first position; capturing data from the sensor while the apparatus and the target skeletal joint are in manual motion; automatically moving the target skeletal joint from the first position to the second position different from the first position; capturing data from the sensors while the apparatus and the target skeletal joint are in automatic motion; and evaluating the data to determine the subject's suitability for an orthopedic procedure. The method can also include the steps of comparing sensor data captured while the apparatus and target skeletal joint are in manual motion to sensor data captured while the apparatus and target skeletal joint are in automatic motion and/or applying a pre-determined constant resistive load force to the particular skeletal joint while the particular skeletal joint selected for examination is moving.

An aspect of the invention is directed to a method for assessing a performance of an orthopedic procedure in a subject. The method comprises: performing an orthopedic procedure on the subject; providing an apparatus adapted and configured to selectively cause and control joint motion of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to a second position and selectively rotatable about an axis, and a coupling member adapted and configured to connect the fixable platform to the dynamic platform or the base; selecting, on the subject, a target skeletal joint for examination; attaching at least one surface electromyography sensor to the subject in near proximity to the target skeletal joint; positioning the subject in a first position such that a first body part is at least partially adjacent the static platform, and second body part is at least partially adjacent the motion platform; manually moving the target skeletal joint from the first position to a second position different from the first position; capturing data from the sensor while the apparatus and the target skeletal joint are in manual motion; automatically moving the target skeletal joint from the first position to the second position different from the first position; capturing data from the sensors while the apparatus and the target skeletal joint are in automatic motion; and determining a performance of an orthopedic procedure. The method can also include the step of comparing sensor data captured while the apparatus and target skeletal joint are in manual motion to sensor data captured while the apparatus and target skeletal joint are in automatic motion and/or applying a pre-determined constant resistive load force to the particular skeletal joint while the particular skeletal joint selected for examination is moving.

Another aspect of the invention is directed to a method for assessing a clinical condition in a subject. The method comprises: providing an apparatus adapted and configured to selectively cause and control joint motion of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to a second position and selectively rotatable about an axis, and a coupling member adapted and configured to connect the fixable platform to the dynamic platform or the base; selecting, on the subject, a target skeletal joint for examination; positioning the subject in a first position such that a first body part is at least partially adjacent the static platform, and second body part is at least partially adjacent the motion platform; moving the target skeletal joint from the first position to a second position different from the first position; capturing data from the sensor while the apparatus and the target skeletal joint are in motion; analyzing the captured data; and generating a data output having less than 5° error. The method can further comprise the step of comparing sensor data captured while the apparatus and target skeletal joint are in manual motion to sensor data captured while the apparatus and target skeletal joint are in automatic motion and/or applying a pre-determined constant resistive load force to the particular skeletal joint while the particular skeletal joint selected for examination is moving. Still another aspect of the method, can include comparing the captured data to a database of data captured from a population of patients engaging in a movement of a target skeletal joint from a first position to a second position different from the first position.

The present invention also contemplates a method to produce useful, novel, orthopedic diagnostic results related to joint motion, based on the quantitative interpretation of moving orthopedic diagnostic images, coupled with the control over and measurement of other joint motion, force, and electromyographic parameters, such as by use of the motion and inertial force sensor unit 41 in FIG. 6 and the electromyography sensors noted above. Such orthopedic diagnostic results are produced by the present invention through the novel combination use of: (1) an apparatus for controlling, standardizing, and measuring weight-bearing and non-weight-bearing motion of the joints of imaging subjects, with the optional and additional capability of providing force for, adding resistive loads to, measuring the force of, and positioning the joint for rotation through differing planes of rotation of said joint motion; (2) a diagnostic imaging machine capable of producing digital moving images of joint motion; (3) electromyography investigations into muscle involvement associated with specific types of joint motion; (4) approved and commercially-available pain and muscle relaxant drugs utilized during the diagnostic testing event for purely diagnostic and not therapeutic purposes; (5) digital image processing and analysis methods; and (6) investigational data produced through the use of the present invention in controlled clinical trials and applied to generate clinically useful diagnostic results from the physiological measurements afforded by the present invention.

INCORPORATION BY REFERENCE

All publications, patents and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7C-E illustrate a device from different views;

FIGS. 12A and 12B show side view block diagrams of Design 2 of the vertically configured motion control device in the "default" and "angled" configurations, respectively, according to one embodiment of the present invention;

FIGS. 14A, 14B, 14C, and 14D illustrate the functionalities of Design 1 (from FIGS. 9A, 9B, 10A, 10B, and 10C) and Design 2 (from FIGS. 11A, 11B, 12A, and 12B) of the vertically configured motion control device, according to one embodiment of the present invention;

FIGS. 16A-B illustrate a subject bending through a range of motion with a plurality if images being sampled during the continuous motion which achieves an output having minimal noise;

DETAILED DESCRIPTION OF THE INVENTION

Figure 1A:
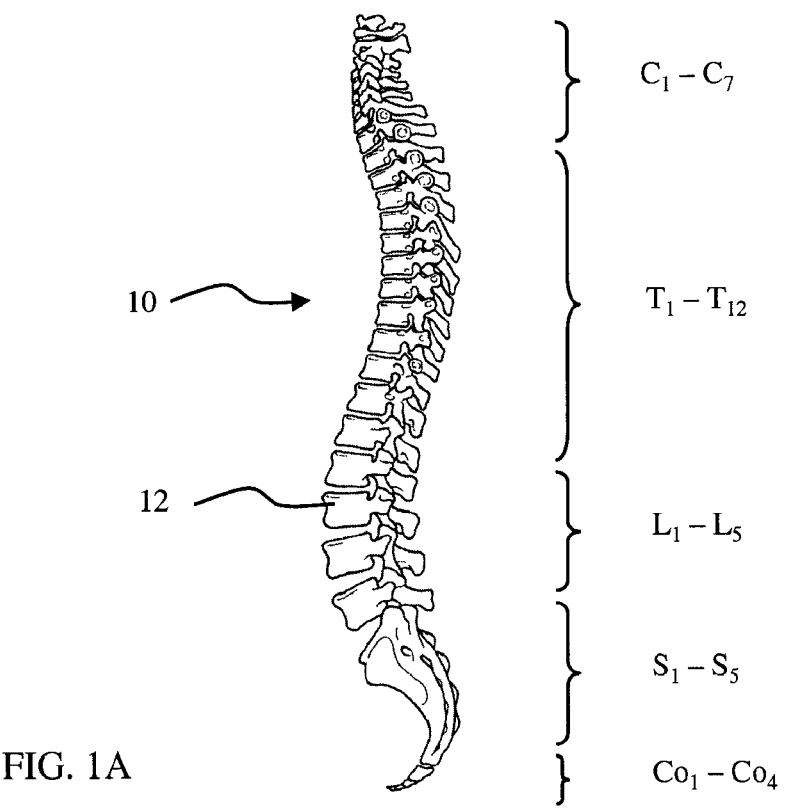
FIG. 1A is a lateral view of a normal human spinal column.

FIG. 1 illustrates the human spinal column 10 which is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Co4.

Figure 1B:
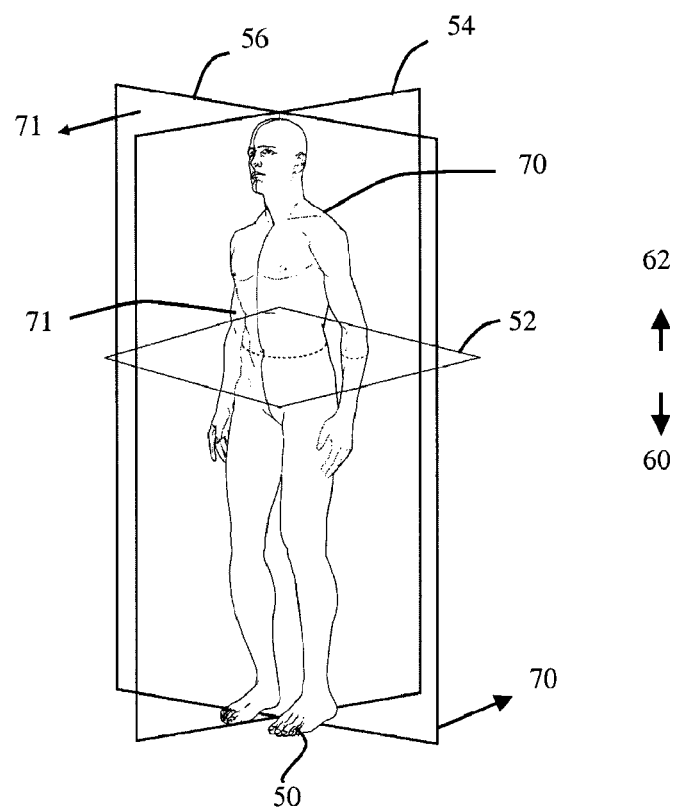
FIG. 1B is illustrates a human body with the planes of the body identified.

In order to understand the configurability, adaptability, and operational aspects of the invention disclosed herein, it is helpful to understand the anatomical references of the body 50 with respect to which the position and operation of the devices, and components thereof, are described. As shown in FIG. 1B, there are three anatomical planes generally used in anatomy to describe the human body and structure within the human body: the axial plane 52, the sagittal plane 54 and the coronal plane 56. Additionally, devices and the operation of devices and tools may be better understood with respect to the caudad 60 direction and/or the cephalad direction 62. Devices and tools can be positioned dorsally 70 (or posteriorly) such that the placement or operation of the device is toward the back or rear of the body. Alternatively, devices can be positioned ventrally 72 (or anteriorly) such that the placement or operation of the device is toward the front of the body. Various embodiments of the devices, systems and tools of the present invention may be configurable and variable with respect to a single anatomical plane or with respect to two or more anatomical planes. For example, a subject or a feature of the device may be described as lying within and having adaptability or operability in relation to a single plane. A device may be positioned in a desired location relative to a sagittal plane and may be moveable between a number of adaptable positions or within a range of positions.

For purposes of illustration, the devices and methods of the invention are described below with reference to the spine of the human body. However, as will be appreciation by those skilled in the art, the devices and methods can be employed to address any effected bone or joint, including, for example, the hip, the knee, the ankle, the wrist, the elbow, and the shoulder. Additionally, the devices and methods can also be employed with any mammal.

Figure 2A:
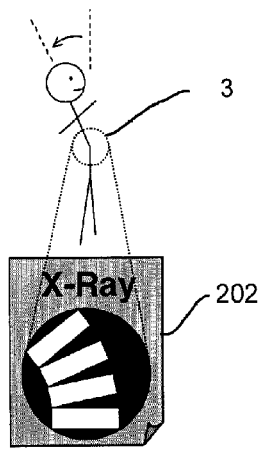
FIG. 2A-C illustrate a subject bending through a range of spinal flexion and extension motion with a corresponding x-ray taken at each position, as currently practiced in the art.
Figure 2B:
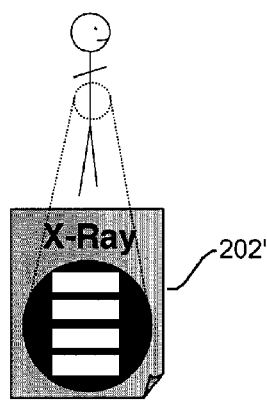
Figure 2C:
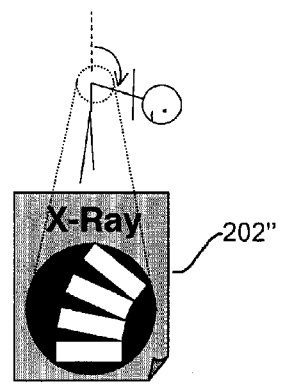
Figure 2D:
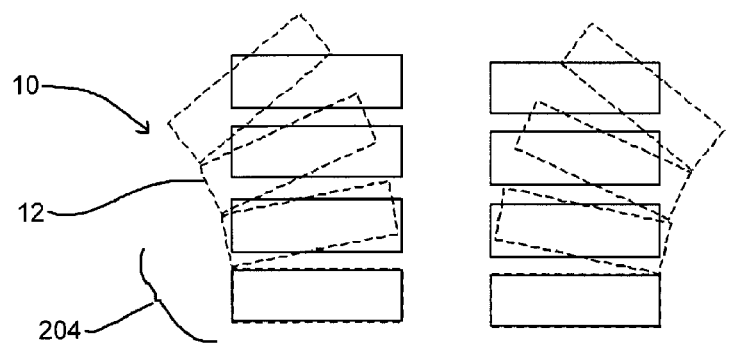
FIG. 2D illustrates stacked vertebral bodies of a spine moving through the range of motion illustrates in FIGS. 2A-C.
Figure 2E:
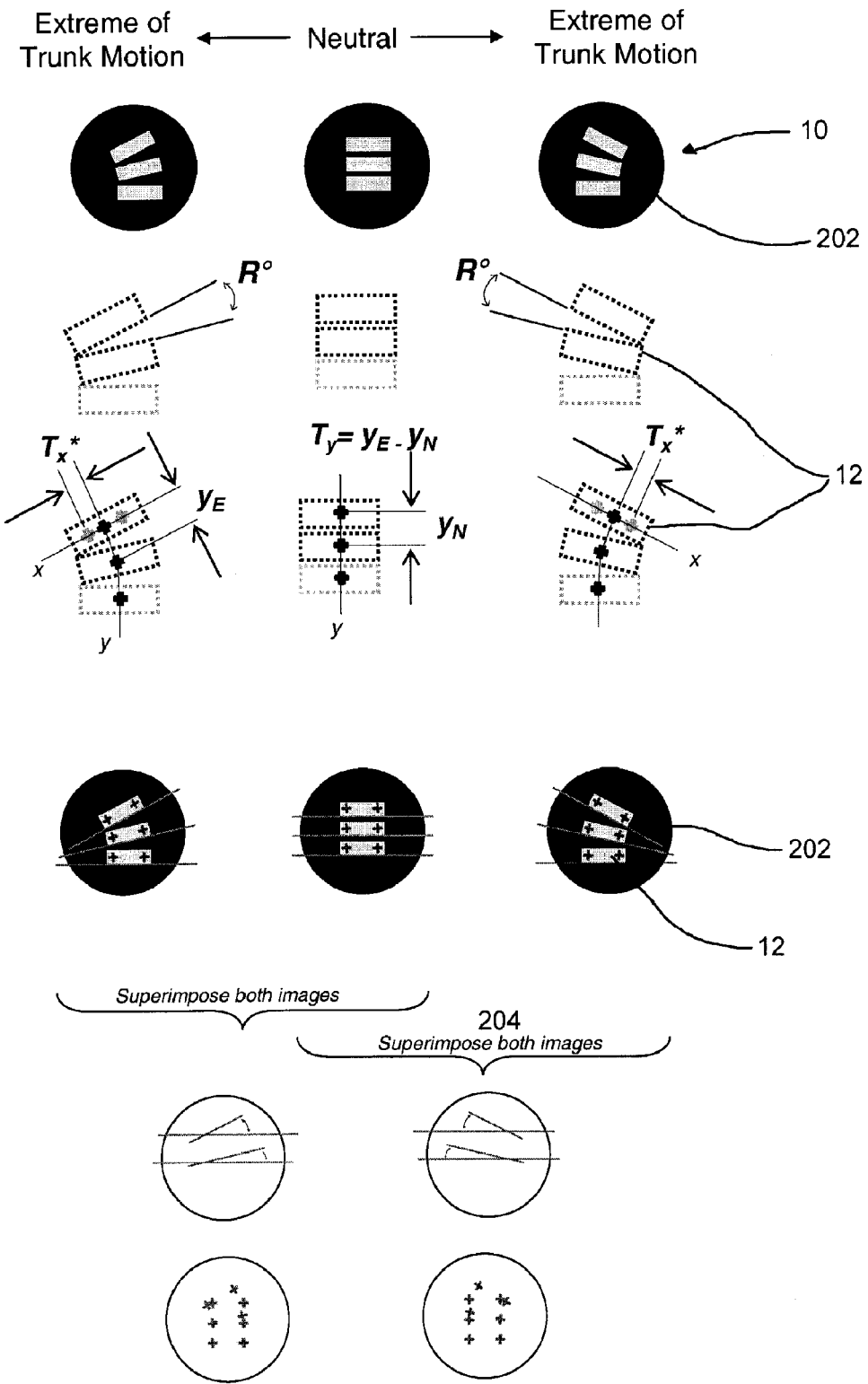
FIG. 2E illustrates a process for interpreting radiographic images in traditional spinal kinematic studies.
Figure 2F:
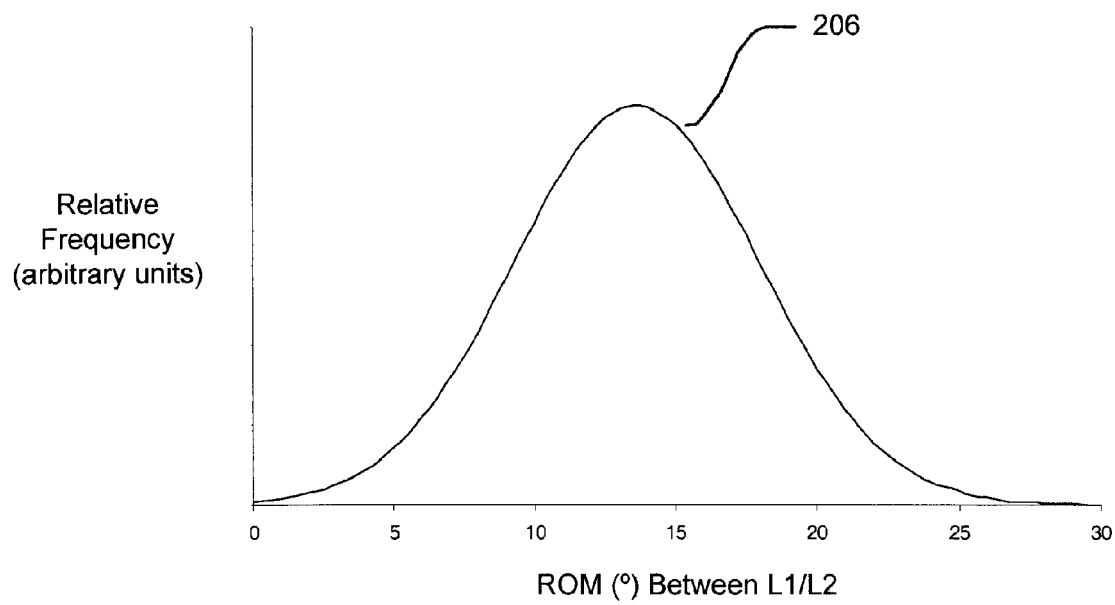
FIG. 2F illustrates a normative frequency distribution curve of range of motion measurements taken from a population of normal subjects with healthy spines using currently available techniques that have been shown to be interpretable to a level of precision of no less than +5°.
Figure 2F:
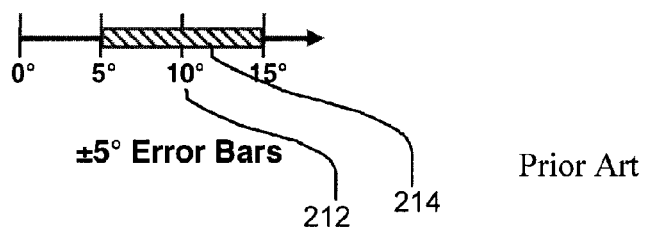

FIGS. 2A-C illustrate a subject 3 bending through a range of motion with a corresponding x-ray 202 taken at each position, as currently practiced in the art. Typically a subject 3 is instructed to stand in front of a device adapted to capture an x-ray image and then bend to a first position and then to a second position. An x-ray image 202, 202', 202" is taken at each of these positions. Thereafter two x-rays images, e.g., 202, 202', are superimposed, e.g. as illustrated in FIG. 2D, to show the vertebral bodies 12 stacked and crudely moving through the range of motion. As illustrated in FIG. 2E this process for interpreting radiographic images in traditional spinal kinematic studies has a variety of manual steps which include using a protractor to draw on the image to measure how much movement has occurred. These steps are also sometimes executed with the assistance of a computer, in which case the manual steps are done with a mouse or other manually-operated computer input device. The results achieved using these manual methods, as shown in FIG. 2F, are inherently subject to a high degree of inter-observer and intra-observer variability as different observers utilize different techniques to landmark the images and derive measurements. Further, the uncontrolled bending process represented in FIGS. 2A-C is responsible for introducing a high degree of inter-subject and intra-subject variability into these measurements as different subjects are capable of bending to differing positions. As will be appreciated by those skilled in the art, any medical image-derived quantitative measurements of joint motion 204 will also contain variability that is due to out of plane and geometric distortions inherent to medical imaging. Therefore, image based measurements for range of motion would exhibit observable measurements that fall within a distribution of variability about the actual motion. Combining these three sources of variability, it is well established that in the clinical utilization of image-derived measurements of intervertebral range of motion, it is not feasible to interpret such measurements as having error of any better than ±5°. FIG. 2F shows the mean L1/L2 rotational ROM taken from a normative population of pain free subjects is about 10° of rotation. Accounting for the +5° of error in this measurement, the error bars on this measurement 206 are about 50% of the underlying mean measurement value.

Figure 2G:
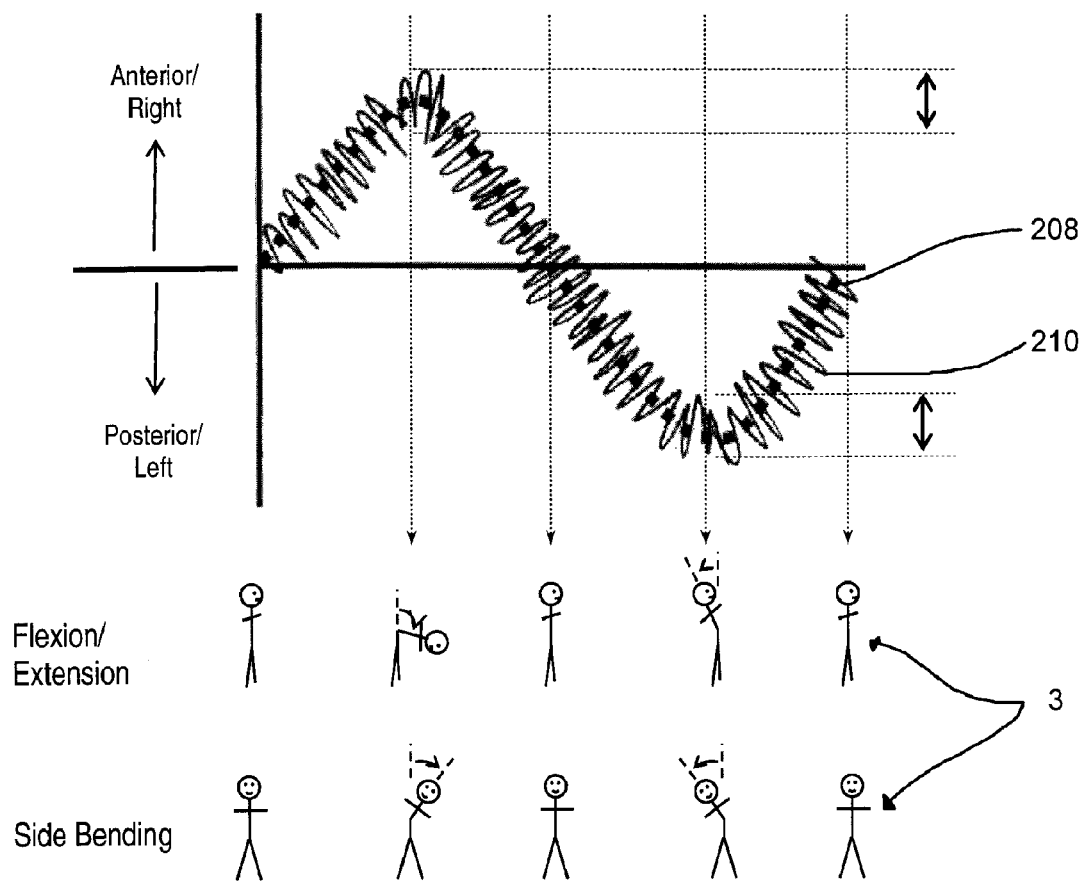
FIG. 2G is an illustrative inter-vertebral motion curve, corresponding to flexion/extension or side-bending, along with an illustrative representation of error in observed measurement.

As illustrated in FIG. 2G an inter-vertebral motion curve created taking measurements using currently practiced techniques, corresponding to flexion/extension or side-bending, would have "noise" 212 in the observed motion 210 relative to the actual motion 208. FIG. 2H illustrates an intervertebral motion curve for the L4-L5 joint of a healthy subject side bending.

Figure 3A:
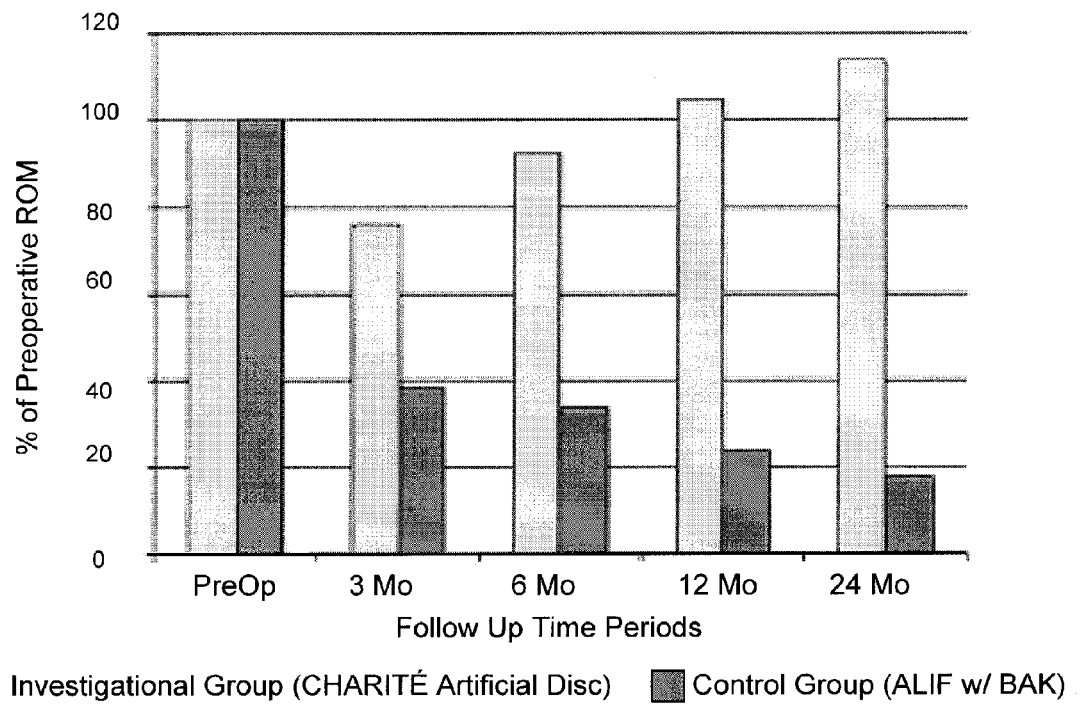
FIG. 3A is a bar chart illustrating the a pre-to-post-operative comparison of intervertebral range of motion (ROM) for an investigational group receiving the CHARITÉ spinal implant as compared to a group receiving solid fusion, which is the current standard of care.

FIG. 3A is a bar chart illustrating the percent of preoperative range of motion (ROM) for an investigational group receiving the Charite™ spinal implant as compared to a control group with anterior lumbar interbody fusion. McAfee, et al. "A Prospective, Randomized, Multicenter Food and Drug Administration Investigational Device Exemption Study of Lumbar Total Disc Replacement With the Charite™ Artificial Disc Versus Lumbar Fusion, Part II," Spine 2005 30:14 (1576-83). The conclusion of the study was that preoperative range of motion in flexion/extension was restored and maintained in patients receiving total disc replacement. However, the observable error measurement inherent in current diagnostic techniques as illustrated in FIG. 2G potentially impact the conclusions of the study.

Figure 3B:
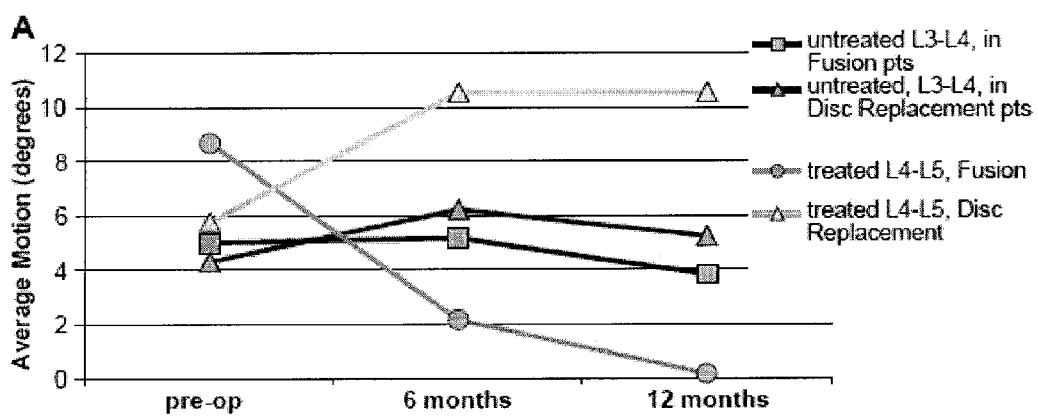
FIG. 3B illustrates the trial results of PRODISC II showing L4/L5 level sagittal motion data for disc replacement.

FIG. 3B illustrates the trial results of Prodisc II showing L4/L5 level sagittal motion data for disc replacement. Delamarter, RB, et al. "Clinical Results of ProDisc-II Lumbar Total Disc Replacement: Report from the United States Clinical Trial," Ortho. Clin. N. Am. 36 (2005) pp. 301-13. The Delamarter study concluded that the sagittal motion data suggests that disc replacements not only preserve motion but also increase or restore motion. Observable error inherent in current diagnostic techniques could also impact the findings of the study.

Although ROM, if it were more precise, could yield very significant clinical and biomechanical insights into the function of dynamic stabilization device, the inherent error tolerances of ROM measurements are sometimes overlooked because of their difficulty to measure. Such an oversight could potentially erode the validity of conclusions supported by an analysis of ROM data from clinical trials.

I. SYSTEMS

Figure 4:
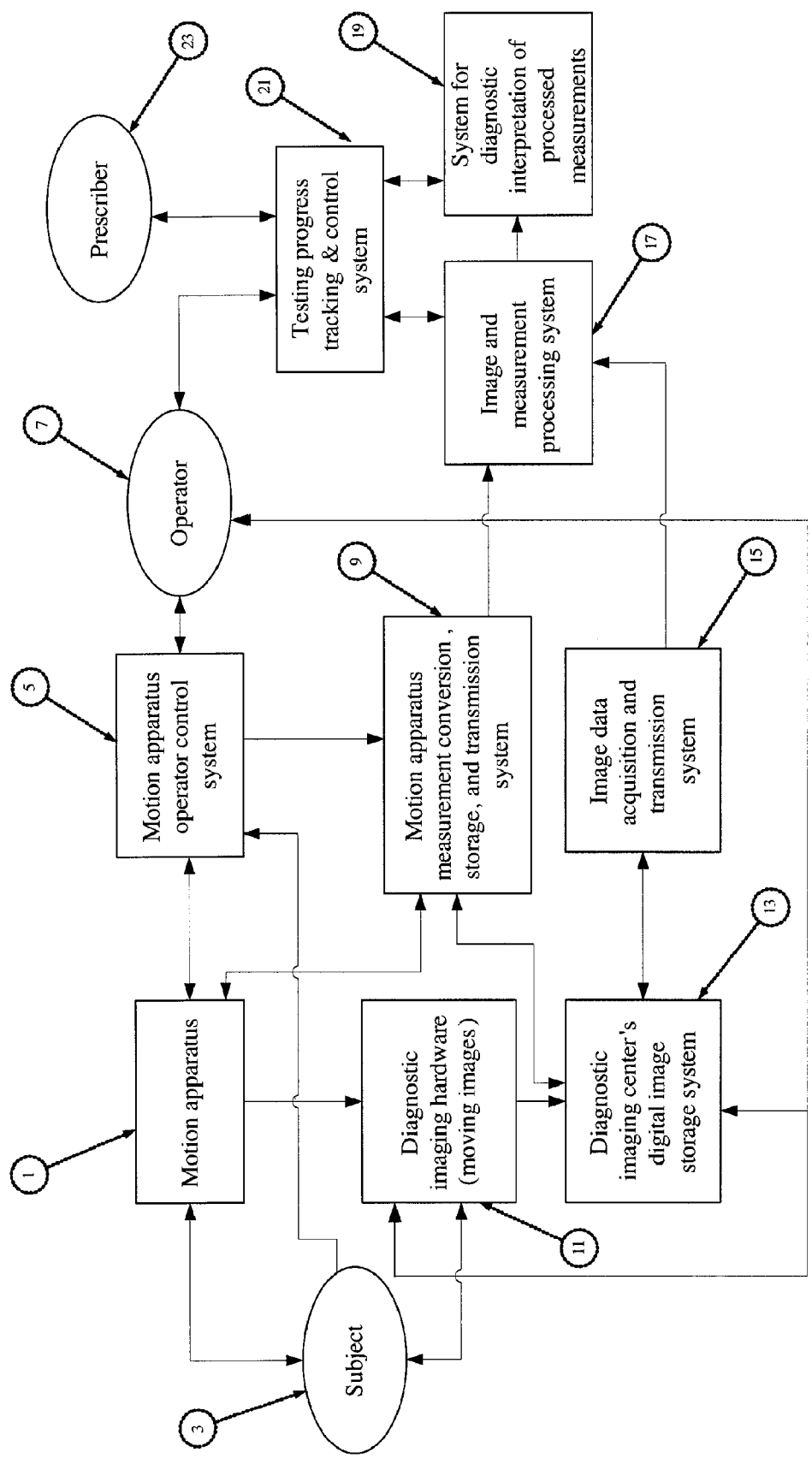
FIG. 4 is a block diagram that shows the relationship between a motion apparatus of the invention and a control system, the various other systems that are required to execute a complete diagnostic test, and three participants involved with diagnostic testing, which can include the subject, the operator, and the prescriber, according to one embodiment of the present invention.

FIG. 4 illustrates a system comprising an apparatus 1 adapted and configured to interact with one another and also with one or more of three participants involved in a testing episode: the subject 3, the operator 7, and the prescriber 23. The motion control apparatus 1 can be any of the devices described or enabled herein. As will be appreciated by those skilled in the art, connections between and among the motion control apparatus 1 from FIG. 4 and other elements within the system are applicable to any of the devices enabled herein.

The motion control apparatus 1 is a configurable apparatus 1 that can be adapted and configured to physically attach to the subject 3, e.g., with the use of restraints, and may also be adapted and configured to physically attach to the diagnostic imaging hardware 11 or floor in such a way the joint rotation of the subject 3 through the specific arc of rotation that is being studied can be captured by moving images of diagnostic imaging hardware 11, and such joint rotation and associated muscle forces can also simultaneously be measured and also possibly either controlled, acted upon, or some combination thereof by the motion apparatus 1. In addition, the motion apparatus 1 may also physically engage a subject 3, e.g, with electrodes and/or other electronic devices and sensors for the purpose of collecting images, electromyography and/or other types of sensor based diagnostic measurements.

The motion apparatus 1 is linked to the motion apparatus operator control system 5, such that electronic instructions can be transmitted from the operator control system to the motion apparatus, and so that testing measurement signals can be transmitted from the motion apparatus to the operator control system. This transmission is accomplished either through a direct wire-based electronic connection between the two components or through a wireless connection. The motion apparatus operator control system 5 is capable of receiving input from the operator 7 for the purpose of starting, stopping, monitoring, and controlling the operation of the motion apparatus 1, according to one embodiment of the present invention. In addition, the motion apparatus operator control system 5 is capable of receiving input from the subject 3 in the case that the operation of the motion control apparatus 1 needs to be stopped, e.g., on an emergency basis or for any other reason. Such input from the subject 3 is accomplished through the use of an emergency shut off button that is accessible to the subject 3.

Either or both the motion apparatus 1 and/or the motion apparatus operator control system 5 also connect(s) to the motion apparatus measurement conversion, storage, and transmission system 9 by way of an electronic transmission of measurement signals from the motion control apparatus 1, either via the motion apparatus operator control system 5 or directly from the motion control apparatus 1. Such a transmission is accomplished either through a direct wire-based connection between the two or three components or through a wireless connection. The motion apparatus measurement conversion, storage, and transmission system 9 is embodied by a system of computer hardware and software. In accordance with this embodiment, as this system receives said electronic measurement signals, it has the capability to: (1) convert analog electrical measurement signals into digital data; (2) temporarily store said digital data as well as other digital data relating to the configuration of the motion apparatus 1 during the testing episode; (3) create and temporarily store digital identifying information and other digital data that uniquely identifies the subject and that provides information required to synchronize in time the measurements from the motion apparatus with those from the imaging device and other diagnostic measurement devices 3, testing location, testing time, testing episode, and/or any other information necessary to definitively link the digital measurement data to a specific testing event; and (4) transmit said digital data to the image and measurement processing system 17 in a secure and verifiable way.

If the testing environment in which the apparatus of this invention is located has an available computer with available computing and media storage capacity and that is internet, or network, connected and located within the room or suite that the diagnostic imaging equipment is located, then the motion apparatus measurement, conversion, storage, and transmission system 9 is embodied by a peripheral piece of hardware that connects to said computer, plus software that can be adapted and configured to: (1) control the hardware, (2) control the interface of the hardware and the computer, (3) create, temporarily store, and access testing data files, (4) affect a secure and verifiable transmission of testing data to the image and measurement processing system 17, either by directly transmitting said data over the internet or, if no such internet connectivity exists, by doing so via either an intermediate transmission of the data to the diagnostic imaging center's digital image storage system 13, after which the test measurement data would be included and handled as part of the set of imaging data files associated with the testing episode, the handling of which is further described below, or alternatively by storing the data files on removable media, removing, and physically transmitting said media to the image and measurement processing system 17. The peripheral piece of hardware can also be configured to have the capability to: (1) receive analog signals and digital data from the motion control apparatus 1 and the motion apparatus operator control system 5, (2) convert said analog signals into digital data, and (3) connect to a standard computer interface, such as a serial port or USB port using standard computer hardware communication protocols, (4) transmit said digital data to the computer, and (5) be controllable by the software described directly above. If there is no such available computer within the room or suite that the diagnostic imaging equipment is located, then the apparatus measurement conversion, storage, and transmission system will also include a dedicated computer to which said hardware attaches, on which said software runs, and through which said transmission is executed.

Additionally, the diagnostic imaging hardware 11 can be any suitable imaging device such as devices capable of generating moving diagnostic images. Suitable devices include, for example, Siemens Artis-MP, Siemens Neurostar, and General Electric OEC line fluoroscopy units. The diagnostic imaging center's digital image storage system 13, can be any suitable image storage system. Image storage systems include, for example, computer controlled digital storage media device dedicated to receiving, storing, configuring, and accessing data files containing these moving images. The systems can be controlled by the operator 7, or the digital image storage system 13, and functions as the repository for the digital data files of moving diagnostic images that are generated by the diagnostic imaging hardware 11 during a testing episode. The digital image storage system 13 may be a sub-system of the diagnostic imaging hardware 11 system, or may be a separate and independent system of computer hardware and software, according to one embodiment of the present invention.

The image data acquisition and transmission system 15 can be adapted and configured to interface directly with the diagnostic image center's digital image storage system 13 such that the data files associated with a specific testing episode can be: (1) accessed such that a full and complete copy of all digital imaging files is available; (2) identified with respect to digital identifying information that uniquely identifies the subject 3, testing location, testing time, testing episode, operator, prescriber, and/or any other information necessary to definitively link the imaging data files to a specific testing event; and (3) transmitted to the image and measurement processing system 17.

The image data acquisition and transmission system 15 can also be configured to include either a software only system or a system that involves both hardware and software. The software only embodiment of the image data acquisition and transmission system 15 is utilized when there is available computer hardware and computing capacity within the diagnostic image center's digital image storage system 13 such that no additional computer hardware resources are required to affect a functionality of the image data acquisition and transmission system 15 described herein. In such a software only system, implementing the capabilities of the system can either require additional dedicated software to be installed or alternatively is possible to implement with the software resident on the diagnostic image center's digital image storage system 13. In either case, the capabilities of the software are to: (1) identify, locate, and access a complete set of all digital imaging files associated with the testing episode; a complete set of identifying data files that uniquely identifies the subject 3, testing location, testing time, testing episode, operator, prescriber 23, and/or any other information necessary to definitively link the data files to a specific testing event; and any other digital measurements or conversions related to the testing episode that may be located on the imaging center's digital image storage system 13; (2) give commands that then transmit said data files to the image and measurement processing system 17, allowing for transmission processes that include internet-based transmission as well as transmissions involving the storage of data files on removable media that are then removed from the media recording device on which they were produced and physically transmitted to the image and measurement processing system 17; and (3) allow for a confirmation of the receipt of said data files by the image and measurement processing system 17 to the transmitter of the data files. The embodiment of the image data acquisition and transmission system 15 that involves both hardware and software is utilized when there is no available computer hardware and computing capacity within the diagnostic image center's digital image storage system 13 to affect a functionality of the image data acquisition and transmission system 15 described above. In such a circumstance, the functionality of the image data acquisition and transmission system 15 is accomplished by a separate computer additional to that which would be required in the absence of the present invention, and a capability of said computer to access the media on which the test data files are stored within the diagnostic image center's digital image storage system 13 via a wireless or wire-based connection between the said media and the said separate additional computer. The above listed software functionality is installed on said computer, such that the software functionality listed above is afforded by said computer in a way identical to that which is listed above in the software only embodiment of this system.

The image and measurement processing system 17 can also be a computer hardware and software system that can operate with the assistance of a human overseer, that has the capability to receive, catalog, store, access, and process the digital data that are transmitted from the motion apparatus measurement conversion, storage, and transmission system 9 as well as from the image data acquisition and transmission system 15. In processing said digital data, the image and measurement processing system 17 has the capability to: (1) perform digital image processing to derive time-series measurement of the position of and displacement between any set of joint structures that appear on diagnostic images as they move relative to each other over consecutive frames of the moving image, (2) synchronize in time said time-series measurements with the quantitative measurements of joint motion, measured external and inertial forces, electromyography, and/or any other electronic sensor-based data that is collected, such as by use of the motion and inertial force sensor unit 41 in FIG. 6 and the electromyography sensors noted above and (3) associate with said measurements data regarding the testing episode, such as the configuration of the motion apparatus 1 as well as information that uniquely identifies the testing subject 3 and specific testing episode. The image and measurement processing system 17 has the additional capability of transmitting processed measurements to the system for diagnostic interpretation of processed measurements 19.

The system for diagnostic interpretation of processed measurements 19 can be a computerized and manual interpretation process based on the third aspect of the present invention, which is the specification of an interpretation methodology to derive diagnostic results from the use of the present invention. Said computerized and manual interpretation process is capable of receiving processed quantitative measurements from the image and measurement processing system 17 and using these measurements to produce diagnostically useful conclusions about the subject's processed measurements and presenting these conclusions to prescribers to deliver the diagnostic result, according to one embodiment of the present invention. This system for diagnostic interpretation of processed measurements 19 comprises: (1) data tables of measurement ranges across a broad population of subjects, produced and collected through controlled clinical investigations using the present invention; (2) a data collection and analysis methodology to develop and use said data tables in a way that takes into account the subjects age, sex, joint problem, or a multitude of other characteristics to determine the statistical confidence with which a specific measurement can be considered to be normal or abnormal, and if abnormal then also the statistical confidence with which said measurement can be associated with a specific type of joint functional derangement; (3) definitions, based on said data tables, for specific types of functional derangements that are defined in terms of specific quantitative ranges for specific processed measurements and specific statistical confidence levels that said ranges indicate the presence of specific types of functional derangements; (4) software to produce diagnostic result reports for prescribers that are relevant to the diagnostic objectives for which the test was prescribed, and that are useful for the purpose of adding to the diagnostic understanding of the subjects joint problems; and (5) a computerized and/or manual process for receiving processed quantitative measurements from the image and measurement processing system 17, generating diagnostic result reports for prescribers, and transmitting these result reports to the testing process tracking and control system 21.

The testing process tracking and control system 21 can be coordinated by a computerized and/or manual tracking and control process that is connected to both the image and measurement processing systems 9 and the system for diagnostic interpretation of processed measurements 19 in such a way that the process tracking and control system 21 has up-to-date information regarding the storage location and processing status of test measurements data files, processed measurement data files, and finished result reports. This testing process tracking and control system 21 manages the delivery of testing result reports to both operators 7 and prescribers 23, and is the point of contact for operators and prescribers if they should have inquiries regarding the status of specific tests as well as to collect feedback from them if they should have questions or require clarifications to or interpretations of specific results reports that they have received, according to one embodiment of the present invention.

II. MOTION CONTROL APPARATUS SELECTION

The motion control apparatus 1 from FIG. 4 can be any one or more of a set of devices (e.g., motion control devices 25, 27, 29 described below) which are developed for the purpose of being able to afford the capability to: (1) measure joint surface motion and the motion of internal joint structures; (2) measure the same joint (either the same joint across different subject, or the same joint within any given subject) in both weight-bearing (if the joint is normally a weight-bearing joint such as the spine or knee) and non-weight-bearing postures, in postures that are bent or that lie in between "full" weight-bearing and "full" non weight-bearing postures, and in the presence and absence of different types of external forces; and (3) collect additional data regarding the joint motion, such as the underlying nerve activity, muscle involvement, inertial forces, and fluid dynamics.

The motion control apparatus 1 can have a variety of configurations adapted and configured to achieve the objectives of the invention. However, as will be appreciated by those skilled in the art, variations to the configurations can be made without departing from the scope of the invention.

Figure 5:
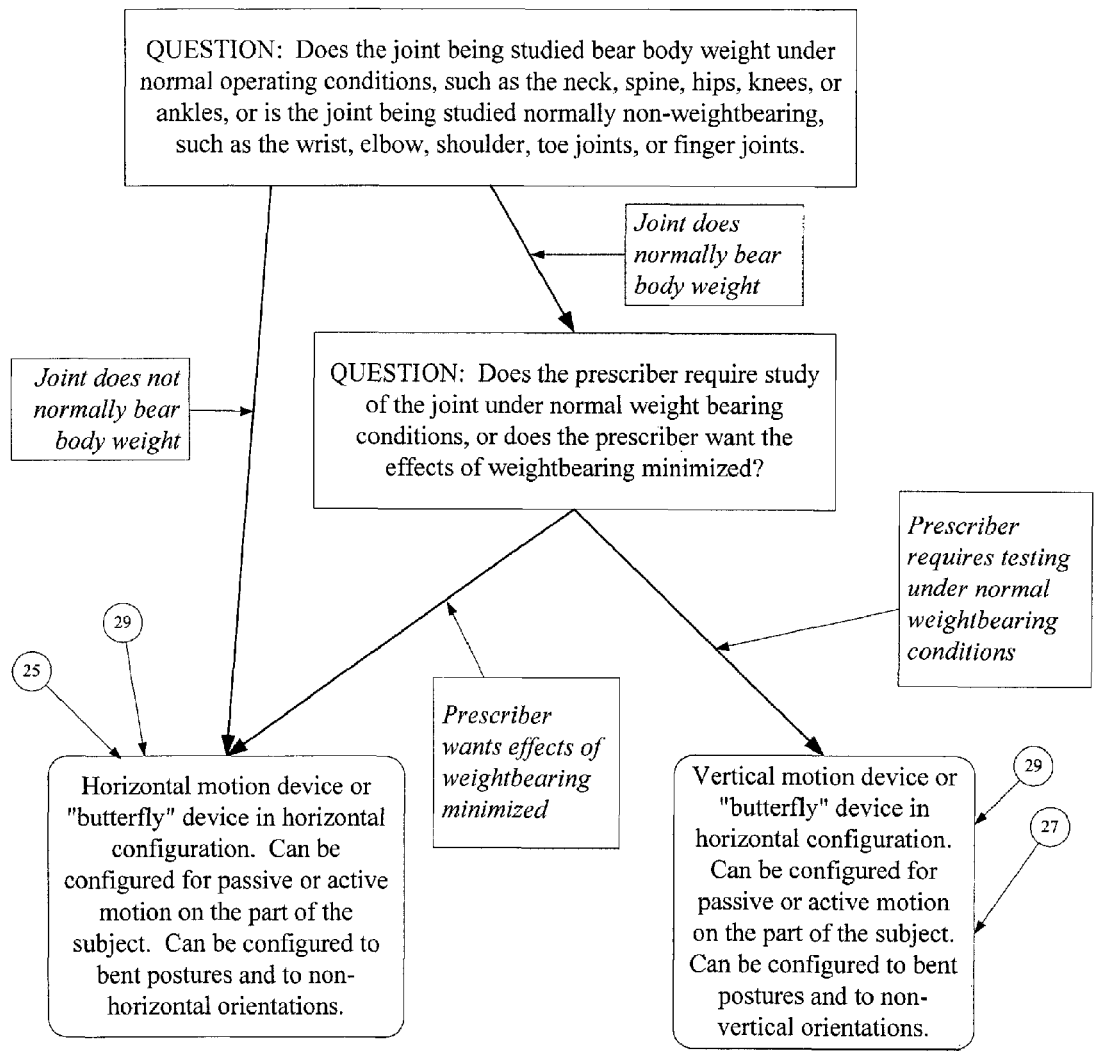
FIG. 5 shows a diagram of the decision process for determining which specific motion apparatus configuration is appropriate for any given prescribed test, according to one embodiment of the present invention.

Determining which of these devices is required for any given prescribed test can be resolved using the decision process put forward in FIG. 5. As is evident in FIG. 5, a horizontally configured motion control device 25 is appropriate for diagnostic studies of joints that either do not normally bear body weight, such as the wrist, elbow, or shoulder, or for studies of joints that do normally bear body weight such as the neck, spine, hips, or knees, but that are specifically prescribed to be studied under non-weight-bearing conditions. In contrast, a vertically configured motion control device 27 is appropriate for diagnostic studies of joints that normally bear body weight and that are prescribed to be studied under normal weight-bearing conditions. A "butterfly" motion control device 29 is appropriate for diagnostic studies of joints that are prescribed to be studied under either or both weight-bearing and/or non-weight-bearing conditions or for joint motions that are to be studied in bent postures.

For example, the horizontally configured motion control device 25 is designed to be able to accommodate any type of testing in which joint motion is being studied under non-weight-bearing conditions and can provide for controlled, standardized, and measurable motion that can either involve or not involve external forces during the motion.

III. DEVICES

Figure 6:
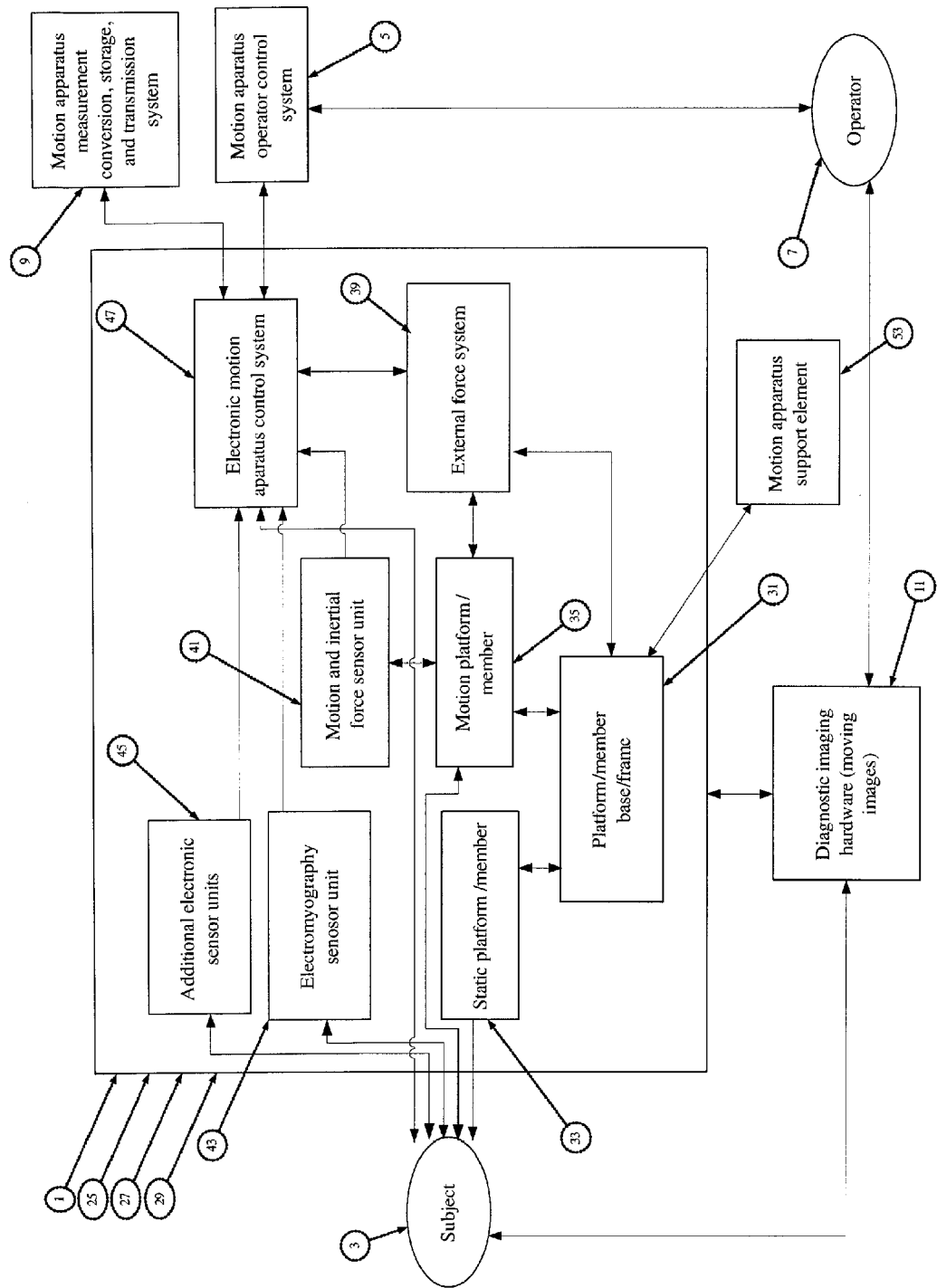
FIG. 6 shows the sub-systems that comprise both the horizontally configured motion control device and the vertically configured motion control device, and how these subsystems relate with one another and also with the subject, the operator, the motion apparatus control system, and the diagnostic imaging hardware, according to one embodiment of the present invention.

FIG. 6 is a block diagram of a motion control device 1 which is represented by the large box that contains the various listed subsystems. As will be appreciated by those of skill in the art, the motion control device 1, can also be a horizontally configured motion control device 25, a vertically configured motion control device 27 or a butterfly configured device 29.

The diagnostic imaging hardware 11 contains a field of imaging, which is a physical space in which objects imaged by the hardware must be located during the imaging process to produce images. The field of imaging can contain a posture assistance device such as a table, bed, chair, or other device intended to bear all or some of the subject's weight and to provide physical support to a specific type of posture. Alternatively, the field of imaging can contain no such devices if the subject can be situated directly onto the floor and/or the motion control device 1 and does not require the use of an additional device to bear weight and/or support specific postures, according to one embodiment of the present invention. The motion control device 1, or sub-systems therein, occupy part or the entire field of imaging and is physically connected and supported either by resting on the floor itself, or by being physically and immovably attached to the imaging equipment or to one of the above-mentioned posture-assistance devices within the field of imaging. All parts of the horizontally configured motion control device 1 that are located within the field of imaging are constructed of materials that are either radiolucent in the case of use with videoflouroscopic and moving CT imaging systems, or alternatively compatible with MRI images in the case of a moving MRI imaging system, and therefore these parts of the motion control device 1 do not obscure or produce artifacts on the diagnostic images. The motion control device 1 may also have the capacity to have pillows, cushions, and/or restraining devices attached to it at points where these pillows, cushions, and/or restraining devices aid in improving the comfort of the subject and/or in producing the correct posture and/or motion required for the test. The motion control device 1 as a unit is attachable and detachable by the operator 7 within the field of imaging, according to one embodiment of the present invention.

The base 31 in FIG. 6 is provided for the purpose of physically and immovably fixing and stabilizing the motion control device 1 within the field of imaging to either the floor, the imaging equipment, and/or a posture-assistance device 53 while the images and other measurements are being collected, and also for the purpose of providing an immoveable fixed structure on which to attach other sub-systems of the motion control device 1. The base 31 connects via attachment mechanisms at the points of contact between the base 31 and either the floor, the imaging equipment, and/or a posture-assistance device 53.

As the motion control device 1 physically attaches to and therefore may bear its weight onto the base 31, and as the motion control device 1 can be configured to also bear the entire weight of the subject, and with the subject moving during the testing process and therefore producing both static and dynamic forces, the base 31 needs the structural integrity and gripping force required to remain static, stable, and fixed in the presence of such loads and forces. The structural integrity is afforded by the use of rigid and strong materials such as plastics when radiolucent materials are desirable and in situations where compatibility with dynamic MRI systems is required, according to one embodiment of the present invention. Said gripping force is afforded by the use of strong fixation mechanisms at the points of contact, and may be accomplished by either: (1) the weight of the motion control device 1 itself, and the friction caused thereby and enhanced by the use of high-friction materials such as rubber at the points of contact, to fix and stabilize the motion control device 1; (2) screws, clamps, bolts, fasteners, straps, ties, cuffs, nuts, pins, or any other rigid or flexible fixation mechanism that provides immoveable fixation at the points of contact; and/or (3) some combination therein.

Base 31 can be a highly configurable sub-system, adapted and configured to have several configurations and versions to accommodate the different types of postures; different types, sizes, and configurations of posture-assistance devices; different sizes and geometries of imaging equipment and imaging fields; different materials at the point of contact to which to connect between the base 31 and either the floor, the imaging equipment, and/or a posture-assistance device 53; and different geometries and sizes of these points of contact.

As applied to the butterfly motion control device 29, the diagnostic imaging hardware 11 contains a field of imaging, which is a physical space in which objects imaged by the hardware must be located during the imaging process to produce images. The field of imaging can contain a posture assistance device such as a table, bed, chair, or other device intended to bear all or some of the subject's weight and to provide physical support to a specific type of posture. Alternatively, the field of imaging can contain no such devices if the subject can be situated directly onto the floor and/or the motion control device 1 and does not require the use of an additional device to bear weight and/or support specific postures. The "butterfly" motion control device 29, or sub-systems therein, occupy part or the entire field of imaging and is physically connected and supported either by resting on the floor itself, or by being physically and immovably attached to the imaging equipment or to one of the above-mentioned posture-assistance devices within the field of imaging. All parts of the "butterfly" motion control device 29 that are located within the field of imaging are constructed of materials that are either radiolucent in the case of use with video-flouroscopic and moving CT imaging systems, or alternatively compatible with on MRI images in the case of a moving MRI imaging system, and therefore these parts of the "butterfly" motion control device 29 do not obscure or produce artifacts on the diagnostic images. The "butterfly" motion control device 29 also has the capacity to have pillows, cushions, and/or restraining devices attached to it at points where these pillows, cushions, and/or restraining devices aid in improving the comfort of the subject and/or in producing the correct posture and/or motion required for the test. The "butterfly" motion control device 29 is attachable and detachable by the operator 7 within the field of imaging.

Figure 7A:
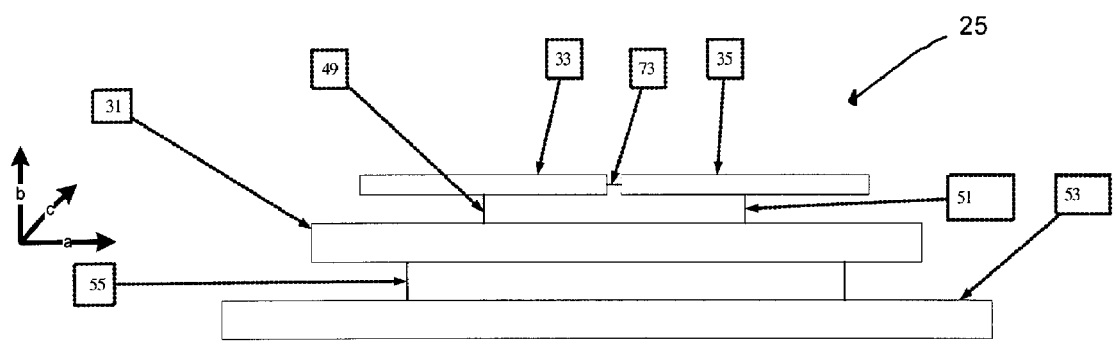
FIGS. 7A and 7B show side and top view block diagrams of the horizontally configured motion control device consisting of the two sub-systems and attachment mechanisms of the preferred embodiment of the horizontally configured motion control device in its "default" configuration, according to one embodiment of the present invention.
Figure 7B:
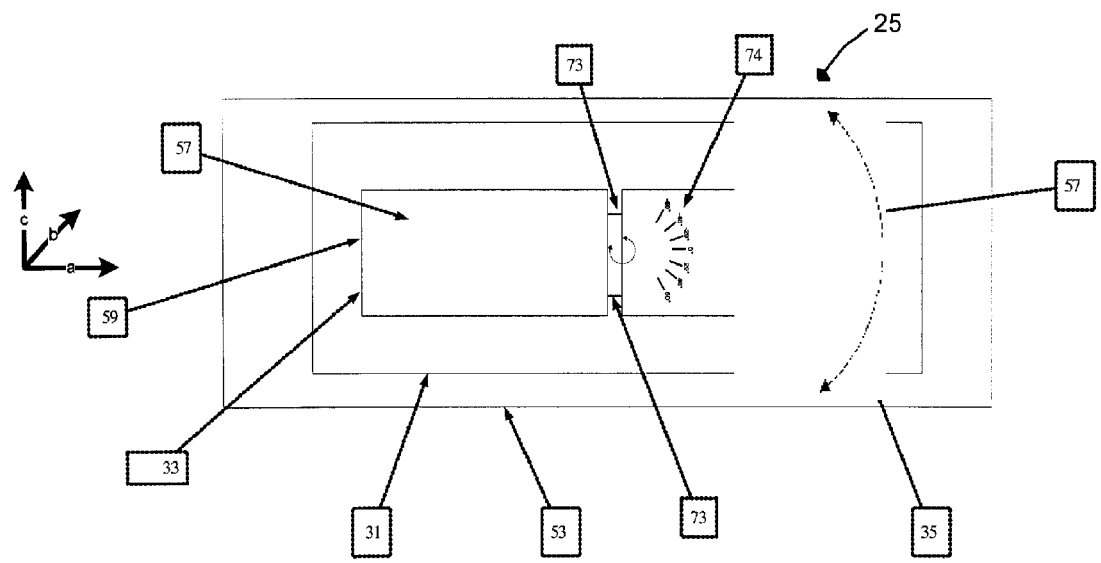

Turning now to FIGS. 7A and 7B, an illustration of a configuration of a horizontally configured motion control device 25 is provided. The base 31 serves as the base for the horizontally configured motion control device 25. The device 25 can be adapted and configured such that all other sub-systems attach or engage the base in some way. The base 31 can be optionally adapted and configured to detachably attach to either the floor, the imaging equipment, and/or a posture-assistance device 53 via the detachable anchoring device 55. The operator can then remove the motion control device 25 from the field of imaging. Moving up from this base 31, the next two physical sub-systems are the static platform 33 and the motion platform 35. The static platform 33 and the motion platform 35 are attached to each other by a suitable mechanism such as a hinging mechanism 73. When the device is in the "default" position, shown in FIGS. 7A and 7B, the device is locked such that the flat surfaces of both the motion platform 35 and static platform 33 reside within the same plane, but that still allows for the free rotation of the motion platform 35 within a plane (e.g., plane a-c) of its subject-facing surface about a fixed axis (b) of rotation. Other configurations or embodiments are possible that afford for the horizontal motion platform to move in a plane that is at an angle to the horizontal static platform. These "non-default" configurations are described in detail later in subsequent drawings.

The static platform 33 and motion platform 35 attach to the base 31 differently. See FIGS. 7A and 7B for a graphical description of how these sub-systems can be adapted to attach to each other. In this device, the base 31 attaches to either the floor, imaging equipment, and/or posture assistance devices 53 via the detachable anchoring device 55 and also connects to the static platform 33, which is held firm by a rigid immobilized static platform/member attachment mechanism 49. The base 31 and the motion platform 35 are attached by way of the motion platform attachment mechanism 51 that along with the hinging mechanism 73 allows for free rotation of the motion platform 35 within the plane of its flat subject-facing surface, while simultaneously allowing for the adjustment of the angle that this plane makes with the subject-facing surface of the static platform 33, such that these two planes intersect along the line of the hinge which occupies the linear space defined by the edges of these two platforms that face and are adjacent to each other. In the "default" configuration represented in FIGS. 7A and 7B, this angle is set to 180 degrees. In other "non-default" configurations, this angle can be adjusted to angles other than 180 degrees. The radio-opaque protractor 74 is shown on FIG. 7A. FIGS. 7C-E illustrate a configuration of the device.

Figure 8A:
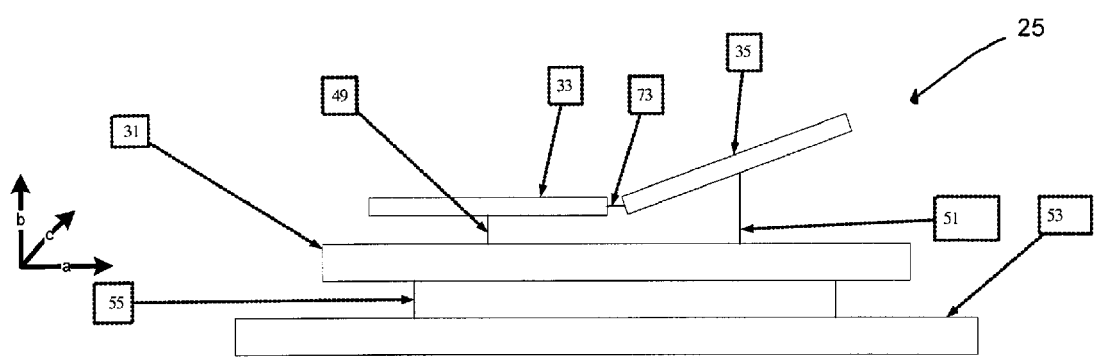
FIGS. 8A and 8B show side view block diagrams of the horizontally configured motion control device and related parts of the preferred embodiment in the "front-up" (FIG. 7A) and "front-down" (FIG. 7B) configurations, according to one embodiment of the present invention.
Figure 8B:
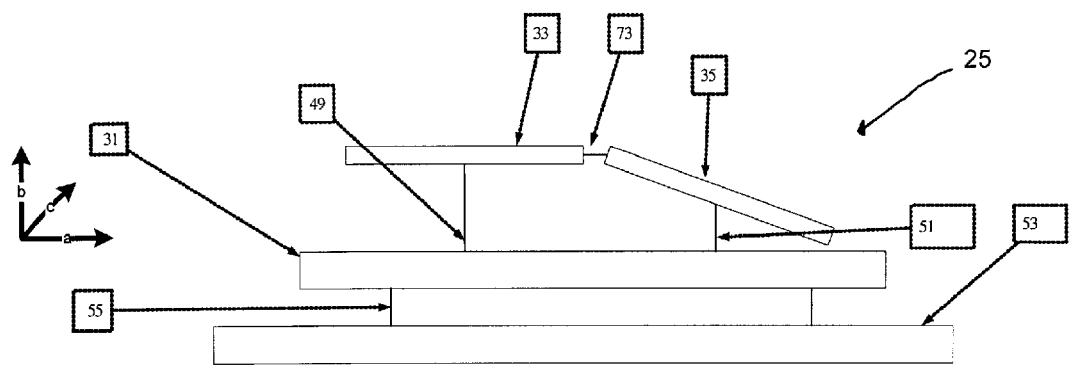

FIGS. 8A and 8B illustrate the functionality of the motion platform attachment mechanism 51 and the hinging mechanism 73. FIG. 8A depicts the side view block diagram of attachment mechanisms and parts of the horizontally configured motion control device 25 in a "front up" configuration, where the hinging mechanism 73 connects the static platform 33 with the motion platform 35 along the edges of these platforms that face each other in such a way as to allow these two platforms to rotate about an axis c of the hinge. In this configuration, the connection between the base 31 and the static platform 33 is held firm by the rigid immobilized static platform/member attachment mechanism 49. However, the motion platform attachment mechanism 51 between the base 31 and the motion platform 35 functions differently. The motion platform attachment mechanism 51 is adapted and configured to lengthen within a plane (e.g., plane a-c) along an axis as well as the ability to change the angle of attachment to both the base 31 and the motion platform 35 such that the end of the motion platform 35 opposing the end adjacent to the static platform 33 can move up or down (along the b axis) so that the plane of the motion platform 35 is at an angle to the plane of the static platform 33 and that these two planes intersect along the line created by their common edge which is a space occupied by the hinging mechanism 73. The radio-paque protractor 74 enables an assessment of movement of the spine during the imaging process.

FIG. 8B represents a side view block diagram of attachment mechanisms and parts of a horizontally configured motion control device 25 in a "front down" configuration. In this configuration, the hinging mechanism 73 functions in the same way allowing for the static platform 33 and motion platform 35 to rotate about the axis c of the hinge such that it changes position from lying within a plane (e.g. c-a plane) to rotating about the c axis. The rigid immobilized static platform/member attachment mechanism 49 in this configuration can be lengthened or shortened, but fixed at a right angle to the platform base 31 and the static platform 33. The motion platform attachment mechanism 51 can be lengthened or shortened such that the angle of attachment to the motion platform 35 and the platform base 31 is no longer a right angle, and instead any other angle dictated by the geometric configuration of the device indicated by the prescriber.

Figure 9B:
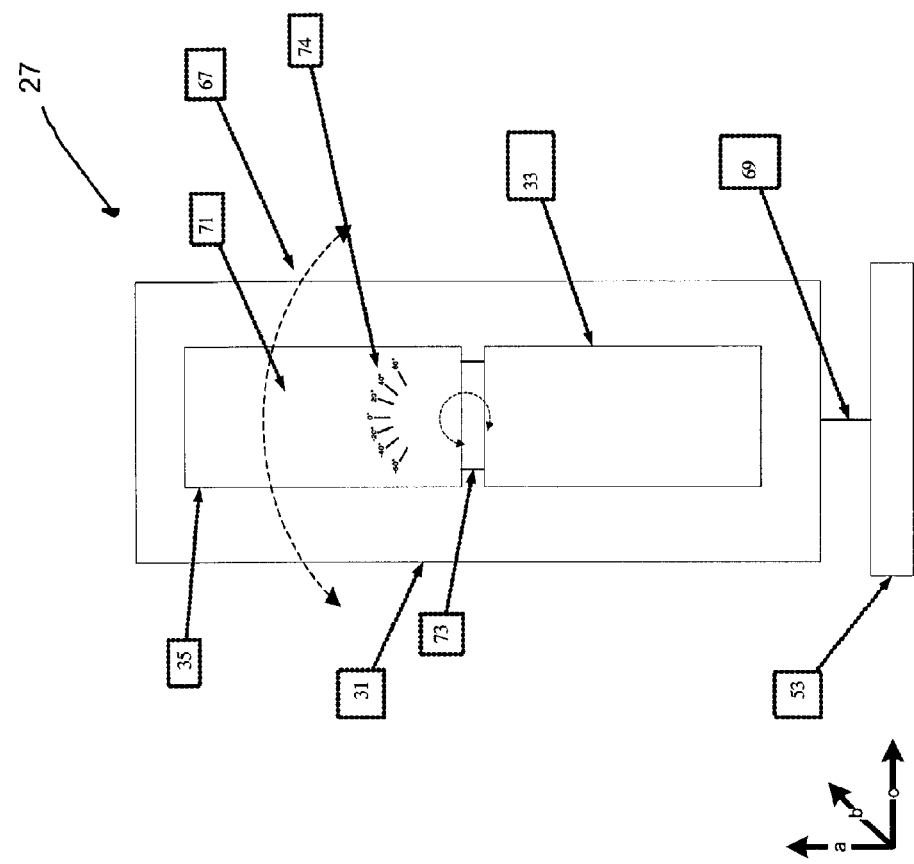
FIGS. 9A and 9B show side and front view block diagrams, respectively, of Design 1 of the vertically configured motion control device in the "default" configuration, according to one embodiment of the present invention.
Figure 9A:
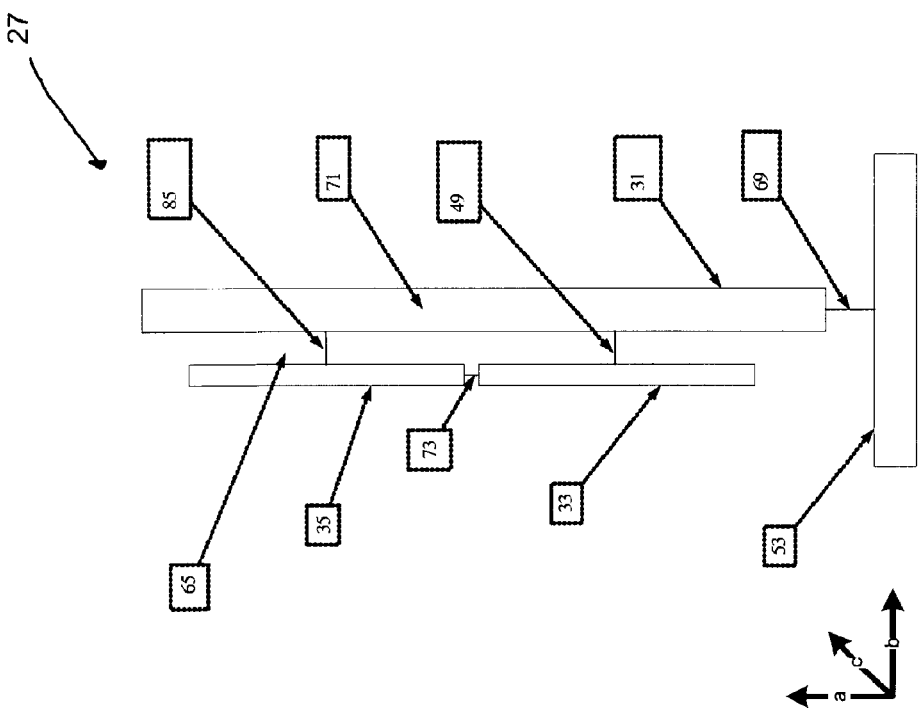
Figure 9C:
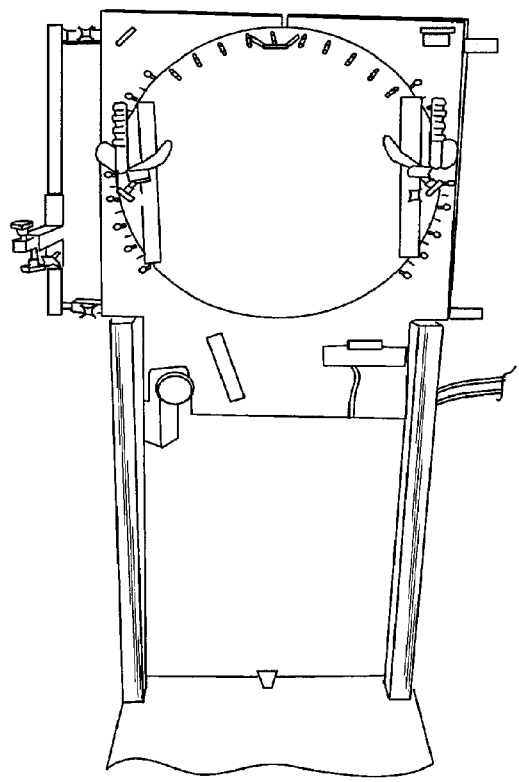
FIGS. 9C-E illustrate a device from different views.
Figure 9D:
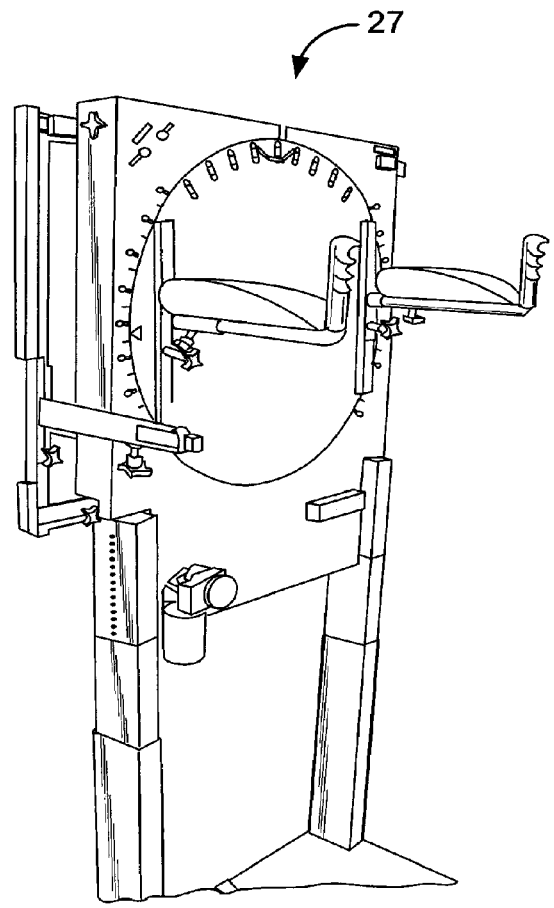
Figure 9E:
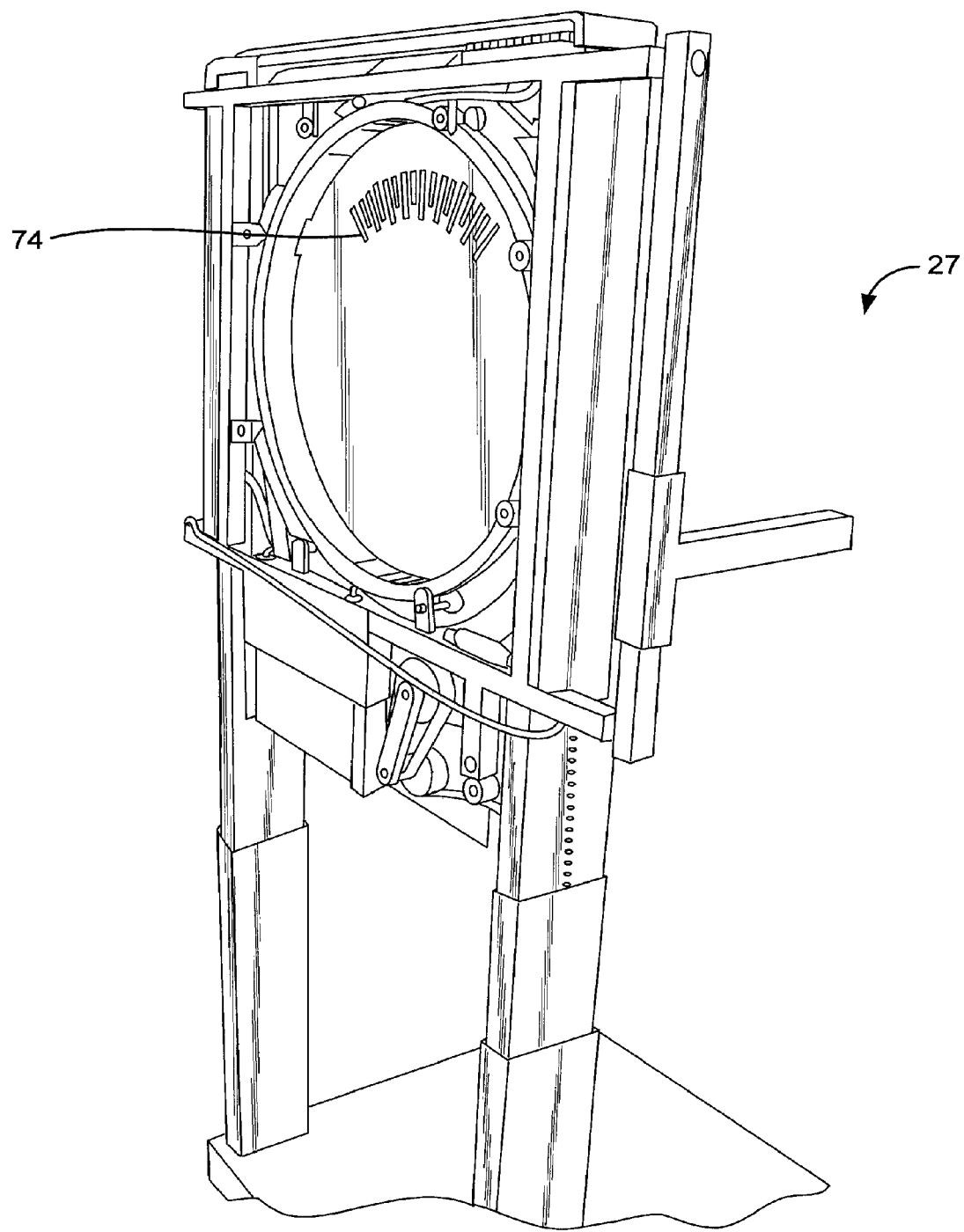

As reflected in FIGS. 9A and 9B, the frame 31 connects to the base 53 of vertically configured motion control device 27 at a rigid base to frame connection mechanism 69. The frame 31 is the frame to which all other sub-systems attach in some way. Moving out from this frame 31, the next two physical sub-systems are the static member 33 and the motion member 35. The frame 31 attaches to the static member 33 by way of a rigid immobilized static platform/member attachment mechanism 49 like the one described for FIGS. 7A and 7B with the added capability of providing cantilevered support for the weight of the static member 33 and any of the attached subject body parts. The frame 31 attaches to the motion member 35 by way of a motion member attachment mechanism 85 that allows free rotation around a fixed axis within the same plane as that of the subject facing surface of the static member, and provides for the cantilevered support for the weight of the motion member 35 and the subject body parts that could be connected to it. The static member 33 and motion member 35 and are attached to each other by the vertically configured motion control device hinging mechanism 73 that when in the "default" position represented in FIGS. 9A and 9B, is locked such that the flat surfaces of both the static member 33 and the motion member 35 reside within the same plane, but still allows for the free rotation of the motion member 35 around a fixed axis within that plane. The radio-opaque protractor 74 is shown on FIG. 9B. FIGS. 9C-E illustrate a configuration of the device.

Figure 10C:
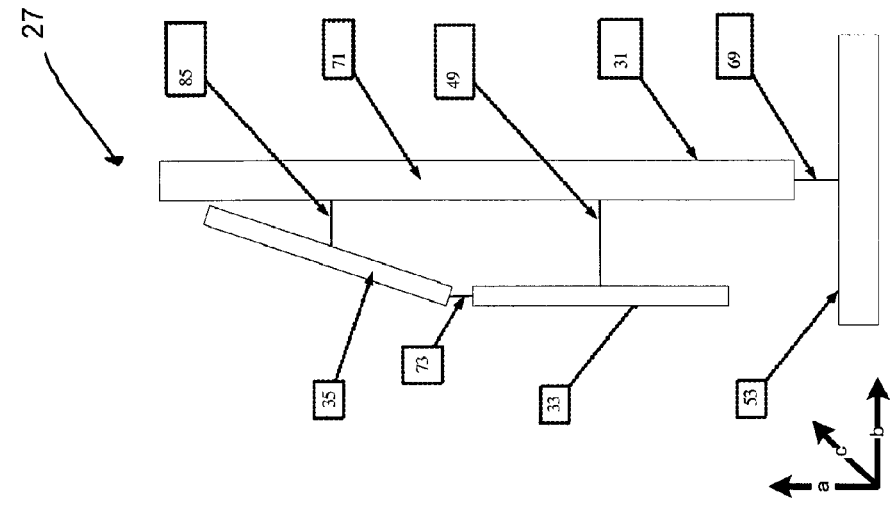
FIGS. 10A, 10B, and 10C show side view block diagrams of Design 1 of the vertically configured motion control device in the "default", "top out" and "top in" configurations, respectively, according to one embodiment of the present invention.
Figure 10B:
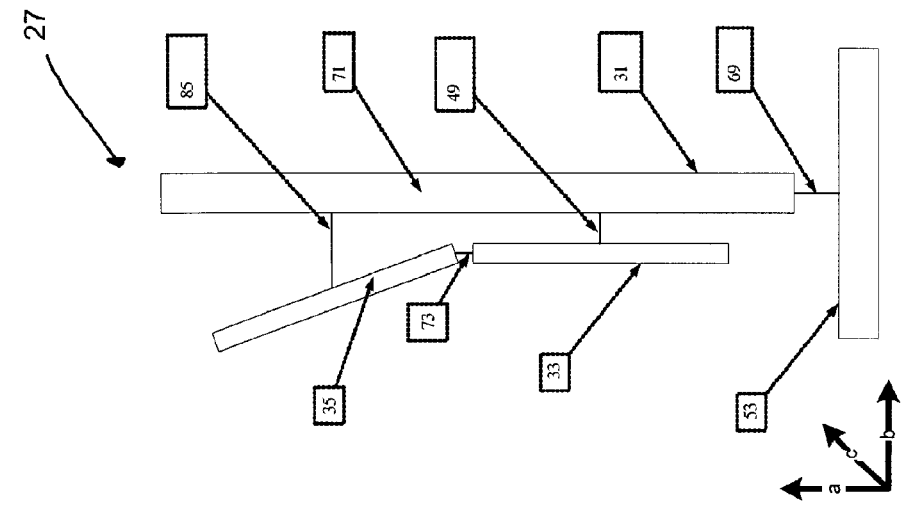
Figure 10A:
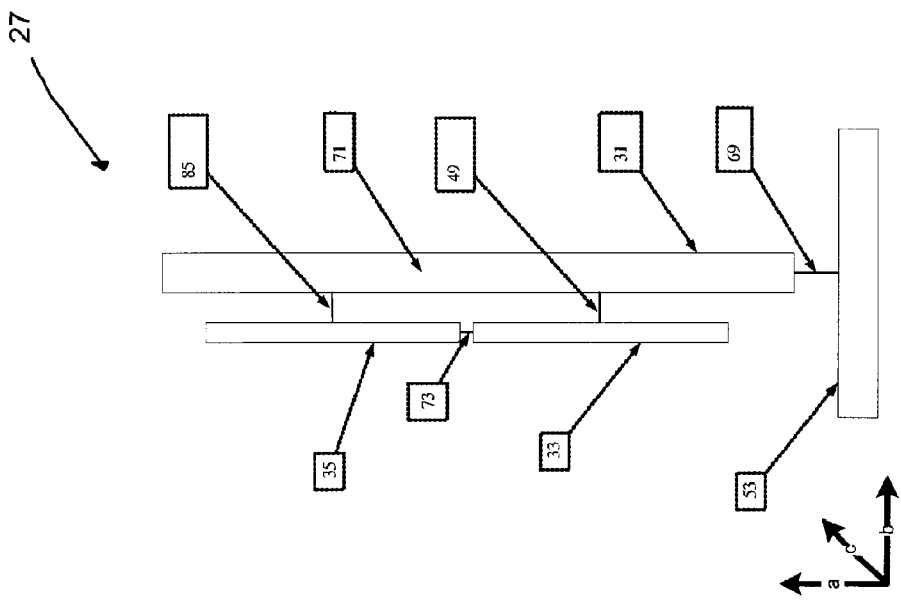
Figure 11B:
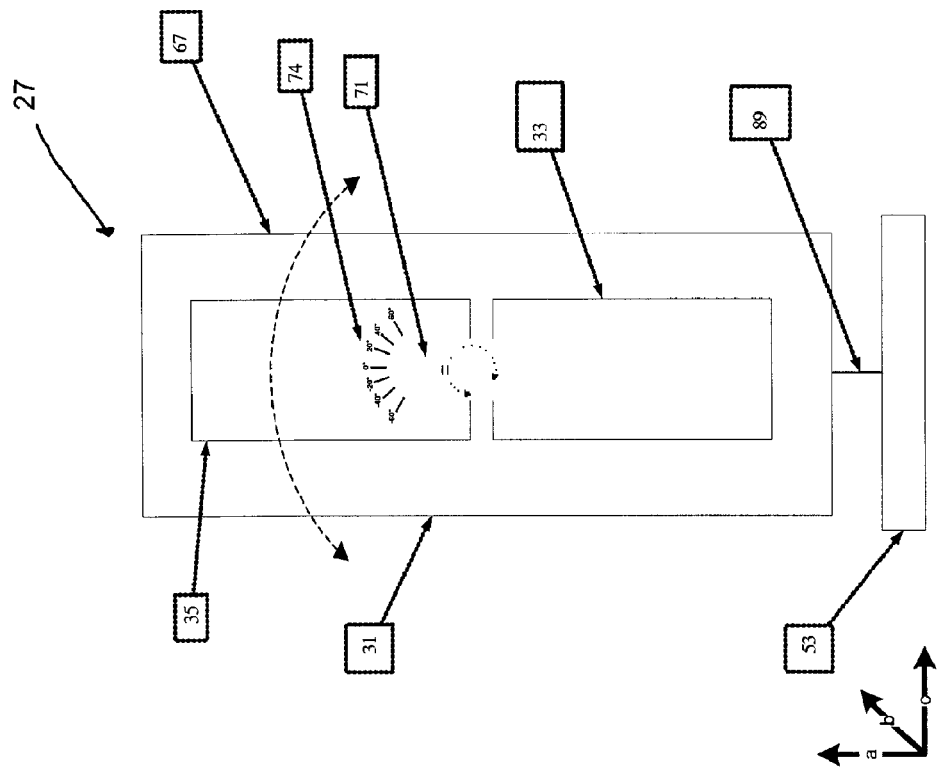
FIGS. 11A and 11B show side and front view block diagrams, respectively, of Design 2 of a vertically configured motion control device in a default configuration, according to an embodiment of the invention.
Figure 11A:
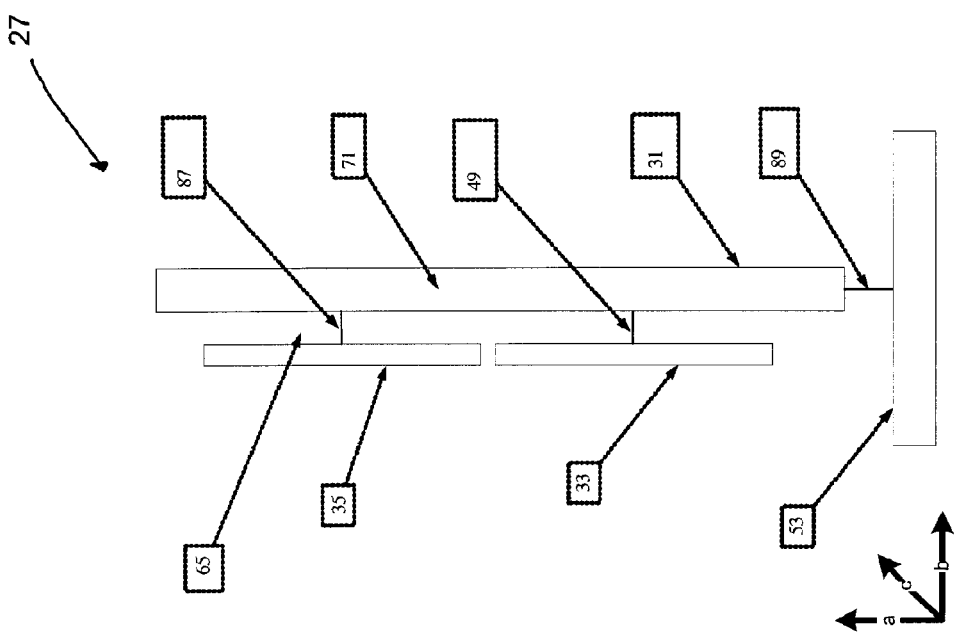

FIGS. 10A, 10B, and 10C represent the side view block diagram of the vertically configured motion control device 27 in the "default", "top out" and "top in" configurations, respectively. The "default" configuration given in FIG. 11A is as described in the previous paragraph. In FIG. 11B, the "top out" configuration, the attachment mechanism 85 connects the static member 33 to the motion member 35 and can lengthen or shorten along the b axis and/or change the angle of attachment to frame 31 and motion member 35 such that the top of the motion member 35 can move away from the frame 31 so that the plane of the motion member 35 is at an angle to the plane of the static member 33 and that these two planes intersect along the line created by their common edge, the space of which is occupied by the motion control device hinging mechanism 73. Furthermore, the motion member attachment mechanism 85 allows for the free rotation of the motion member 35 around a fixed axis within that plane while providing cantilevered supporting the weight of the motion member and any of the subject's body parts that are connected to it.

In FIG. 10C, the "top in" configuration, the motion member attachment mechanism 85 illustrates its ability to lengthen and shorten along the b axis and change the angle of attachment to the connecting frame 31 and motion member 35. Additionally, in this configuration, the static platform/member attachment mechanism 49 can lengthen along b axis, pushing the static member 33 away from the frame 31 while keeping the static member 33 in a non-changing orientation with respect to the frame 31.

As described above, there are two designs, Design 1 and Design 2, given for an embodiment of the vertically configured motion control device 27 from FIGS. 5 and 6. FIGS. 11A, 11B, 12A, and 12B illustrate Design 2, which differs from Design 1 principally by the inclusion of a tilting mechanism 89 to replace the rigid base to frame connection mechanism 69 as well as the motion control device hinging mechanism 73.

FIGS. 11A and 11B illustrate Design 2 of the vertically configured motion control device in the default configuration. In this configuration, the motion member attachment mechanism 87 is fixed in length, connects at a right angle to the frame 31 and the motion member 35, and allows for the free rotation of the motion member 35 around a fixed axis b and within the same plane as the static member 33, all while providing cantilevered support for the weight of the motion member and the subject's body parts that are connected to it. In this design, the frame 31 is attached to the base 53 by way of a frame tilting mechanism 89 that supports the weight of the whole motion control device. The radio-opaque protractor 74 is shown on FIG. 11B.

FIGS. 12A and 12B illustrate the vertically configured motion control device in the "default" and "angled" configurations, respectively. The "default" configuration is described in the previous paragraph. In the "angled" configuration, the frame tilting mechanism 89 supports the weight of the motion control device, and also provides for the rotation of the frame 31 and attached static member 33 and motion member 35 together at an angle to the base 53 by way of changing the angle at which it attaches to the base 53 and the frame 31, and locking the frame tilting mechanism 89 into an angle specified by the prescriber, after which the vertically configured motion control device will remain stable and testing may begin.

Figure 13B:
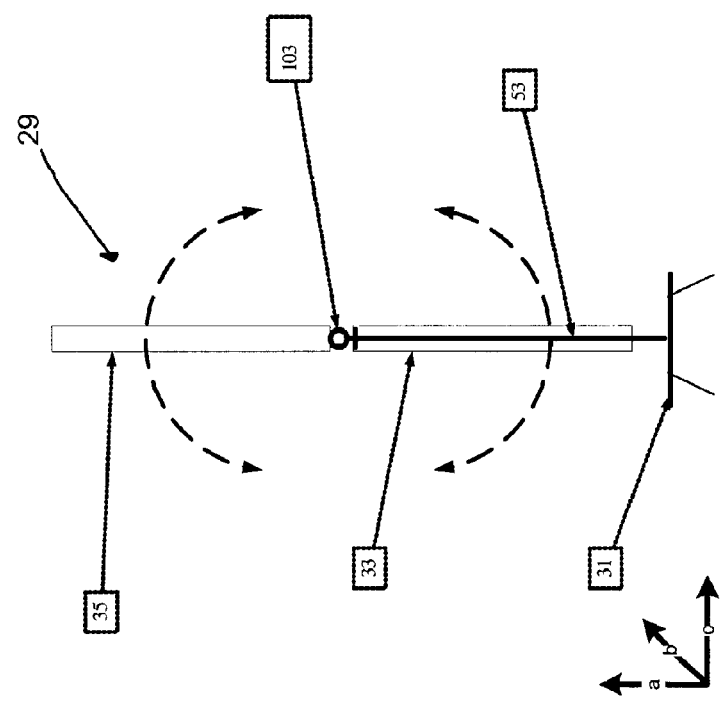
FIGS. 13A and 13B show front and side view block diagrams of the "butterfly" motion control device in the "default" configuration, and illustrates the range of positions for different "non-default" configurations where each member can hinge independently of the other to a maximum of 180°, according to one embodiment of the present invention.
Figure 13A:
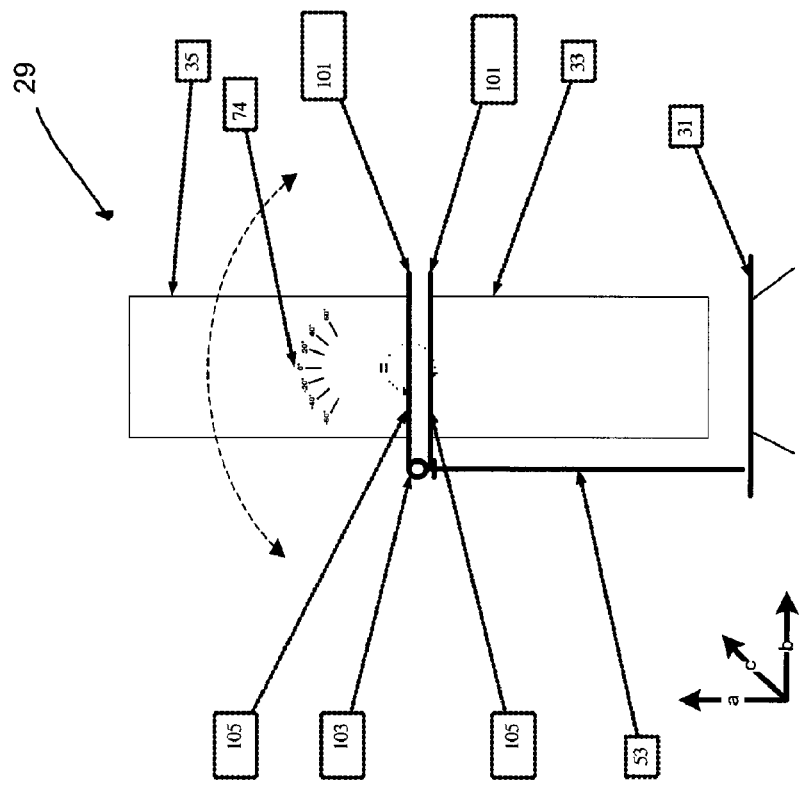

Turning now to FIG. 13, the "butterfly" motion control device 29 is illustrated. The base 31 is provided for the purpose of physically and immovably fixing and stabilizing the motion control device 29 to either the floor, the imaging equipment, and/or a posture-assistance device while the images and other measurements are being collected, and also for the purpose of providing an immoveable fixed structure on which to attach other sub-systems of the motion control device 29.

As this motion control device 29 is adapted and configured to physically attach to and bears its weight onto the base 31 and support frame 53, and the device 29 can be configured to also bear some or all of the subject's bodyweight (with the subject moving during the testing process and producing both static and dynamic forces), the base 31, support frame 53, and the connected structural support parts described in the proceeding paragraphs need the structural integrity and gripping force required to remain static, stable, and fixed in the presence of such loads and forces. Said structural integrity is afforded by the use of rigid and strong materials such as plastics or particle board when radiolucent properties are required and in situations where compatibility with dynamic MRI systems is required. Said gripping force is afforded by the use of strong fixation mechanisms at the points of contact, and may be accomplished by either: (1) the weight of the "butterfly" motion control device 29 itself, and the friction caused thereby and enhanced by the use of high-friction materials such as rubber at the points of contact, to fix and stabilize the "butterfly" motion control device 29; (2) screws, clamps, bolts, fasteners, straps, ties, cuffs, nuts, pins, or any other rigid or flexible fixation mechanism that provides immoveable fixation at the points of contact; and/or (3) some combination therein.

The support frame 53 connects to the base 31, which is adapted and configured to provide a stabilization device that facilitates positioning the device on the floor.

The support frame 53 functions as a structural support member, connecting at its base to the base 31, and extending from the left side (in front view, as in FIG. 13A) to a height that is slightly greater than the height of the static member 33. The support arm 101 connects at the top of the support frame 53 by way of a revolving attachment mechanism 103 and extends out to the right (in front view, as in FIG. 13A) at a 90 degree angle to the support frame 53 and splits into a two prong tuning fork configuration. The revolving attachment mechanism 103 rigidly connects to the support frame 53 and flexibly connects to the support arm 101 in such a way that it affords: (1) a fixed 90° angle between the support frame 53 and the support arm 101, (2) the ability for the support arm 101 to revolve freely about its long axis, and (3) the ability for the support arm 101 to be locked into a specific degree of rotation and thus a specific plane called the plane of the support arm. The plane of the support arm 101 is defined as the plane in which both arms of the tuning fork reside.

As a sub assembly of the support arm 101, there is a hinging mechanism 105 that runs along each fork of the support arm 101. The hinging mechanism 105 provides for the connection between each fork of the support arm 101 and the static and motion members 33, 35, where the motion member 35 is attached to the upper fork (in "default" view as in FIG. 13A), and extends upwards, and the static member 33 is attached to the lower fork (in "default" view as in FIG. 13A), and extends downwards. The motion control device is configurable, and in its default position, the plane of the support arm 101 is parallel to the planes of both the static member 33 and the motion member 35, and perpendicular to the plane of the support frame 31. The motion control device 29 can be configured such that either or both the static member 33, and/or the motion member 35 can rotate 90° from that default plane in either direction, and independently from each other. At the most extreme positions, (90° rotation of each planar member), the motion control device 29 would be in the same configuration as the horizontally configured motion control device 25 of FIG. 8. Furthermore, the dual hinging mechanism 105 allows free rotation of the motion member 35 around a fixed axis within the same plane that the planar motion member is configured in.

According to the present invention there is provided the specification of a methodology for interpreting the measurements provided by the present invention to generate diagnostic results that can be clinically applied for the treatment of subjects with joint problems or performance issues. The support arm 101 and the hinging mechanism 105 is constructed with a geometry and out of materials that do not obscure or produce artifacts on the diagnostic imaging through the use of radiolucent and/or non-magnetically active materials within the field of imaging. The radio-opaque protractor 74 is shown on FIG. 13A.

IV. DEVICE OPERATION

FIGS. 14A and 14B represent a diagram of Design 1 of the vertically configured motion control device 27 as represented in FIGS. 9 and 10 which engages a subject 3 or patient. FIG. 14A shows the subject 3 standing against the motion control device 27 with his or her torso pressed against the motion member 35 and legs adjacent the static motion member 33. Optional restraining mechanisms 91 and 93 are provided to physically attach engage the subject's 3 body and immobilizes the attached body parts against the motion member 35 and static member 33, respectively. FIG. 14A shows how Design 1 can be used to study bending of the spine from a starting position within the coronal plane into a posture where the subject's spine is in flexion as a result of the subject leaning out of the coronal plane posteriorly. Additionally, the operation of the device can be adjusted such that the subject leans out of the coronal plane anteriorly. FIG. 14B shows how Design 1 can be used to study flexion and extension of the spine from a position within the sagittal plane when the spine is bent laterally to the subject's right side. The configuration of the device depicted is such that the subject could also bend laterally to the left side without changing positions relative to the device. Both FIGS. 14A and 14B show Design 1 in a "top in" configuration, however this design is able to rotate around the hinging mechanism 73 such that the subject 3 can remain in the same orientation with respect to the device from the "top out" to the "top in" configurations, to affect a change in the posture of the subject such that the subject is bent in the opposite direction than is afforded in the "top in" configuration.

FIGS. 14C and 14D represent a diagram of Design 2 of the vertically configured motion control device 27 as represented in FIGS. 11A, 11B, 12A, and 12B. FIG. 12B represents how the frame 31 and connected static member 33 and motion member 35 can rotate as a group from the neutral position to an "angled" configuration. FIG. 14D shows how Design 2 in the "angled" configuration will produce the exact same functionality as Design 1 would do when in the "top out" configuration. In FIG. 14D, the subject 3 is attached to the static member 33 and motion member 35 using the restraining mechanisms 91 and 93 at the hips and chest. The subject 3 stands with his or her back pressed against the motion member 35, which affords for side bending of the spine while in a posture wherein the subject's 3 spine is extended. The subject 3 could also be positioned with his or her flank facing the device, which would afford for flexion and extension of the spine while in a posture wherein the subject's 3 spine is laterally bent. Unlike Design 1 which can rotate from a "top out" to a "top in" configuration as illustrated in FIGS. 11B and 11C, Design 2 illustrated in FIGS. 14C and 14D can rotate only in one direction, from a "default" to an "angled" configuration. Therefore to affect the functionality provided by device 1 in the "top in" configuration as represented in FIG. 14A, the subject 3 must rotate 180 degrees with respect to the device. Such a rotation of the subject 3 is not required with Design 1, as this functionality is achieved by putting the device in a "top in" configuration, as shown in FIG. 14A. FIG. 14C shows how the subject must rotate 180 degrees with respect to the device to be able to achieve with Design 2 in the "angled" configuration the exact same functionality as Design 1 in the "top in" configuration, however with the difference that the subject is rotated 180 degrees with respect to the device with Design 2, wherein this is not required with Design 1 as represented in FIG. 14A.

Figure 15A:
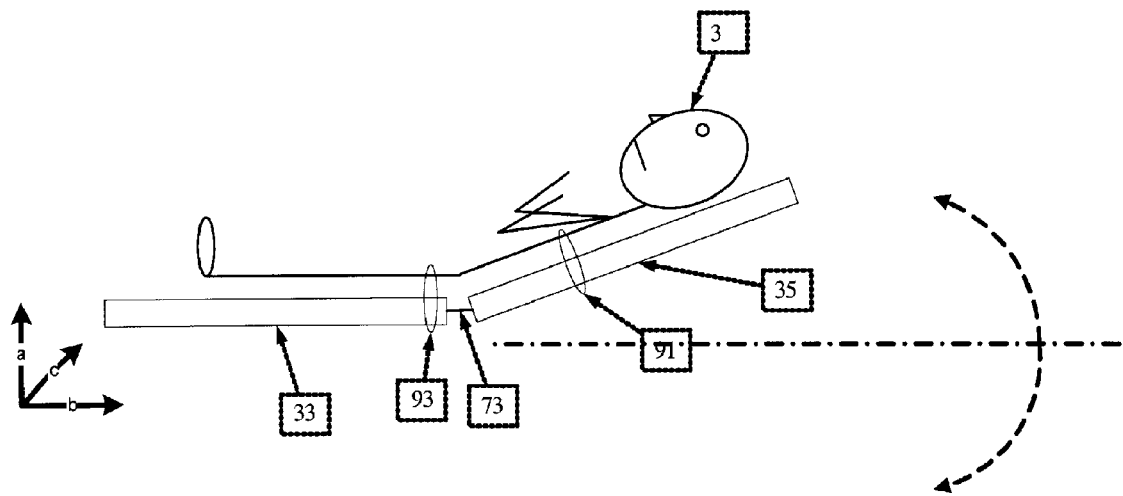
FIGS. 15A, and 15B illustrate the functionalities of the horizontally configured motion control device in the "front up" configuration, according to one embodiment of the present invention.
Figure 15B:
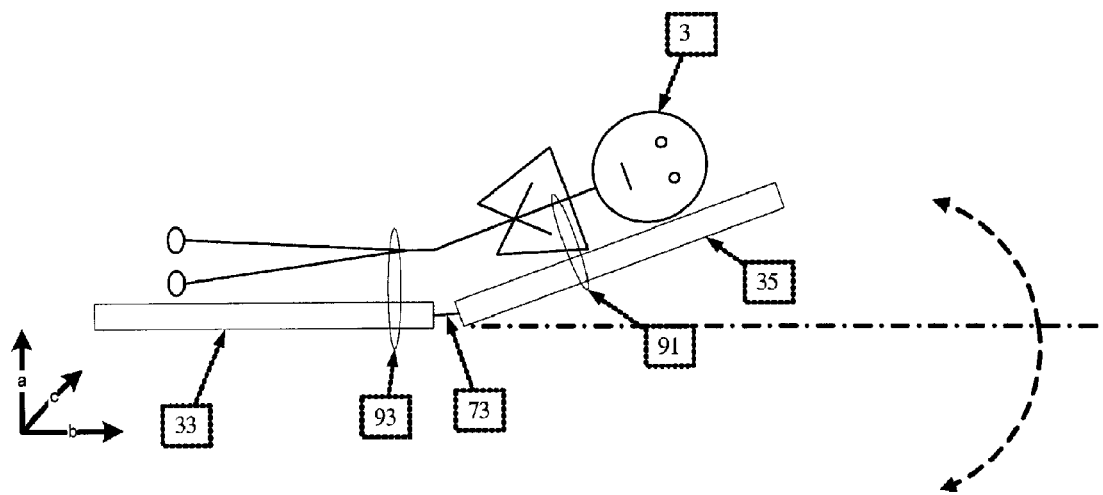
Figure 17A:
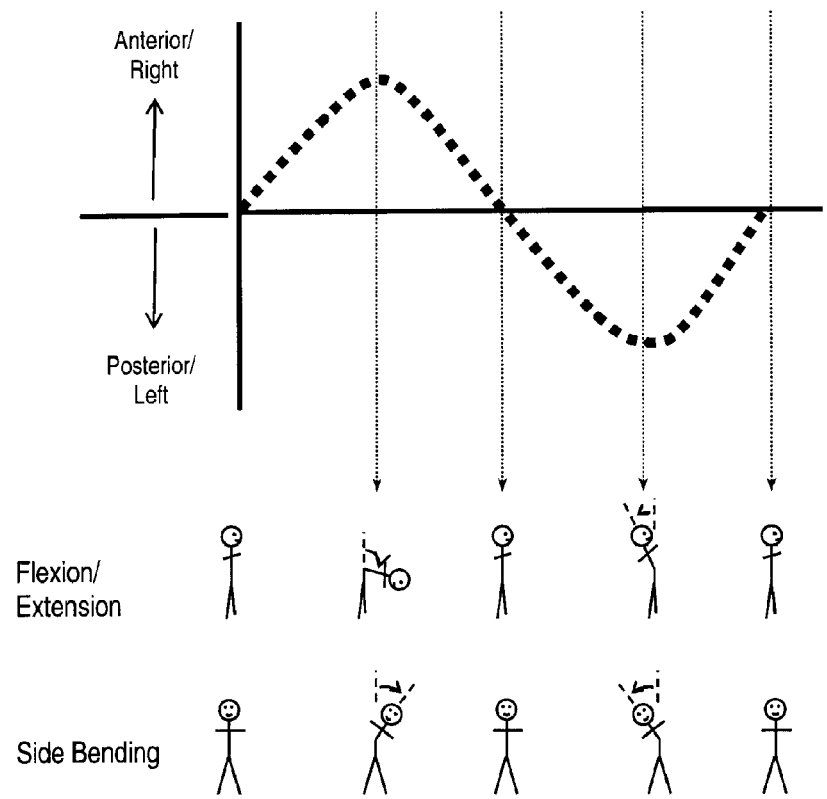
FIGS. 17A-B is an illustrative representation of a subject's intervertebral motion as measured while the subject bends through a range of motion with a sensor output producing low noise measurement output as compared to the illustrative high noise measurement output presented in FIG. 2G, and a graph showing the difference in the frequency distribution of L1/L2 range of motion taken from a population of normal healthy subjects showing how the variability of this distribution is dramatically reduced with the use of the present invention as compared to the traditional spinal kinematic studies.
Figure 17B:
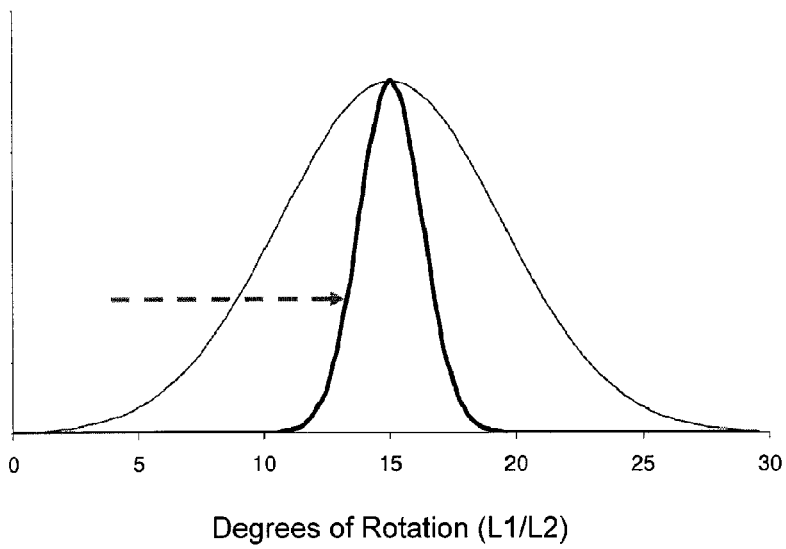
Figure 18A:
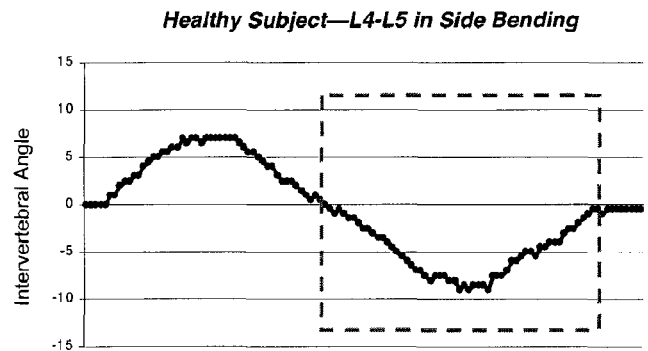
FIGS. 18A-E illustrate normal healthy side bending motion, immobility in left bending at L4/L5; pathological stiffness in left bending at L4-L5, paradoxical motion in left bending at L4/L5 and laxity in bending at L3/L4 which are detectable with the devices and methods of the invention.
Figure 18B:
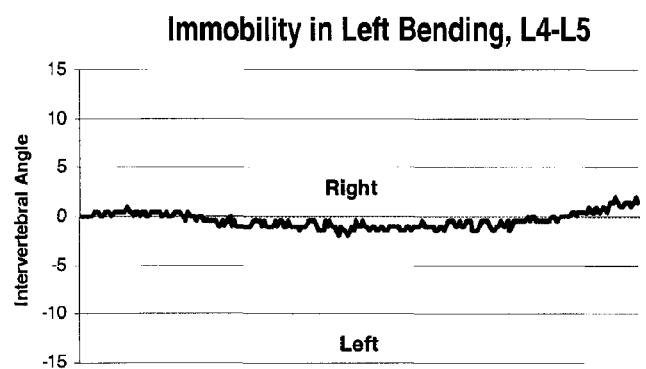
Figure 18C:
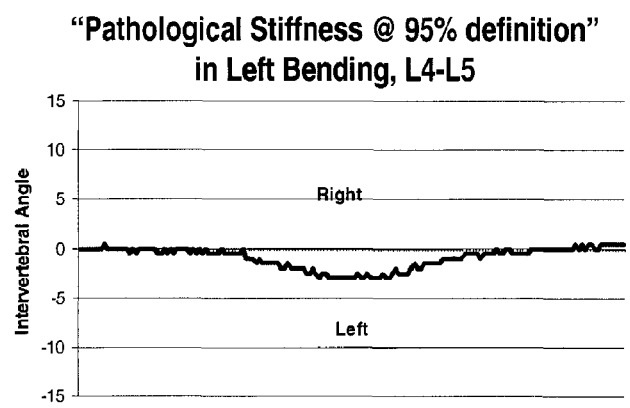
Figure 18D:
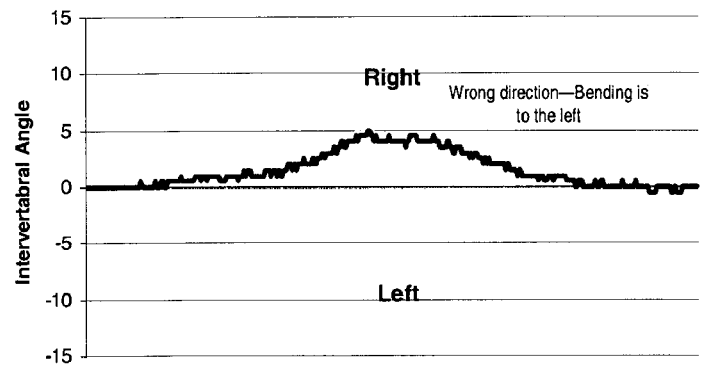
Figure 18E:
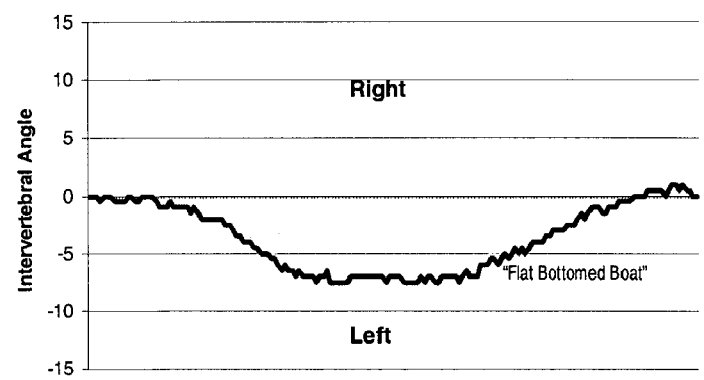
Figure 19A:
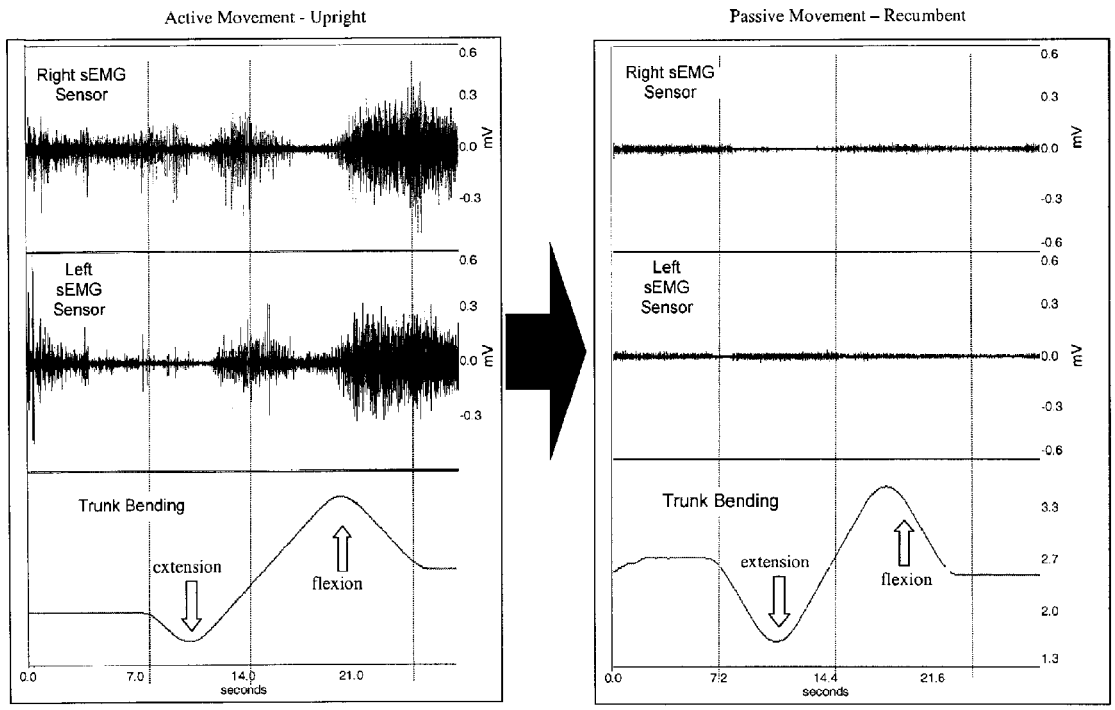
FIGS. 19A-D illustrate experimental results from a muscle function study.
Figure 19B:
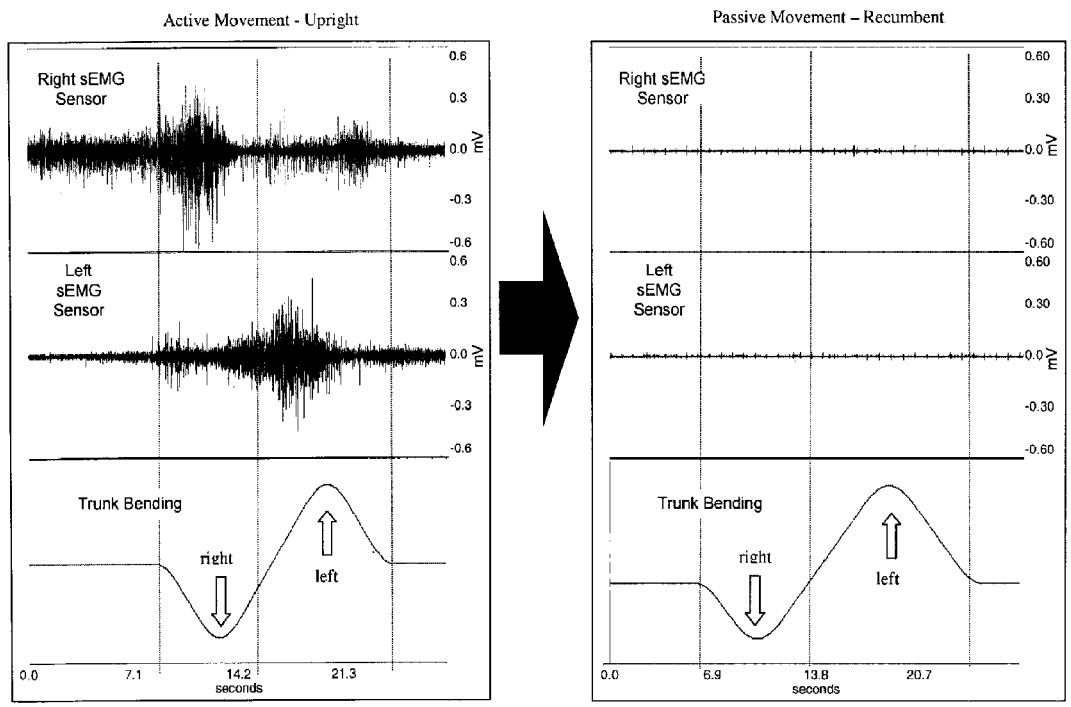
Figure 19C:
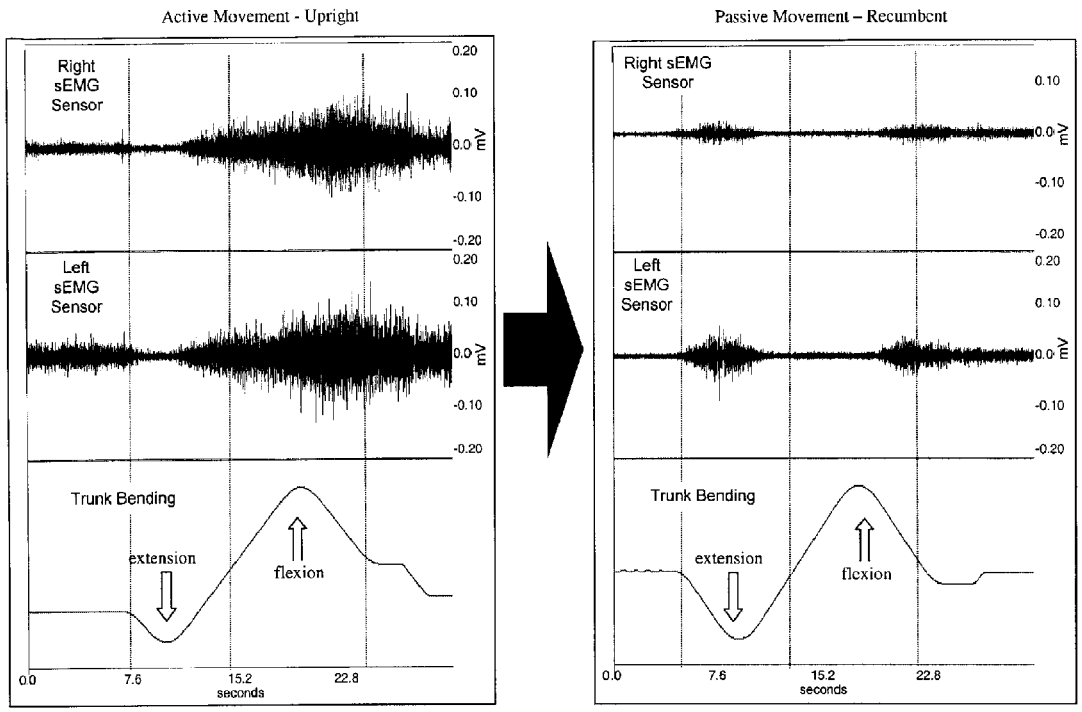
Figure 19D:
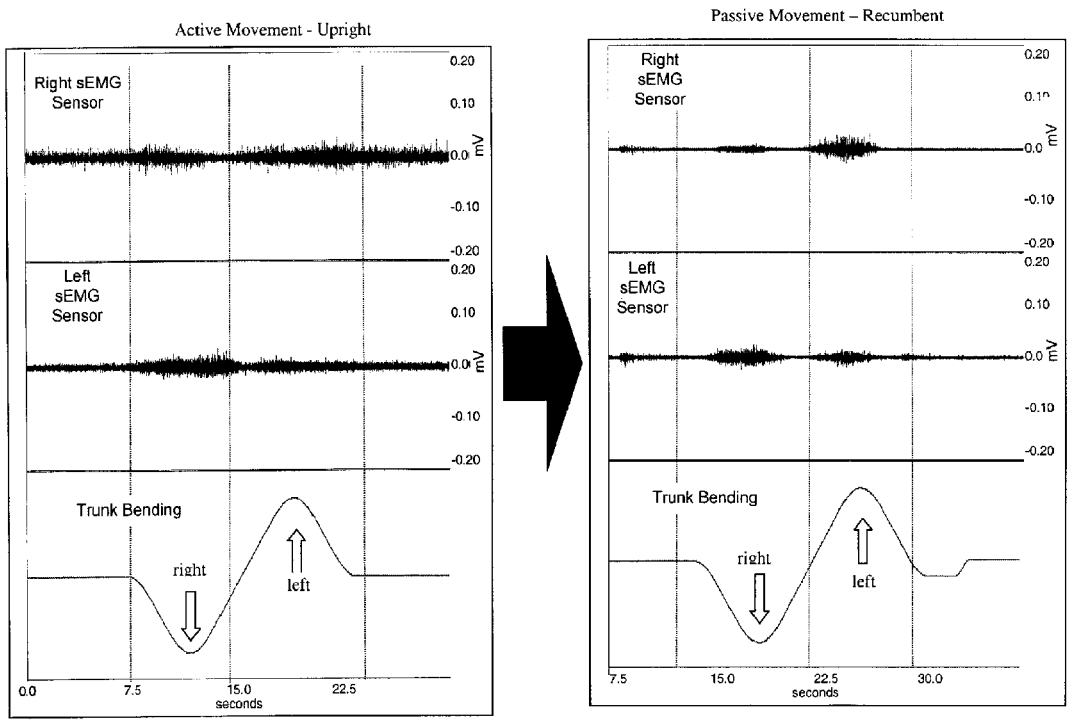

FIGS. 15A and 15B represent a diagram of the horizontally configured motion control device 25 as represented in FIG. 8 which engages a subject 3 or patient. FIG. 15A shows the subject 3 lying horizontally on the motion control device 25 with his or her side (i.e., torso) pressed against the motion member 35 and his or her legs are positioned adjacent the static member 33. As will be appreciated by those skilled in the art, the subject 3 can be positioned with respect to the motion control device 25 such that his or her side is pressed against the static member 33 while his or her legs are positioned against the motion member 33. Optional restraining mechanisms 91 and 93 are provided to physically attach engage the subject's 3 body and immobilizes the attached body parts against the motion member 35 and static member 33, respectively. FIG. 15A shows bending of the spine in a horizontal position from a starting position within the sagittal plane into a posture where the subject's spine is moved upward out of the sagittal plane. Additionally, the operation of the device can be adjusted such that the subject leans out of the sagittal plane toward the floor. FIG. 15B shows a subject 3 lying with his or her back pressed against the motion member 35 and the static member 33 while lying horizontally. The device rotates about an axis such that the patient is moved out of the coronal plane The configuration of the device depicted is such that the subject could also bend posteriorly without changing positions relative to the device. After the motion control 1 device is configured to any of these positions position, the motion member 35 is additionally free to rotate about an axis to affect a joint motion to be studied.

In all of the embodiments, where a protractor is provided, as the subject moves or is moved, the protractor 74 puts a measurement of trunk bending angle on every single image.

Different Joints Other than the Spine, Neck, Knee, Hip, Shoulder, and Elbow in Humans:

The specific geometries and configuration for the three motion control devices are specific to studies of the spine, neck, knee, hip, shoulders, and elbow in humans. Different joints such as the ankle, toe joints, finger joints, wrist, and jaw in humans will require some potentially different geometries, sizes, and configurations of the three motion control devices to enable investigations into those joints using the present invention. It will also require some potentially different geometries, sizes, and configurations of the three motion control devices, or the specification of a new motion control device design, to enable the use of the present invention to investigate the joints of non-human animals with internal bony skeletons, however the motion apparatus configuration given in FIG. 3 will be unaffected by such changes.

Different Types of Moveable Connections for the Motion Platform/Member in the Horizontal and Vertical Devices:

The plane in which the motion platform/member rotates is two dimensional and within the plane of the motion platform/member, such that the axis of rotation of the motion platform/member is orthogonal to the plane of the motion platform/member in the preferred embodiment of the horizontal, vertical and "butterfly" motion control devices. In some case, the rotation might not be restricted to a two dimensional plane, but instead could sweep out a three dimensional surface (in which case 3 dimensional imaging might be required). Alternatively, the motion platform/member might not sweep out a circular arc of motion but instead might sweep out some other shape of arc in a non-circular rotational pattern. The position and orientation of the axis of rotation of the motion platform/member might also be configurable by the operator. The motion of the motion platform/member can be translational and not rotational, or can also be both translational and rotational. Typically at least two dimensional rotational motion is provided, wherein the axis of rotation is fixed and orthogonal to the plane of the motion platform/member.

Different Connections Between and Among the Components of the Vertical and Horizontally Configured Motion Control Devices:

Specific configurations for the connections between the static platform/member 33 the motion platform/member 35 and the platform/member base/frame 31. These configurations afford the functionality of the motion apparatus as specified. However these connections are configured differently, with the potential for each connection to have different properties and capabilities, such that different designs of these connections can be used to affect the same functionality that is put forward with the preferred embodiment. For example, the static platform/member attachment mechanism 49 can be configured such that it is always at a right angle to the components to which it connects. This restriction might not be required and it could be configurable such that it makes non-right angles with the components with which it connects.

Ability to Provide Unguided Motion:

The horizontal, vertical and "butterfly" motion control devices are contemplated to always provide guided motion in the form of imposing a rotation about a fixed axis and within a specific plane of motion. In some instances it would be possible to provide for unguided motion of the joint, wherein the subject's internal joint mechanics provide the guidance for the joint motion, as opposed to having the guidance imposed on the subject by the motion control devices.

Ability to Lock the Motion Platform/Member:

The motion platform/member can be configured to rotate about a fixed axis and within a specific plane of motion. In such a design, it would be possible to lock the motion platform/member at any angle within the rotation for the purpose of performing diagnostic testing on the subject in that position.

Different Orientations of the Static Platform/Member with Respect to the Motion Platform/Member:

The horizontal, vertical and "butterfly" motion control devices provides a capability to latitudinally hinge the motion platform/member with respect to the static platform/member, however these two components are restricted from twisting along the longitudinal axis with respect to one another. Both latitudinal hinging and longitudinal twisting may also be provided between these components.

Different Positioning of the Subject in the Motion Apparatus:

In most cases, the subject will lie either on his or her flank, front, or back facing the motion control devices. However, specific posture assistance and restraining devices can also be provided to affect the ability to position the subject in any orientation with respect to the motion control devices, and not just the four "orthogonal" orientations wherein the lateral or anterior/posterior axis of the subject is orthogonal to the subject facing surfaces of the motion apparatus.

Design 2 of the Vertically Configured Motion Control Device can Rotate from "Top in" to "Top Out":

Design 2 is configured to rotate from its "default" configuration to an effective "top out" configuration. Design 2 would have the capability to rotate to an effective "top in" configuration. Such a capability would likely require the removal of part or all of the vertical static member, because the subject would need to be standing in the space that would otherwise be occupied by this component. Design 2 is adapted and configured to accomplish an effective "top in" configuration by requiring the subject to rotate 180 degrees with respect to the device.

Measuring the Motion of Other Artificial Structures within a Joint:

In most instances there is no differentiation between naturally occurring and artificial structures within a joint, however in some methods and apparatus for measuring the motion of specific artificial structures within a joint, such as a prosthesis or a bullet.

Providing a "Pain Indicator" Input Capability for the Subject:

The devices and systems can be adapted and configured so that the subject can indicate the points during the joint motion that corresponds to specific types of pain, a well as an ability to input to the apparatus the magnitude and duration of the pain. Such information would be assimilated into the diagnostic results provided by the present invention for the purpose of better diagnosing joint problems and performance issues.

Different Types of Applied External Forces:

The horizontal, vertical and "butterfly" motion control devices all have the optional capability to engage a motor or piston generate and transmit external forces to the motion platform/member during testing. These forces act on the motion platform/member in either a linearly or a rotationally directed way. Such forces could act axially or in other linear directions that are not contemplated in the preferred embodiment, specifically in linear directions not parallel to the plane of the motion platform/member. These forces could be created by attaching weights directly to the subject and or the motion platform/member, and this weight could be attached via a system of cables, pulleys, and supporting structures such that the direction and magnitude of the force created by this weight could be controlled and directed. Such external forces, in the case that such a system is used, could be measured by use of a strain gauge.

Other Diagnostic Imaging Systems:

The present invention contemplates a compatibility with all types of diagnostic imaging that are capable of producing moving images of joint motion. The method typically utilizes videoflouroscopy technology, CT scans, and magnetic resonance imaging. However, other diagnostic imaging methods such as ultrasound imaging, and imaging methods not yet invented could also be utilized. In addition, three-dimensional imaging platforms could be employed if the motion control devices had the capability to move along a three dimensional surface, as opposed to within a two dimensional plane, as is contemplated in the preferred embodiment of the motion control device. One skilled in the art will appreciate that as additional medical scanning or diagnostic devices become available, the present invention can be adapted to accommodate them.

Other Muscle Involvement Diagnostic Systems:

The present invention contemplates the use of surface electromyography for the measurement of muscle involvement, however other diagnostic systems may be used as well in an alternative embodiment such as MRI and ultrasound or other technologies not yet invented. These other diagnostic systems may or may not be sensor based. One skilled in the art will appreciate that as additional medical scanning or diagnostic devices become available, the present invention can be adapted to accommodate them.

Other Interpretation Methodologies Other than Those Listed in the Third Aspect of the Invention:

The present invention contemplates a fourth and fifth aspects, which are the specification of methodologies for interpreting the measurements provided by the present invention to generate diagnostic results that can be clinically applied in the treatment of subjects with joint problems or performance issues. While these fourth and fifth aspects are necessary for reducing to practice the diagnostic apparatus and methods given in the first, second and third aspects of the invention, these aspects may be alternatively embodied by other interpretation methodologies that can be applied to the diagnostic measurements afforded by the apparatus and method of the present invention. These might include applications of the diagnostic measurements outside of the boundaries of validation that are provided for through controlled clinical trials using the diagnostic apparatus and method. These might also include less structured interpretation methodologies, and methodologies applied by practitioners other than therapists, physicians, surgeons, chiropractors, veterinarians, and other health professionals.

Diagnostic Use of Other Drugs:

The present invention contemplates the optional diagnostic use of muscle relaxant drugs such as metaxalone or diazepam, systemic pain drugs such as oral opioid drugs, and/or local pain drugs such as transdermal lidocaine. In an alternative embodiment of the invention, different drugs other than those listed in the preferred embodiment might be shown to demonstrate a diagnostically useful result, and therefore might become a part of the operation of the present invention.

Exclusion of Measurements that are Proven to not be Important:

Certain measurements contemplated in the preferred embodiment have not yet been validated as providing any diagnostic value. For example, measuring electromyography might be shown not to be necessary to perform during every testing event. This could happen if electromyography readings are shown to be negligible in lying down passive side bending of the spine, for example. If this is the case, it could prove to be unnecessary to measure electromyography during motion studies that involve lying down passive side bending. Alternative embodiments of the apparatus could exclude certain measurements in certain configurations if such measurements are demonstrated to be measurable by proxy, or to be of very limited clinical and/or diagnostic value.

The Measurement of Other Joint Motion Parameters not Contemplated in the Preferred Embodiment:

The joint motion parameters that determine the apparatus configurations contemplated in this application are those that can be described as being: (1) weight-bearing or non-weight-bearing, (2) with or without the involvement and measurement of external forces, (3) involving or not involving pain-associated muscle involvement, and (4) involving or not involving systemic reductions in overall muscle activity. The preferred embodiment of the diagnostic method of the present invention will involve not only the configurations to accommodate the above-mentioned motion parameters, but also will possibly contemplate other motion parameters not listed above.

V. EVALUATION TECHNIQUES

The methodology specified below puts forward a method to utilize the present invention to assess the extent of dysfunctionality of specific muscles that could be suspected of causing joint pain or performance problems. The process listed below can be applied to any joint in humans and animals with internal bony skeletons, and should be applied to any given joint in any given type of organism before conclusive diagnostic results regarding that joint in that organism can be derived from measurements based on the present invention. According to the present invention there is provided the specification of a methodology for utilizing all or any one or combination of the horizontal, vertical and "butterfly" motion control devices in a diagnostic measurement process that also involves the collection of surface electromyography (sEMG) measurement signals taken from sEMG sensor electrodes that are placed on the subjects body prior to the initiation of this diagnostic measurement process. The measurements provided by the present invention can be used to derive quantitative assessments of the "dysfunctionality" of muscles that attach to and are proximal to the internal joint structures of interest. This information can be used diagnostically either with or without the additional measurements of joint surface motion and measurements of the motion of internal joint structures. The below listed process contemplates the use of the horizontally configured motion control device, the vertically configured motion control device, and/or the "butterfly" motion control device, however variations and adaptations of the below listed process could be required, such as the use of any one, two or all three of the devices together.

The process is:

a. For any given joint, assessing the involvement of muscles during joint motion for the purpose of detecting muscle dysfunction by using either the vertical, horizontal or "butterfly" motion control devices in conjunction with sEMG either before, during, or after acquiring images with the imaging device.

b. Begin by recording the joint muscle activity and by attaching sEMG electrodes to the subject in near proximity to the specific vertebrae that are being investigated and by using a standardized protocol to ensure consistent placement across subjects, and by attaching the subject to the vertically configured motion control device 27 in the standing weight-bearing position or alternatively by attaching the subject to the "butterfly" motion control device 29 configured to a full upright configuration. Instruct the subject to actively bend his or her trunk in flexion/extension or side bending to the maximum voluntary angle in the absence any powered assistance or resistance coming from the device. For these motions, the external force system 39 is disengaged and the trunk bending angle data from the vertically configured motion control device is synchronously recorded with the sEMG signals that are measured during the trunk bending. Parameterize the sEMG signals from this motion sequence into a single number or index, and this parameterized variable is referred to as $EMG_{Active, WB}$.

c. Have the subject return to the neutral position then engage the external force system to produce a known and measured resistive force acting in the direction opposite the bend and also acting against the subjects own motive muscle forces for the purpose of providing a resistive load against the subject's bending. Instruct the subject to bend against the load such that the load is overcome and the subject can initiate the bend. Instruct the subject to stop bending at the midway point through the bend, and to hold this position such that the subject's muscular forces are in isometric opposition to the resistive load forces transmitted by the vertically configured motion control device. Record the sEMG signals and the magnitude of the resistive load while the subject holds this isometric posture.

d. Use the known force parameter as well as a parameterization of the recorded sEMG signal from the above step to calculate a force/sEMG scaling parameter that can be used to correlate any parameterized sEMG measurement to a specific force parameter for any sEMG measurement from any given subject. Use this scaling parameter to express all parameterized sEMG measurements in terms of the muscular forces that they are associated with. This scaling parameter is referred to as $SF_{EMG-Force}$. It may be necessary in some instances to conduct this measure $SF_{EMG-Force}$ at different known force levels within the same subject to establish the linearity of the force/sEMG relationship, or alternatively to collect data points required to interpolate a non-linear scaling function in the case that this relationship is not predominately linear.

e. With the subject still attached to the vertically configured motion control device 27 or to the "butterfly" motion control device 29, configure the external force system 39 to provide passive motion for the subject, wherein the device provides the motive forces required to move the subject through their trunk bend. Have the subject practice this passive motion while simultaneously observing the sEMG signals that result. Repeat these practices until the sEMG signal ceases to change from one practice passive bend to the next. Once the steady-state sEMG signal has been achieved, have the subject execute a passive bend while recording the sEMG signal. The parameterized sEMG signal from this bend is referred to as $EMG_{passive, WB}$.

f. Detach the subject from the vertically configured motion control device and attach the subject to the horizontally configured motion control device 25 or alternatively by attaching the subject to the "butterfly" motion control device 29 configured to a full horizontal configuration. sEMG sensors should remain unmoved and operational during this change of devices. Disengage the external force system 39 and instruct the subject to bend themselves through their maximum voluntary bending angles. During this bend trunk bending angle data from the vertically configured motion control device is synchronously recorded with the sEMG signals that are measured during the trunk bending. Parameterize the sEMG signals from this motion sequence into a single number or index, and this parameterized variable is referred to as $EMG_{Active, Non-WB}$.

g. With the subject still attached to the horizontally configured motion control device 25 or to the "butterfly" motion control device 29, configure the external force system 39 to provide passive motion for the subject, wherein the device provides the motive forces required to move the subject through their trunk bend. Have the subject practice this passive motion while simultaneously observing the sEMG signals that result. Repeat these practices until the sEMG signal ceases to change from one practice passive bend to the next. Once the steady-state sEMG signal has been achieved, have the subject execute a passive bend while recording the sEMG signal. The parameterized sEMG signal from this bend is referred to as $EMG_{passive, Non-WB}$.

h. Compute nine quantities, and compare these quantities to those within a demographically stratified normative database of values for the exact same computed values derived from the exact same measurement process and conducted within a specifically defined population of subjects, such as subjects that are pain free, or subjects that have definitively diagnosed muscular pain, etc.

a. $Force_{Active, WB} = (EMG_{Active, WB}) \times (SF_{EMG-Force})$
  b. $Force_{Passive, WB} = (EMG_{passive, WB}) \times (SF_{EMG-Force})$
  c. $Force_{Active, Non-WB} = (EMG_{Active, Non, WB}) \times (SF_{EMG-Force})$ d. $\text{Force}_{Passive,Non-WB} = (\text{EMG}_{Passive, Non,WB}) \times (\text{SF}_{EMG\text{-}Force})$ f. $\Delta(\text{Active-Passive})_{WB} = (\text{Force}_{Active,WB}) - (\text{Force}_{Passive,WB})$ g. $\Delta(\text{Active-Passive})_{Non-WB} = (\text{Force}_{Active,Non-WB}) - (\text{Force}_{Passive,Non-WB})$ h. $\Delta(\text{WB-NonWB})_{Active} = (\text{Force}_{Active,WB}) - (\text{Force}_{Active,Non-WB})$ i. $\Delta(\text{WB-NonWB})_{passive} = (\text{Force}_{Passive,WB}) - (\text{Force}_{Passive,Non-WB})$ j. $\Delta(\text{MAX-MIN}) = (\text{Force}_{Active,WB}) - (\text{Force}_{Passive,Non-WB})$ i. Use statistical results such as the Percentile within a specific subject population described above to determine if a specific set of values for the above listed set of computed values should be considered normal or dysfunctional. This determination will be made by assigning some statistical threshold, for example 95%, for the purpose of providing a quantitative basis for assessing the presence of muscle dysfunction. If a specific set of values is deemed dysfunctional, then that result must accompany any reports of joint surface motion or reports of the motion of internal joint structures, because then it would be possible that any observed motion dysfunction could be caused by an underlying muscular dysfunction. However if a specific set of values is deemed functional, then that too must accompany any reports of joint surface motion or reports of the motion of internal joint structures, because if "non-dysfunctional" muscular activity is observed then muscle dysfunctions can be ruled out as a potential cause of any observed motion dysfunction. Being able to rule out muscle dysfunctions for subjects in which motion dysfunctions have been observed is extremely useful to clinicians because this can be the basis to indicate one therapy over another, such as indicating non-surgical therapy over surgical therapy.

j. By using these measurements taken at different points in time over a specific time period, it will be possible to determine the extent to which any observed muscle dysfunctions are improving, staying the same, or getting worse. Such observations can be used to assess the "irreversibility" of muscle dysfunctions by correlating any changes to a motion function over time with any specific therapeutic regimen.

k. The results of the above process can be used by the prescriber to determine the exact configuration of the imaging studies, for example.

Heretofore, the above-listed process would have been impossible and it is only the innovation afforded by the first, second and third aspects of the invention that provides for the practicality of this fifth aspect of the invention. It has been the intention of this inventor to develop a diagnostically useful result as a result of the above-listed process, and these requirements then served as the design objectives in the development of the designs for the apparatus and diagnostic method.

The diagnostic method of the present invention requires two different operational processes. There is that process that must be executed for each new test that is prescribed, a description of which directly follows this paragraph, and that process that needs to be done only once during the initial installation, or possibly thereafter after long intervals of usage. This latter process is the apparatus calibration process and is required to initialize the hardware configuration of the apparatus to be compatible with a given testing environment, and also initializing the hardware and software computing processes that are required to enable the flow of testing measurement data between and among the various apparatus components as described in this specification. This calibration process is not described in detail in this specification, as it is highly variable and specific to each testing environment. However the testing process that must be done for each testing subject is given in detail below.

The process that must be done for each testing subject is as follows:
1. Qualify Diagnostic Testing Candidates
2. Prescribe specific testing configuration or configurations
3. Configure Testing Apparatus
4. Perform Testing and Process Results Each of the above listed process steps is described in detail in the following paragraphs.

Qualify Diagnostic Testing Candidates:

Currently, a subject would be considered a testing candidate if:

a. The subject has a joint problem or performance issue b. The limitations created by the subject's joint problem justify the prescription of a diagnostic test that could involve minimally invasive procedures such as videoflouroscopy/CT scans and/or the administration of pain and/or muscle relaxant drugs c. The subject is able to move the problem joint or have the problem joint moved to a sufficient degree that the motion will be detectable in moving diagnostic images Prescribe Specific Testing Configuration:

The process of prescribing a specific testing configuration currently contemplates a prescription algorithm that involves several questions, which are:

a. Which joint needs to be examined, in which plane of motion, and through which motion?

b. Should the plane of the fixated body part be at an angle to the plane of the rotated body part?

c. Should the motion be weight-bearing or non-weight-bearing, or both?

d. Should the subject be in a bent posture, and if so how?

e. Should the motion be active or passive on the part of the subject, or both?

f. Should the motion involve externally generated forces, and if so what kind?

g. Does pain-associated muscle activity need to be masked?

h. Does systemic muscle activity need to be reduced?

i. Will both electromyography measurement as well as imaging data be collected, or is only one of these types of data collection required?

Answering the above-listed questions will yield the specific configuration parameters for the testing apparatus. Currently, there are no investigational data from controlled clinical trials to assist prescribers in answering the above-listed questions. It will only be through the investigational use of the present invention that these questions will be answerable. Therefore for the purpose of this application these diagnostic questions are listed, however the specific clinical insights required to answer them are not included.

Configure Testing Apparatus:

Depending on the outcome of the previous process step in which a specific testing configuration is prescribed, there could be one of several configurations. There are several configuration parameters that, when taken as a group, determine the exact configuration of the testing apparatus. These configuration parameters are:

a. Posture: Subject can assume a lying, sitting, bent, or standing posture, determined by whether normal, modified, or non-weight-bearing motion is required by prescriber.

b. Use of posture assistance devices: Whether or not posture assistance devices will be used is a function of which type of joint and which type of joint motion is being studied. The posture assistance devices are required when adjustments to patient position are required to keep the vertebrae of interest as orthogonal to the line of imaging as possible.

c. Motion parameters: The starting point and ending point, in degrees and/or units of length, and the velocity parameters of the specific joint surface motion that is being studied.

d. Plane of motion: The plane containing the specific joint motion that is being studied.

e. Joint Orientation: Orientation of subject's joint with respect to the plane of motion that is being studied f. Involvement of external forces: For horizontal and vertically configured motion control devices, if and how the external force system 39 from FIG. 3 is engaged or disengaged to produce the external forces required by the prescriber.

g. Electromyography measurement: Measure electromyography for muscles involved in joint motion h. Other electric sensor based measurements: Measure other physiological parameters associated with the joint motion and/or underlying fluid dynamics?

Perform Testing and Process Results:

To perform the test, a trained operator operates the configured apparatus to record all images and measurements. If so prescribed by a physician, the subject may be administered muscle relaxant drugs such as metaxalone or diazepam, systemic pain drugs such as oral opioid drugs, and/or local pain drugs such as transdermal lidocaine; the administration of which is for purely the diagnostic purpose of altering the subject's pain and muscle activity in a specific way during testing and image generation.

If specific muscle studies are indicated, then these muscle studies are conducted either before, during, or after the imaging process begins. Once all images and data have been collected and the testing is complete, the next steps are to process these images and data to produce diagnostic measurements, interpret these diagnostic measurements to produce diagnostic results, and transmit these results to the operator and/or the prescriber. The above steps are all accomplished through the normal utilization of existent machines from the prior art such as computers and computer networks and require no specific explanation other then the detail given already in this specification section and in the previous discussions of FIG. 1.

The images obtained from the imaging device can, if required, be scaled, prior to analysis to remove inherent distortions or magnifications in that device's image field by the use of corrective geometric transformations in the analysis software. Furthermore, the accuracy of measurement of rotational or translational position and motion data during analysis can be determined by pre-calibration using realistic preset calibration models of the relevant joints. Lastly, the reliability of measuring joint motion parameters using the device in its various configurations, between and within operators and within individual subjects, can be achieved by repeated analysis and/or acquisition of data and image sequences.

FIGS. 19A-D illustrate experimental results from a muscle function study that provide case study data to support the clinical viability of the present invention's capability to detect muscle dysfunction. The sEMG data presented in FIGS. 19A-B were taken from a normal healthy subject confirmed to be free of back or neck pain as the subject performed flexion/extension bending in FIG. 19A and side bending in FIGS. 19B. In both FIGS. 19A-B the sEMG signal is completely eliminated as the subject changes from active weightbearing bending to passive non-weightbearing motion. This same result has been broadly observed across a population of multiple pain free subjects, indicating that the ability to effectively quiet muscle activity by mechanically disengaging weightbearing and motive force-providing muscles is one that should be considered as being within normal physiologic function. The sEMG data presented in FIGS. 19C-D were taken from a patient with chronic back pain as the patient performed flexion/extension bending in FIG. 19C and side bending in FIGS. 19D. In both FIGS. 19C-D the sEMG signal cannot be eliminated as the subject' weightbearing and motive force-providing muscles have been mechanically disengaged, indicative of residual muscle activity where normally there would be none. Such a result is exactly what would be expected in the case that "muscle guarding" is indeed a clinically detectable spine muscle dysfunction. The sensors were placed on the skin corresponding to the right and left erector spinae respectively.

VI. HYPOTHETICAL EXAMPLES

Using the devices and methods of the invention facilitates the detection and analysis of a variety of spinal kinematic dysfunctions. Additionally, the invention facilitates determination of the suitability of a subject for an orthopedic procedure. The devices and methods of the present invention enable measurements of spinal kinematics with a precision of less than ±5°, preferably less than +3° and more preferably less than +1°.

Example 1

Detection of Pseudarthrosis

Pseudarthrosis is the condition that results from a "failed" spinal fusion, wherein there is motion in a fused spinal joint where there should be none. Because of the +5° precision of current measurement methods, the United States Food and Drug Administration advocates the standard that there can be no definitive diagnosis of pseudarthrosis unless observed Range of Motion (ROM) is 5° or greater. However there are many suspected cases of pseudarthrosis where there is observable motion, however this motion is less than 5°. With the present invention, there could be definitive detection of pseudarthrosis with any observed motion of greater than 1°. This will dramatically reduce the number of inconclusive results, which today occur with any cases where observed motion is between 1-4°. Alternatively pseudarthrosis could be more definitively ruled out in all cases where the observed motion is less than 1°, whereas ruling out pseudarthrosis is currently impossible, as immobility cannot be definitively detected with the current measurement methods.

Example 2

Level-Specific Detection of Hypermobility

When patients are suspected of having spondololysthesis, spinal kinematic studies are prescribed to measure the ROM using traditional flexion/extension X-rays with the intention of detecting if a joint is "hypermobile", in which case spondololysthesis may be diagnosed. The current medical practice in the United states when spondololysthesis is suspected is to perform a spinal kinematic study to determine if the observed ROM is greater than 11° of rotation or 4 mm of translation. If such a diagnostic result is observed in a patient, surgery is often indicated. This same threshold applies to all vertebrae, no matter whether they are in the lumbar, thoracic, or cervical spine. However it is well-documented that the normal physiologic ROM varies by 300% between different levels (for example, among healthy patients mean ROM at L5/S1 is 5° whereas at L1/L2 it is 15°). The improved precision afforded by the present invention allows for level-specific thresholds of Hypermobility to be defined based on a statistical definition (i.e. defining 5% outliers as hypermobile), rather than the "one sized fits all" approach that is not statistically-based as is the case with the current standard of care. With the current standard of care, it is reasonable to assume that many patients are misdiagnosed because the thresholds are somewhat arbitrary and do not account for the physiologic variation that is known to exist across in ROM across different vertebrae. This misdiagnosis leads both to unnecessary surgeries (in the case of false positive results) and non-treatment of a surgically-treatable condition (in the case of false negative results)

Example 3

Detection of Vertebral Stiffness

With the current standard of care that has a precision of ±5°, it is impossible to detect stiffness. However with the present invention, stiffness has been detected among degenerative disc disease sufferers and has been observed to be absent among normal healthy volunteers. If a subject presents with stiffness, this could have very serious ramifications for the surgeon. If a surgeon were to be considering an artificial disc for a patient with confirmed stiffness, the surgeon would have to have confidence that it is the disc, not the environment around the vertebrae, that is causing the stiffness. Currently this is impossible to determine, but with the present invention such data would be available and would affect whether or not artificial discs would be indicated for patients suffering from intervertebral stiffness.

Example 4

Detection of Paradoxical Motion

With the current standard of care, paradoxical motion (motion in which the bones move in the opposite direction of the trunk bend) has never before been observable. The present invention can definitively detect paradoxical motion, and has shown this condition to be highly prevalent among back pain sufferers while it has been observed to be completely absent from normal healthy volunteers. The detection of paradoxical motion would be a very strong indication for the need for spine stabilization surgery, as it indicates a complete breakdown in the elastic-restraint function of the spinal disc and therefore can be interpreted to be a structural failure within the disc.

Example 5

Ability to Observe Motion "During the Bend"

With the current technology, only two images corresponding to the extremes of bending are measured, and no data is collected "during the bend". Because of this, it is only possible to detect spinal kinematic dysfunctions associated with how far the bones move, and it is impossible to detect and spinal kinematics dysfunctions associated with how the bones move. The present invention has been shown to detect spinal laxity, in which the vertebrae move to their proper end ranges, but do so in a way that appears to be unrestrained. Normal healthy motion of the vertebrae occurs smoothly as a result of the stretchy/springy function of the spinal discs. With this normal healthy motion, the vertebrae move in direct proportion to the trunk bending. With laxity, the vertebrae move immediately to the end positions as soon as trunk bending commences, then remain unmoved during the majority of the bend, then move quickly back to the normal positions as the trunk is returned to a neutral position. Such motion indicates that the elastic-restraint function of the disc has been compromised, which could indicate the need for spine stabilization surgery. Laxity is undetectable with the current standard of care because it is only apparent during the bend, where no measurements are taken with the current measurement methods.

Example 6

Muscle Involvement Obscuring a Kinematic Dysfunction

A patient presents with severe chronic back or neck pain that has been non-responsive to conservative therapy for 6 months. The orthopedic surgeon or neurosurgeon orders a spinal kinematic study by measuring ROM by taking flexion and extension X-rays. The ROM measurement is within normal range, meaning that it is not measured to be greater than 11 degrees/4 mm of motion. With the current paradigm, this patient would not be a candidate for spine stabilization surgery. One of the main benefits of the present invention is its ability to measure the same patient through the same motion in normal standing motion and then to measure the same patient in abstracted motion (lying down passive motion) in which muscle involvement has been minimized. With the present invention, this patient is shown to have motion that is normal during standing active motion in which the muscles are engaged, but is shown to be hypermobile when the muscles are disengaged during lying down passive motion. This result shows that the muscle involvement was obscuring what is a clearly detectable instability, and surgery is therefore potentially be indicated to treat kinematic dysfunction that is obscured by muscle involvement.

Example 7

Muscle Involvement Causing a Kinematic Dysfunction

A patient presents with severe chronic back or neck pain that has been non-responsive to conservative therapy for 6 months. The orthopedic surgeon or neurosurgeon orders a spinal kinematic study using the present invention, which detects a surgically treatable motion dysfunction such as paradoxical motion or laxity. This patient's muscles are then tested using the present invention by first measuring the surface electromyographic readings from the patient while the patient is performing normal standing trunk bends. This test shows that the muscles are firing as normally would be expected. Second, the patient's surface electromyographic readings are measured during lying down passive motion, and in this movement the readings should be zero. However this patient shows abnormally high muscle involvement where there should be none, thus indicating the presence of pain-induced "muscle guarding". The presence of this muscle guarding indicates that the observed spinal kinematic dysfunction is potentially caused by the muscle guarding, which itself evolved within the patient as a result of the pain. Therefore surgery could potentially not be indicated because the kinematic dysfunction can be shown to potentially be a symptom, not a cause of the underlying pain.

Example 8

Detecting Soft Tissue Injuries

A patient presents with severe chronic back or neck pain that has been non-responsive to conservative therapy for 6 months. The orthopedic surgeon or neurosurgeon orders a spinal kinematic study using the present invention, which detects no observable kinematic dysfunctions in lying or standing motion, so instability of the spine can be ruled out. The subjects muscle involvement is tested, and it is shown that the patient's muscles remain active even when the patient is being passively bent while lying down (during which normal subjects would have no muscle activity). This result would indicate that: (1) surgery should be ruled out, (2) there is a muscle dysfunction that is either causing or being caused by the pain. Physical therapy and core muscle training could be indicated to determine if the muscle dysfunction can be eliminated. If the muscle guarding proves to be intractable, then surgery could possibly be indicated. If the muscle guarding can be eliminated, then it can be determined if the muscle guarding was causing or being caused by the pain.

Example 9

Exclusion of Soft Tissue Injuries

A patient presents with severe chronic back or neck pain that has been non-responsive to conservative therapy for 6 months. The orthopedic surgeon or neurosurgeon orders a spinal kinematic study using the present invention, and all known kinematic dysfunctions and muscle dysfunctions are definitively ruled out as a potential cause of the severe chronic back or neck pain. The value of the present invention is to definitively detect when a patient should not have surgery or be referred for physical therapy, by definitively detecting the ABSENCE of the specific kinematics and/or muscle dysfunctions those therapies are targeted to address. This would dramatically reduce the cost and increase of efficacy of treatment for "soft tissue injuries".

As a result of the devices, methods and systems, the detection of joint functional derangements in certain subjects for whom approaches based on the prior art have failed to definitively detect any particular joint defect as being the cause of the joint problem is achieved. This enables patients who would otherwise have no good diagnostic results on which to base treatment decisions. Additionally, quantitative measurements of the relationship of joint surface motion and force to the motion of and between specific internal joint structures, such as bony structures and other structures beneath the skin that form the joint are achieved. These measurements can be used for the detection of joint functional derangements, by defining specific ranges of measurement parameters that are generally present in subjects with specific joint functional derangements, and that are generally absent in normal healthy subjects, or vice versa, such that the measurements themselves can be applied diagnostically to detect joint functional derangements with a degree of statistical confidence and diagnostic accuracy that would be considered by joint experts as being at least adequate based on the performance levels of comparable clinically-available methods that have been put forward the prior art.

The measurements can also be used to produce quantitative measurement in a way that accommodates and addresses the possible involvement of muscles in joint motion such that diagnostic interpretations of such measurements are not second-guessed and discounted by joint experts due to their concerns regarding either the validity of diagnostic results derived from studies involving non-natural joint motion, nor by their concerns regarding the high degree of inherent variability in the measurements of uncontrolled joint motion, nor by their concerns that muscle guarding or other types of muscle involvements could be responsible for any observed motion dysfunctions, by, for example, affording detection of joint muscle dysfunction by measuring abnormal muscle activity in a subject, such that the detection of abnormal muscle activity as compared to a "normal" subject population would suggest the presence of muscle guarding behavior, and with the understanding that with this ability to specifically determine that a joint dysfunction is potentially caused by any observed muscle dysfunction, there is better information with which to formulate an appropriate treatment strategy; affording differentiation between three unique muscle types; motive muscles, weight-bearing muscles, or the combination of thereof, and for determining which of these three types of muscle types could be responsible for any observed muscle dysfunction through the use of electromyography in conjunction with a motion apparatus that provides the ability to isolate each group independently, by: minimizing or eliminating the involvement of motive muscles during joint motion through the use of the present invention by allowing for electromyographic readings to be taken while performing controlled, standardized, and measured motion under the force of the subject's own motive muscles, which is called active motion in this application, but that can also optionally provide for passive motion on the part of the subject by providing for a motorized external force to act on the subject to affect the joint motion, such that if the subject is not able to "silence" motive muscle electromyographic signals after practicing passive motion, it is assumed that such signals are an artifact resulting from muscle guarding, and thus a muscle dysfunction; and minimizing or eliminating the involvement of weight-bearing muscles, provided the joint is a weight-bearing joint, during joint motion through the use of the present invention that allows for electromyographic reading to be taken while in either a weight-bearing posture, or a non-weight-bearing posture through the use of a device which can optionally include or exclude the need for the subject to use weight-bearing muscles in affecting a controlled, standardized, and measured joint motion by providing an apparatus that is configurable to position the subject in either type of posture, such that if the subject is not able to "silence" weight-bearing muscle electromyographic signals after practicing non-weight-bearing motion, it is assumed that such signals are an artifact resulting from muscle guarding in the weight-bearing muscle group, and thus a muscle dysfunction; measuring the "entrenchment" of any observed muscle guarding in the event that muscle guarding is detected in one of the three muscle groups, by observing and measuring the ability and rate at which a subject is able to minimize the magnitude of observed electromyographic signals associated any observed muscle dysfunction through the repeated practicing of controlled, standardized motions for which the involvement of one or more specific types of muscles has been minimized or eliminated, such that this measurement of the rate of change of electromyographic signals taken over the course of repeated practicing of controlled, standardized, muscle-minimized motion can be used to produce a diagnostic assessment of the statistical probability that the muscle guarding behavior should be considered reversible or irreversible, and thus, which treatment strategy would provide the best outcome for the subject, by comparing any given subject's measurement parameters to a normative database of measurements taken from other subjects who have been confirmed to have "non-entrenched" muscle guarding; producing and linking in time said quantitative measurements to quantitative measurements of muscle activity, either by validating the use of joint motion measurements as a proxy for the measurement of muscle activity through the creation of investigational data from controlled clinical trials that involve the use of the present invention that correlate specific muscle activity patterns as measured using electromyography to specific types of joint motion as measured with the apparatus contemplated with the present invention, or alternatively, if said proxy is demonstrated to be invalid, affording a mechanism to directly measure muscle activity with electromyography in addition to the imaging and other measurements that would normally be conducted as part of the usual diagnostic testing process contemplated with the present invention; accounting for the involvement of pain-associated muscle activity in joint motion, by providing a clinically-validated methodology for using the present invention in combination with the diagnostic and not therapeutic use of approved and commercially-available systemic pain drugs such as oral opioids and/or local pain drugs such as transdermal lidocaine to mask the joint pain felt by the subject as the subject performs joint movements during image generation for the purpose of minimizing the irregularities cause by pain-associated muscle contractions during image generation; and accounting for systemic reductions in overall muscle activity, by providing a clinically-validated methodology for using the present invention in combination with the diagnostic and not therapeutic use of approved and commercially-available muscle relaxant drugs such as metaxalone or diazepam to reduce the overall level of muscle activity within the subject as the subject performs joint movements during image generation.

Additionally, the devices, methods and systems enable detection of joint dysfunction in an isolated plane that is neither a "full" non-weight-bearing nor "full" weight-bearing plane of movement, where it is understood that "full" non-weight-bearing motion occurs when a subject moves in the plane that is normal to gravitational force, while "full" weight-bearing motion occurs in the plane that is parallel to gravitational forces, by providing a motion apparatus that affords for controlled, standardized, measured joint motion to occur in a plane that is neither "full" weight-bearing nor "full" non-weigh-bearing, but rather at some angle in between; detecting joint dysfunction in one or more isolated planes, that is either a "full" non-weight-bearing or "full" weight bearing plane, or in any plane in between the "full" non-weight-bearing and "full" weight-bearing plane; and simultaneously measuring the motion of internal joint structures, surface joint motion and muscle activity at the exact same time so as to provide a time-synchronized set of diagnostic parameters that affords for a comparative analysis to be conducted among the measurement parameters for any given point in time during the joint motion.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus adapted and configured to externally control an articulation of a joint motion of a patient comprising:
    a) a base positioned in a first base plane;
    b) a fixable platform adapted and configured to engage the base at an attachment mechanism, the fixable platform having a first position in a first fixable platform plane and being fixably adjustable to a second position;
    c) a dynamic platform having a first position in a first dynamic platform plane, and being adjustable about a first axis to a second position and selectively rotatable about a second axis;
    d) a coupling member adapted and configured to connect the fixable platform to the dynamic platform or the base; and
    e) a sensor unit configured to sense the joint motion of the patient during motion of the dynamic platform.

2. The apparatus of claim 1, wherein the apparatus is in communication with one or more medical diagnostic devices selected from the group consisting of X-ray scanner, X-ray tube with image intensifier tube, magnetic resonance scanner, infrared camera, computed tomography scanner, ultrasound scanner, electromyography sensor unit, digital camera and camera.

3. The apparatus of claim 2, wherein the one or more medical diagnostic devices are detachably connected.

4. The apparatus of claim 2, wherein the one or more medical diagnostic devices are one or more electromyography sensor units with sensors attachable to the patient.

5. The apparatus of claim 2, wherein the one or more medical diagnostic devices further comprise at least one sensor for capturing data.

6. The apparatus of claim 1, further comprising a lock for locking a position of the plane of the dynamic platform relative to the base.

7. The apparatus of claim 1, further comprising a lock for locking a position of dynamic platform in at least one position relative to the static platform.

8. The apparatus of claim 1, further comprising an actuator coupled to the dynamic platform, wherein the actuator applies force on the dynamic platform.

9. The apparatus of claim 1, further comprising an emergency actuator stop button wherein the actuator can be stopped from applying force on the dynamic platform by activation of the emergency actuator stop button.

10. The apparatus of claim 9, wherein the actuator is actuated by the patient.

11. The apparatus of claim 1, further comprising a lock for locking a position of the static platform in at least one position relative to the base.

12. The apparatus of claim 1, wherein the first plane of the base is one of horizontal or vertical.

13. The apparatus of claim 1 wherein the fixable platform is actuated by a user.

14. The apparatus of claim 1 wherein the dynamic platform is actuated by a user.

15. The apparatus of claim 1, further wherein the one or more medical diagnostic device is connected to the base or the static platform.

16. The apparatus of claim 1, wherein the base is a support frame.

17. The apparatus of claim 1, wherein the dynamic platform is adapted and configured to move automatically, semi-automatically, or manually.

18. The apparatus of claim 1, further comprising one or more radiopaque markers positioned within an imaging field of the apparatus.

19. The apparatus of claim 1, further comprising a stabilization member adapted and configured to support the base.

20. The apparatus of claim 1 wherein the sensor unit is configured to sense a force of the dynamic platform.

21. A process for capturing data and controlling skeletal joint motion of a subject comprising:
   (a) providing an apparatus adapted and configured to selectively control an articulation of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable about a first axis to a second position and selectively rotatable about a second axis, a coupling member adapted and configured to connect the fixable platform to the dynamic platform or the base, and a sensor unit configured to sense the joint motion of the subject during rotation of the dynamic platform, and in data communication with at least one medical diagnostic device, wherein the apparatus is adapted and configured to collect data from the at least one medical diagnostic device;
   (b) positioning the subject in a first position such that a first body part of the subject is at least partially positioned adjacent the static platform, and a second body part of the subject is at least partially positioned adjacent the dynamic platform;
   (c) capturing, with the at least one medical diagnostic device, a first diagnostic data from the subject and the apparatus;
   (d) automatically repositioning the apparatus such that the subject is placed in a second position different from the first position; and
   (e) capturing, with the at least one medical diagnostic device, second diagnostic data from the subject and the apparatus in the second position.

22. The process of claim 21, wherein the data capturing steps further comprise use of a medical diagnostic device selected from the group consisting of X-ray scanner, X-ray tube with image intensifier tube, magnetic resonance scanner, infrared camera, computed tomography scanner, ultrasound scanner, electromyography sensor unit, digital camera and camera.

23. The process of claim 21, wherein the data capturing steps further comprise use of an electromyography sensor unit with sensors attachable to the subject.

24. The process of claim 21, wherein diagnostic data from the subject further comprises capturing data from at least one sensor.

25. The process of claim 21, further comprising the step of administering a pharmaceutically active substance to the subject prior to capturing the first diagnostic data.

26. The process of claim 25, wherein the pharmaceutically active substance is an opioid substance.

27. The process of claim 25, wherein the pharmaceutically active substance is a muscle relaxant drug selected from the group consisting of baclofen, carisoprodol, chlorphenesin, chloroxazone, cyclobenzaprine, dantrolone, diazepam, metaxalone, methcarbamol and orphenadrine.

28. The process of claim 21, wherein the pharmaceutically active substance is a non-opioid analgesic.

29. The process of claim 28, wherein the non-opioid analgesic is fentanyl.

30. The process of claim 21 wherein the sensor unit is configured to sense a force of the dynamic platform.

31. A process for capturing data and controlling a skeletal joint motion of a subject comprising:
   (a) providing an apparatus adapted and configured to selectively control an articulation of a joint of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable to about a first axis to a second position and selectively rotatable about a second axis, a coupling member adapted and configured to connect the fixable platform to the dynamic platform or the base, a sensor unit configured to sense the joint motion of the subject, in communication with the platform and at least one medical diagnostic device, wherein the apparatus is adapted and configured to collect data from the at least one medical diagnostic device and the at least one of one or more sensors or data collection devices during rotation of the dynamic platform;
   (b) selecting, on the subject, a target skeletal joint for examination;
   (c) attaching at least one surface electromyography sensor to the subject in adjacent the target skeletal joint;
   (d) positioning the subject in a first position such that a first body part is at least partially adjacent the fixable platform, and second body part is at least partially adjacent the dynamic platform;
   (e) moving the target skeletal joint from the first position to a second position different from the first position; and
   (f) capturing data from the sensor while the apparatus and the target skeletal joint are in motion.

32. The process of claim 31, further comprising applying a predetermined constant resistive load force to the particular skeletal joint while the particular skeletal joint selected for examination is moving.

33. The process of claim 31, further comprising the step of administering a pharmaceutically active substance to the subject prior to capturing data.

34. The process of claim 33, wherein the pharmaceutically active substance is an opioid substance.

35. The process of claim 31, further comprising the step of capturing data using the at least one medical diagnostic device the medical diagnostic device being selected from the group consisting of X-ray scanner, X-ray tube with image intensifier tube, magnetic resonance scanner, infrared camera, computed tomography scanner, ultrasound scanner, and digital camera and camera.

36. The process of claim 35 wherein the step of capturing data from the sensor is performed concurrently with the step of capturing data using the medical diagnostic device.

37. The process of claim 31, wherein the pharmaceutically active substance is a muscle relaxant drug selected from the group consisting of baclofen, carisoprodol, chlorphenesin, chloroxazone, cyclobenzaprine, dantrolone, diazepam, metaxalone, methcarbamol and orphenadrine.

38. The process of claim 31, wherein the pharmaceutically active substance is a non-opioid analgesic.

39. The process of claim 38, wherein the non-opioid analgesic is fentanyl.

40. The process of claim 31 wherein the sensor unit is configured to sense a force of the dynamic platform.

41. An apparatus adapted and configured to detect soft tissue injury in a patient comprising:
   a) a base positioned in a first base plane;
   b) a fixable platform adapted and configured to engage the base at an attachment mechanism, the fixable platform having a first position in a first fixable platform plane and fixably adjustable to a second position;
   c) a dynamic platform having a first position in a first dynamic platform plane, adjustable about a first axis to a second position and selectively rotatable about a second axis;
   d) a coupling member adapted and configured to connect the fixable platform to the dynamic platform in a lockable arrangement in at least one plane;
   e) a sensor unit configured to sense a joint motion of the patient during motion of the dynamic platform; and
   f) one or more electromyography sensors adapted and configured to contact the patient at a target area wherein the electromyography sensors are in communication with at least one platform and at least one medical diagnostic device, wherein the apparatus is adapted and configured to collect data from the at least one medical diagnostic device and the at least one of one or more electromyography sensors during rotation of the dynamic platform, wherein the apparatus is adapted and configured to cooperate with at least one medical diagnostic device configured to capture data on the subject along with-at least one-electromyography sensor.

42. The apparatus of claim 41, wherein the at least one medical diagnostic device in data communication with the platform is selected from the group consisting of X-ray scanner, X-ray tube with image intensifier tube, magnetic resonance scanner, infrared camera, computed tomography scanner, ultrasound scanner, electromyography sensor unit, digital camera and camera.

43. The apparatus of claim 41, wherein the at least one medical diagnostic device is detachably connected to the apparatus.

44. The apparatus of claim 41, wherein the at least one medical diagnostic device further comprises at least one sensor for capturing data.

45. The apparatus of claim 41, further comprising a lock for locking a position of the dynamic platform in at least one position relative to the base.

46. The apparatus of claim 41, further comprising an actuator coupled to the dynamic platform, wherein the actuator applies force on the dynamic platform.

47. The apparatus of claim 46, further comprising an emergency actuator stop button wherein the actuator can be stopped from applying force on the dynamic platform by activation of the emergency actuator stop button.

48. The apparatus of claim 47, wherein the actuator is actuated by the patient.

49. The apparatus of claim 41, further comprising a lock for locking a position of the status platform in at least one position relative to the base.

50. The apparatus of claim 41, wherein the first plane of the base is one of horizontal or vertical.

51. The apparatus of claim 41 wherein the fixable platform is actuated by a user.

52. The apparatus of claim 41, further wherein the at least one diagnostic device is connected to the base or the fixable static platform.

53. The apparatus of claim 41, wherein the base is a support frame.

54. The apparatus of claim 41 wherein the sensor unit is configured to sense a force of the dynamic platform.

55. A method for detecting soft tissue injury in a subject comprising:
   (a) providing an apparatus adapted and configured to selectively control an articulation of a joint of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable about a first axis to a second position and selectively rotatable about a second axis, a coupling member adapted and configured to connect the fixable platform to the dynamic platform or the base, at least one of one or more sensors or data collection devices configured to sense a joint motion of the subject in communication with the platform and at least one medical diagnostic device, wherein the apparatus is adapted and configured to collect data from the at least one medical diagnostic device and the at least one of one or more sensors or data collection devices during rotation of the dynamic platform;
   (b) selecting, on the subject, a target skeletal joint for examination;
   (c) attaching at least one surface electromyography sensor to the subject in near proximity to the target skeletal joint;
   (d) positioning the subject in a first position such that a first body part is at least partially adjacent the fixable platform, and second body part is at least partially adjacent the dynamic platform;
   (e) manually moving the target skeletal joint from the first position to a second position different from the first position;
   (f) capturing data from the sensor while the apparatus and the target skeletal joint are in manual motion;
   (g) automatically moving the target skeletal joint from the first position to the second position different from the first position;
   (h) capturing data from the sensors while the apparatus and the target skeletal joint are in automatic motion; and
   (i) evaluating the data to determine whether a soft tissue injury exists.

56. The method of claim 55 further comprising the step of comparing sensor data captured while the apparatus and target skeletal joint are in manual motion to sensor data captured while the apparatus and target skeletal joint are in automatic motion.

57. The process of claim 55, further comprising applying a predetermined constant resistive load force to the particular skeletal joint while the particular skeletal joint selected for examination is moving.

58. The process of claim 57, further comprising applying a predetermined constant resistive load force to the particular skeletal joint while the particular skeletal joint selected for examination is moving.

59. The method of claim 55 wherein the sensor unit is configured to sense a force of the dynamic platform.

60. A method for assessing a subject's suitability for an orthopedic procedure comprising:
   (a) providing an apparatus adapted and configured to selectively control an articulation of a joint of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable about a first axis to a second position and selectively rotatable about a second axis, a coupling member adapted and configured to connect the fixable platform to the dynamic platform or the base, at least one of one or more sensors or data collection devices configured to sense a joint motion of the subject in communication with the platform and at least one medical diagnostic device, wherein the apparatus is adapted and configured to collect data from the at least one medical diagnostic device and the at least one of one or more sensors or data collection devices during rotation of the dynamic platform;

(b) selecting, on the subject, a target skeletal joint for examination;

(c) attaching at least one surface electromyography sensor to the subject in near proximity to the target skeletal joint;

(d) positioning the subject in a first position such that a first body part is at least partially adjacent the fixable static platform, and second body part is at least partially adjacent the dynamic motion platform;

(e) manually moving the target skeletal joint from the first position to a second position different from the first position;

(f) capturing data from the sensor while the apparatus and the target skeletal joint are in manual motion;

(g) automatically moving the target skeletal joint from the first position to the second position different from the first position;

(h) capturing data from the sensors while the apparatus and the target skeletal joint are in automatic motion; and (i) evaluating the data to determine the subject's suitability for an orthopedic procedure.

61. The method of claim 60 further comprising the step of comparing sensor data captured while the apparatus and target skeletal joint are in manual motion to sensor data captured while the apparatus and target skeletal joint are in automatic motion.

62. The process of claim 60, further comprising applying a predetermined constant resistive load force to the particular skeletal joint while the particular skeletal joint selected for examination is moving.

63. The method of claim 60 wherein the sensor unit is configured to sense a force of the dynamic platform.

64. A method for assessing a performance of an orthopedic procedure in a subject comprising:
(a) performing an orthopedic procedure on the subject;
(b) providing an apparatus adapted and configured to selectively control an articulation of a joint of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable about a first axis to a second position and selectively rotatable about a second axis, a coupling member adapted and configured to connect the fixable platform to the dynamic platform or the base, at least one of one or more sensors or data collection devices configured to sense a joint motion of the subject in communication with the platform and at least one medical diagnostic device, wherein the apparatus is adapted and configured to collect data from the at least one medical diagnostic device and the at least one of one or more sensors or data collection devices during rotation of the dynamic platform;
(c) selecting, on the subject, a target skeletal joint for examination;
(d) attaching at least one surface electromyography sensor to the subject in near proximity to the target skeletal joint;
(e) positioning the subject in a first position such that a first body part is at least partially adjacent the fixable platform, and second body part is at least partially adjacent the dynamic platform;
(f) manually moving the target skeletal joint from the first position to a second position different from the first position;
(g) capturing data from the sensor while the apparatus and the target skeletal joint are in manual motion;
(h) automatically moving the target skeletal joint from the first position to the second position different from the first position;
(h) capturing data from the sensors while the apparatus and the target skeletal joint are in automatic motion; and
(i) determining a performance of an orthopedic procedure.

65. The method of claim 64 further comprising the step of comparing sensor data captured while the apparatus and target skeletal joint are in manual motion to sensor data captured while the apparatus and target skeletal joint are in automatic motion.

66. The method of claim 64 wherein the sensor unit is configured to sense a force of the dynamic platform.

67. A method for assessing a clinical condition in a subject comprising:
(a) providing an apparatus adapted and configured to selectively control an articulation of a joint of the subject having a base positioned in a first base plane, a fixable platform adapted and configured to engage the base at an attachment mechanism, the fixable platform having a first position in a first fixable platform plane and fixably adjustable to a second position, a dynamic platform having a first position in a first dynamic platform plane, adjustable about a first axis to a second position and selectively rotatable about a second axis, a coupling member adapted and configured to connect the fixable platform to the dynamic platform or the base, a sensor unit configured to sense a joint motion of the subject in communication with the platform and at least one medical diagnostic device, wherein the apparatus is adapted and configured to collect data from the at least one medical diagnostic device and the sensor unit during rotation of the dynamic platform;
(b) selecting, on the subject, a target skeletal joint for examination;
(c) positioning the subject in a first position such that a first body part is at least partially adjacent the fixable platform, and second body part is at least partially adjacent the dynamic platform;
(d) moving the target skeletal joint from a first position to a second position different from the first position, by moving at least one of the fixable platform plane and the dynamic platform;
(e) capturing data from the sensor while the at least one of the fixable platform plane and the dynamic platform and the target skeletal joint are in motion;
(f) analyzing the captured data; and
(g) generating a data output having less than 5% error.

68. The method of claim 67 further comprising the step of comparing sensor data captured while the at least one of the fixable platform plane and the dynamic platform and target skeletal joint are in manual motion to sensor data captured while the at least one of the fixable platform plane and the dynamic platform and target skeletal joint are in automatic motion.

69. The method of claim 67, further comprising applying a predetermined constant resistive load force to the particular skeletal joint while the particular skeletal joint selected for examination is moving.

70. The method of claim 67 further comprising the step of comparing the captured data to a database of data captured from a population of patients engaging in a movement of a target skeletal joint from a first position to a second position different from the first position.

71. The method of claim 67 wherein the sensor unit is configured to sense a force of the dynamic platform.

72. Apparatus for measuring the motion of a joint of a subject, comprising:
- a motion device, comprising a platform base, a fixable platform, a dynamic platform, a means for controlling the movement of the dynamic platform, a means for exerting a resistive load force on the subject when positioned in the apparatus during motion of the dynamic platform and a means for measurement of the motion of the subject wherein the means for measurement of the motion of the subject is in communication with at least one platform and at least one medical diagnostic device, wherein the motion device is adapted and configured to collect data from the at least one medical diagnostic device and the means for measurement of the motion of the subject during rotation of the dynamic platform,
- in which the dynamic platform is adjustably connected to the platform base and the fixable platform,
- in which the apparatus is adapted to receive at least one of a posture-assistance device and an adjustable restraining device
- and wherein said dynamic platform is able to move within a plane relative to the platform base.

73. An apparatus as claimed in claim 72, in which a mechanical or rotational guide is interposed between the frame and dynamic platform and connected thereto.

74. The apparatus of claim 72 wherein the sensor unit is configured to sense a force of the dynamic platform.

75. A method for the measurement of the relative motion of a skeletal structures in a subject, comprising:
(i) positioning a subject in an apparatus according to claim 1,
(ii) initiating the imaging procedure of the subject and collecting the image data using an imaging device,
(iii) processing the data and presenting the output in quantitative or graphical form.

76. A method for the measurement of the relative motion of skeletal structures in a subject as claimed in claim 75, in which a goniometer is attached to the subject prior to step (i).

77. A method for the measurement of the relative motion of skeletal structures in a subject, comprising:
(i) attaching a goniometer to the body of said subject,
(ii) attaching means for measuring the motion of the skeletal structures of the subject when under load wherein the means for measuring is configured to sense the joint motion of the subject,
(iii) initiating the measuring procedure of the subject,
(iv) processing the collected data and presenting the output in quantitative or graphical form.

78. A method as claimed in claim 77, further comprising attaching one or more weights to the body of the subject and arranging said weights around at least one of the limbs the body of said subject.

79. A method as claimed in claim 78, in which the series of weights is interconnected through at least one of wires and pulleys.

80. A method as claimed in claim 78, in which the means for measuring the motion of the skeletal structures of the subject when under load comprises an imaging device.

81. A method as claimed in claim 78, in which the method additionally comprises the step of attaching a means for measuring the load applied to the subject.

82. A method as claimed in claim 78, in which the method additionally comprises the step of attaching an electromyography sensor to a muscle of the subject.

83. A method as claimed in claim 78, in which the method additionally comprises the step of administering a pharmaceutically active substance to the subject prior to initiating the measuring or imaging procedure.

84. A method as claimed in claim 83, in which the pharmaceutically active substance is an opioid substance.

85. A method as claimed in claim 83, in which the pharmaceutically active substance a muscle relaxant drug.

86. A method as claimed in claim 85, in which the muscle relaxant drug is selected from the group consisting of baclofen, carisoprodol, chlorphenesin, chloroxazone, cyclobenzaprine, dantrolone, diazepam, metaxalone, methcarbamol or orphenadrine.

87. A method as claimed in claim 83, in which the pharmaceutically active substance is a non-opioid analgesic.

88. A method as claimed in claim 87, in which the non-opioid analgesic is fentanyl.

89. The method of claim 77 wherein the sensor unit is configured to sense a force of the dynamic platform.

90. A method for the diagnosis of a functional derangement of a joint, the method comprising analyzing the relative motion of skeletal structures according a method of claim 78.

* * * * *